United States Patent
Xin et al.

(10) Patent No.: US 10,982,278 B2
(45) Date of Patent: Apr. 20, 2021

(54) METHODS FOR LINKING POLYNUCLEOTIDES

(71) Applicant: THE BROAD INSTITUTE, INC., Cambridge, MA (US)

(72) Inventors: Xiaofeng Xin, Cambridge, MA (US); Robert Nicol, Cambridge, MA (US)

(73) Assignee: THE BROAD INSTITUTE, INC., Cambridge, MA (US)

( * ) Notice: Subject to any disclaimer, the term of this patent is extended or adjusted under 35 U.S.C. 154(b) by 0 days.

(21) Appl. No.: 16/608,769

(22) PCT Filed: Apr. 26, 2018

(86) PCT No.: PCT/US2018/029663
§ 371 (c)(1),
(2) Date: Oct. 25, 2019

(87) PCT Pub. No.: WO2018/200884
PCT Pub. Date: Nov. 1, 2018

(65) Prior Publication Data
US 2020/0208209 A1 Jul. 2, 2020

Related U.S. Application Data

(60) Provisional application No. 62/490,453, filed on Apr. 26, 2017.

(51) Int. Cl.
*C12Q 1/6869* (2018.01)
*C12N 5/0781* (2010.01)
*C12N 5/0783* (2010.01)
*C12Q 1/6827* (2018.01)

(52) U.S. Cl.
CPC ......... *C12Q 1/6869* (2013.01); *C12N 5/0635* (2013.01); *C12N 5/0636* (2013.01); *C12Q 1/6827* (2013.01)

(58) Field of Classification Search
None
See application file for complete search history.

(56) References Cited

U.S. PATENT DOCUMENTS

2014/0206554 A1* 7/2014 Hindson .............. C12Q 1/6874
506/4
2016/0122814 A1 5/2016 Despotovic et al.

FOREIGN PATENT DOCUMENTS

| GB | 2332516 A | 6/1999 | |
|----|-----------|--------|---|
| WO | 2012106546 A2 | 8/2012 | |
| WO | WO-2012106546 A2 * | 8/2012 | ......... C12N 15/1093 |
| WO | 2012106546 A3 | 11/2013 | |
| WO | 2014142850 A1 | 9/2014 | |
| WO | 2016081549 A1 | 5/2016 | |
| WO | 2018200884 A1 | 11/2018 | |

OTHER PUBLICATIONS

Baharlou, "International Preliminary Report on Patentability for International Application PCT/US2018/029663 filed Apr. 26, 2018", dated Oct. 29, 2019, 6 pages.
"International Search Report and Written Opinion for International Application PCT/US2018/029663 filed Apr. 26, 2018", dated Jul. 9, 2018, 15 pages.
Boren, et al., "Ruthenium-Catalyzed Azide—Alkyne Cycloaddition: Scope and Mechanism", J Am Chem Soc 130:8923-8930, 2008.
Gnerre, et al., "High-quality draft assemblies of mammalian genomes from massively parallel sequence data", Proc. Natl. Acad. Sci., vol. 108, No. 4, pp. 1513-1518, Jan. 25, 2011.
Himo, "Copper(I)-Catalyzed Synthesis of Azoles. DFT Study Predicts Unprecedented Reactivity and Intermediates", J Am Chem Soc 127:210-216, 2005.
Menzel, et al., "Comprehensive Evaluation and Optimization of Amplicon Library Preparation Methods for High-Throughput Antibody Sequencing", PLOS ONE, vol. 9, No. 5, Jan. 1, 2014 (Jan. 1, 2014) p. e96727, XP055443575, DOI: 10.1371/journal.pone.0096727, 12 pages.
Moonsamy, et al., "High Throughput HLA Genotyping Using 454 Sequencing and the Fluidigm Access Array System for Simplified Amplicon Library Preparation", Tissue Antigens, vol. 81, No. 3, Feb. 10, 2013 (Feb. 10, 2013), pp. 141-149, XP55127659.
Rostovtsev, et al., Angew Chem Int Ed 41:2596-2599, 2002.

* cited by examiner

*Primary Examiner* — Tracy Vivlemore
*Assistant Examiner* — Sahana S Kaup
(74) *Attorney, Agent, or Firm* — Johnson, Marcou, Isaacs & Nix, LLC; F. Brent Nix, Esq.; Xiaoban Xin, Esq.

(57) ABSTRACT

The present disclosure generally relates to methods and compositions of linking, amplifying, and sequencing nucleic acid molecules. Also disclosed is the use of 5'-5'linked oligonucleotides for linking nucleic acid molecules for sequencing of the ends of long nucleic acid template molecules, or for sequencing polymorphism or different target genes or different RNAs simultaneously.

14 Claims, 30 Drawing Sheets
Specification includes a Sequence Listing.

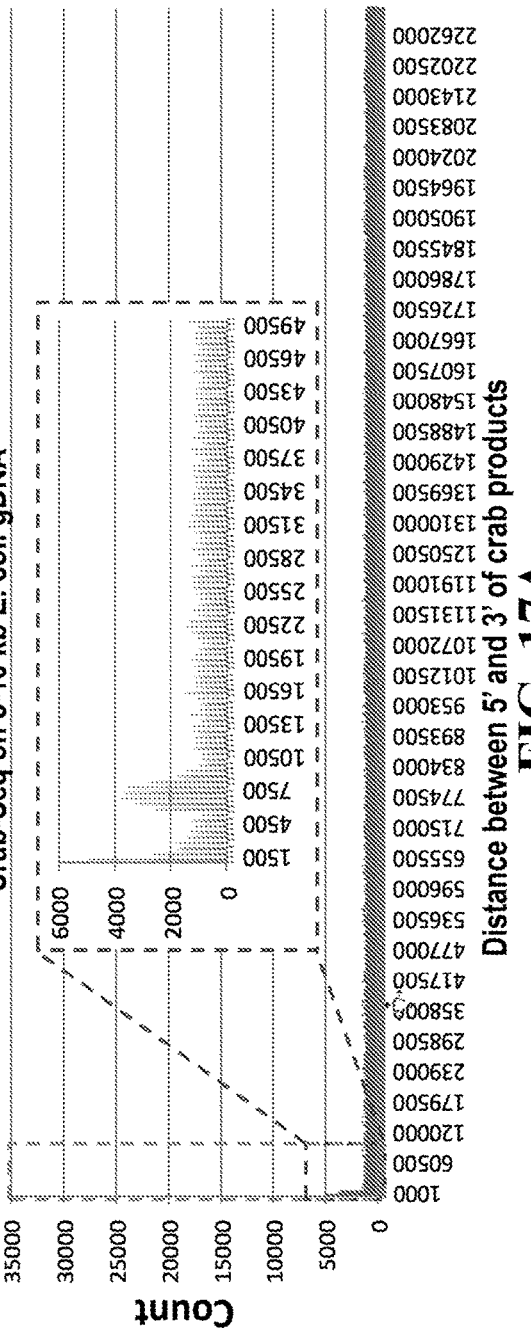
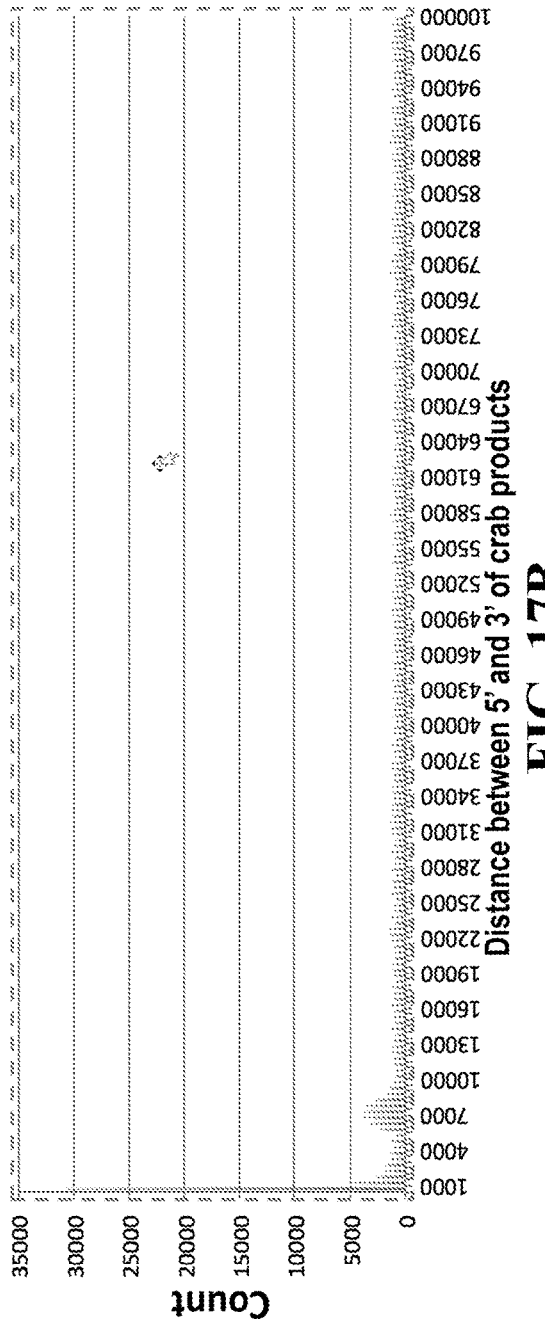
FIG. 17A
FIG. 17B

METHODS FOR LINKING POLYNUCLEOTIDES

CROSS-REFERENCE TO RELATED APPLICATIONS

This application is a National Stage application of International Application No. PCT/US2018/029663 filed Apr. 26, 2018, which claims the benefit of U.S. Provisional Application No. 62/490,453, filed Apr. 26, 2017. The entire contents of the above-identified applications are hereby fully incorporated herein by reference.

STATEMENT REGARDING FEDERALLY SPONSORED RESEARCH

This invention was made with government support under grant number HR0011-15-C-0084 granted by the Defense Advanced Research Projects Agency. The government has certain rights in the invention.

REFERENCE TO AN ELECTRONIC SEQUENCE LISTING

The contents of the electronic sequence listing ("FINAL BROD-0681_Sequence_Listing_ST25.txt," 16,775 bytes and created on Apr. 25, 2018) is herein incorporated by reference in its entirety.

TECHNICAL FIELD

The present invention relates to methods for sequencing, retrieving, assembling, and/or cloning nucleic acids. More specifically, the invention relates to the use of 5'-5'linked oligonucleotides for linking DNA molecules for sequencing of the ends of long DNA template molecules, or for sequencing polymorphism or different target genes or different RNAs simultaneously.

BACKGROUND

Reliable and simultaneous detection, sequencing, and cloning of multiple different polynucleotides has presented a great challenge to the biomedical and life sciences. Examples of multiple different polynucleotides may include the ends of long DNA molecules, different mRNA molecules present in a single cell, and multiple mutations present in a single cancer cell. Methods for simultaneous detection, sequencing, and cloning of such polynucleotides would present significant advantages over currently available technology in terms of cost, efficiency, sensitivity, and specificity.

SUMMARY

In one aspect, the present disclosure provides a method for linking two or more nucleic acid molecules or fragments thereof, comprising: (a) segregating a cell or the nucleic acid molecules into individual discrete volumes; (b) annealing, within each individual discrete volume, said two or more nucleic acid molecules using a first primer and a second primer, wherein the first and second primers are linked by a 5'-5'-covalent linkage, and wherein the first primer hybridizes to a first sequence of a first nucleic acid molecule of said two or more nucleic acid molecules and the second primer hybridizes to a second sequence of a second nucleic acid molecule of said two or more nucleic acid molecules, to create a complex comprising the first and the second nucleic acid molecules.

In some embodiments, the first and the second nucleic acid molecules are RNAs or mRNAs. The mRNAs may encode immunoglobulin light chain and heavy chain, or T cell receptor-α and T cell receptor-β. In some embodiments, the first and the second nucleic acid molecules are genomic DNAs. The genomic DNAs may comprise polymorphic sequences. In some embodiments, the cell is a B cell or a T cell. The cell may be isolated from a healthy subject at different time points or under different health conditions, or from a subject with a recent infection or administered with a vaccine.

In other embodiments, the method further comprises amplifying the first and the second nucleic acid molecules in the complex with a reverse transcriptase under conditions to create a first cDNA complementary to the first nucleic acid molecule and a second cDNA complementary to the second nucleic acid molecule. Amplifying the first and the second nucleic acid molecules may comprise contacting the complex with a third primer that hybridizes to a sequence of the first cDNA and a fourth primer that hybridizes to a sequence of the second cDNA and creating a third cDNA complementary to the first cDNA and a fourth cDNA complementary to the second cDNA. The third and the fourth primers may be unlinked or linked by a 5'-5'-covalent linkage. In some embodiments, amplifying the first and the second nucleic acid molecules may comprise contacting the complex with a template switching adapter and a third primer that primes at the template switching adapter and creating a third cDNA complementary to the first cDNA and a fourth cDNA complementary to the second cDNA.

In other embodiments, the method may further comprise amplifying the first and the second nucleic acid molecules in the complex under conditions to create a first DNA complementary to the first nucleic acid molecule and a second DNA complementary to the second nucleic acid molecule. Amplifying the first and the second nucleic acid molecules may further comprise contacting the complex with a third primer that hybridizes to a sequence of the first DNA and a fourth primer that hybridizes to a sequence of the second DNA and creating a third DNA complementary to the first DNA and a fourth DNA complementary to the second DNA.

In certain embodiments, the first and the second primers are 5'-5' linked via PCR amplification, isothermal amplification, ligation, click chemistry, or oligonucleotide chemical synthesis. The primers may be linked using a biocompatible reaction. The biocompatible reaction can be selected from the group consisting of a copper(I)-catalyzed azide-alkyne cycloaddition (CuAAC) reaction, a copper-free strain-promoted azide-alkyne cycloaddition (SPAAC) reaction, and a thiol-ene reaction.

In some embodiments, the first primer, the second primer, both primers, or the linkage can comprise a binding tag. The binding tag may be an affinity pull-down functional group, for example, a biotin or desthiobiotin group. In some embodiments, the method can further comprise isolating the complex comprising the first and the second nucleic acid molecules and the first and second primers by affinity pull-down, for example, by contacting the complex with a streptavidin linked tag.

In some embodiments, the individual discrete volume is a droplet generated by emulsification. The droplet may be generated by vortexing or shaking, or on a microfluidic device. In other embodiments, the individual discrete volume is a hollow particle of sufficient size to hold reaction mixture, for example, a section of a thin capillary tube.

In another aspect, the present disclosure provides a method for linking nucleic acid molecules or fragments thereof, comprising: (a) segregating individual nucleic acid molecules labeled on both terminal ends with a first adapter pair comprising a forward sequence (F) and a reverse sequence (R), into individual discrete volumes; (b) inserting, within the individual discrete volumes, at least a second adapter into two or more interior locations of the nucleic acid molecule; (c) fragmenting the nucleic acid molecules to generate nucleic acid fragments of the nucleic acid molecule of which a least a portion are labeled with both the first adapter pair and the second adapter; (d) contacting the nucleic acid fragments with at least a first and a second primer, wherein the first primer comprises at least two 5'-5'-linked arms, wherein a first arm of the at least two 5'-5'-linked arms comprises a sequence that hybridizes to the forward (F) sequence of the first adapter pair and a second arm of the at least two 5'-5'-linked arms comprises a sequence that hybridizes to the reverse (R) sequence of the first adapter pair, and wherein the second primer comprises a sequence that hybridizes to the second adapter; and (e) amplifying the nucleic acid molecules using both the first and second primers by PCR amplification or isothermal amplification.

In some embodiments, the method may further comprise: (f) pooling the amplified nucleic acid fragments from each individual discrete volume; and (g) circularizing the amplified nucleic acid fragments by joining the second adapters. In some embodiments, the method may further comprise: (h) PCR amplification to generate linearized nucleic acid molecules comprising the second adapter; and (i) sequencing the linearized nucleic acid molecules to generate a set of nucleic acid reads. In other embodiments, the method may comprise isolating the amplified nucleic acid fragments labeled with the first primer prior to the circularization step, or exonuclease digestion prior to the PCR amplification step to generate linearized nucleic acid molecules. The method may further comprise removing the first adapter pair sequence from the circularized nucleic acid molecules to generate linearized nucleic acid molecules comprising the second adapter prior to the PCR amplification step. In other embodiments, the method may comprise assembling a nucleic acid sequence of the nucleic acid molecules based, at least in part, on the set of nucleic acid sequencing reads.

In some embodiments, the first arm and the second arm are each between 5 to 1000 bps in length. The first and the second arms may be 5'-5' linked via PCR amplification, isothermal amplification, ligation, click chemistry, or oligonucleotide chemical synthesis. The arms may be linked using a biocompatible reaction. The biocompatible reaction can be selected from the group consisting of a copper(I)-catalyzed azide-alkyne cycloaddition (CuAAC) reaction, a copper-free strain-promoted azide-alkyne cycloaddition (SPAAC) reaction, and a thiol-ene reaction.

In some embodiments, the first arm, the second arm, both arms, or the linkage can comprise a binding tag. The binding tag may be an affinity pull-down functional group, for example, a biotin or desthiobiotin group. In some embodiments, the method can further comprise isolating the amplified nucleic acid fragments labeled with the first primer via the binding tag.

In other embodiments, the forward (F) sequence and the reverse (R) sequence are between 6 and 5000 nucleotides in length. The forward (F) sequence and the reverse (R) sequence can be the same or different. In some embodiments, the forward (F) sequence, the reverse (R) sequence, or the second adapter can further comprise a restriction site. The restriction site can be a Type IIS restriction site, for example, a SapI, AcuI, BpuEI, or BsgI restriction site. The method can further comprise removing or shortening the forward (F) sequence, the reverse (R) sequence, or the second adapter from the circularized nucleic acid fragments by a restriction enzyme recognizing the restriction site.

In some embodiments, the first arm of the first primer comprises a forward sequencing adapter sequence or a fragment thereof, and the second arm of the first primer comprises a reverse sequencing adapter sequence or a fragment thereof. In other embodiments, the end-labeled nucleic acid molecules are fragmented by a transposase.

In certain embodiments, the individual discrete volume is a droplet generated by emulsification. The droplet may be generated by vortexing or shaking, or on a microfluidic device. The droplet may comprise the transposase, the second adapter, and the first and the second primers. In other embodiments, the individual discrete volume is a hollow particle of sufficient size to hold reaction mixture, for example, a section of a thin capillary tube.

The nucleic acid molecules may be DNA or RNA molecules. In some embodiments, the nucleic acid molecules are 5 kb or longer, or 40-100 kb or longer. The nucleic acid molecules may encode T-cell receptor, B-cell receptor, or immunoglobulin heavy or light chain.

Another aspect of the present disclosure provide a method for linking nucleic acid molecules or fragments thereof, comprising: (a) segregating individual nucleic acid molecules labeled on both terminal ends with an adapter pair comprising a forward sequence (F) and a reverse sequence (R), into individual discrete volumes; (b) contacting, within each individual discrete volume, the nucleic acid molecules labeled with the adapter pair with at least a first primer and a second primer, wherein the first primer comprises at least two 5'-5'-linked arms, wherein a first arm of the at least two 5'-5'-linked arms comprises a sequence that hybridizes to the forward (F) sequence of the adapter pair and a second arm of the at least two 5'-5'-linked arms comprises a sequence that hybridizes to the reverse (R) sequence of the adapter pair, wherein the second primer comprises a sequence that hybridizes to the forward (F) sequence of the adapter pair, the reverse (R) sequence of the adapter pair, or an internal conserved region of the nucleic acid molecule; and (c) amplifying the nucleic acid molecules using both the first and the second primers by PCR or isothermal amplification.

In some embodiments, the method may further comprise: (f) pooling the amplified nucleic acid fragments from each individual discrete volume; and (g) circularizing the amplified nucleic acid fragments. In some embodiments, the method may further comprise: (h) PCR amplification to generate linearized nucleic acid molecules comprising the adapter pair sequences; and sequencing the linearized nucleic acid molecules to generate a set of nucleic acid reads. In other embodiments, the method may comprise isolating the amplified nucleic acid fragments labeled with the first primer prior to the circularization step, or exonuclease digestion prior to the PCR amplification step. In other embodiments, the method may comprise assembling a nucleic acid sequence of the nucleic acid molecules based, at least in part, on the set of nucleic acid sequencing reads.

In some embodiments, the first arm and the second arm are each between 5 to 1000 bps in length. The first and the second arms may be 5'-5' linked via PCR amplification, isothermal amplification, ligation, click chemistry or oligonucleotide chemical synthesis. The arms may be linked using a biocompatible reaction. The biocompatible reaction can be selected from the group consisting of a copper(I)-catalyzed azide-alkyne cycloaddition (CuAAC) reaction, a copper-free strain-promoted azide-alkyne cycloaddition (SPAAC) reaction, and a thiol-ene reaction.

In some embodiments, the first arm, the second arm, both arms, or the linkage can comprise a binding tag. The binding tag may be an affinity pull-down functional group, for example, a biotin or desthiobiotin group. In some embodiments, the method can further comprise isolating the amplified nucleic acid fragments labeled with the first primer via the binding tag.

In other embodiments, the forward (F) sequence and the reverse (R) sequence are between 6 and 5000 nucleotides in length. The forward (F) sequence and the reverse (R) sequence can be the same or different. In some embodiments, the forward (F) sequence or the reverse (R) sequence can further comprise a restriction site. The restriction site can be a Type IIS restriction site, for example, a SapI, AcuI, BpuEI, or BsgI restriction site. The method can further comprise removing or shortening the forward (F) sequence or the reverse (R) sequence from the circularized nucleic acid fragments by a restriction enzyme recognizing the restriction site.

In some embodiments, the first arm of the first primer comprises a forward sequencing adapter sequence or a fragment thereof, and the second arm of the first primer comprises a reverse sequencing adapter sequence or a fragment thereof.

In certain embodiments, the individual discrete volume is a droplet generated by emulsification. The droplet may be generated by vortexing or shaking, or on a microfluidic device. In other embodiments, the individual discrete volume is a hollow particle of sufficient size to hold reaction mixture, for example, a section of a thin capillary tube.

In some embodiments, the nucleic acid molecules can be DNA molecules or RNA molecules. The nucleic acid molecules may encode T-cell receptor, B-cell receptor, or immunoglobulin heavy chain or light chain.

In another aspect, the present disclosure provides a composition for linking two or more nucleic acid molecules, comprising at least a first and a second nucleic acid molecule and a first and a second primer, wherein the first and the second primers are linked by a 5'-5'-covalent linkage, and wherein the first primer comprises a sequence that hybridizes to a first conserved sequence of the first nucleic acid molecule and the second primer comprises a sequence that hybridizes to a second conserved sequence of the second nucleic acid molecule.

In some embodiments, the composition can further comprise a first DNA molecule amplified from the first primer and a second DNA molecule amplified from the second primer, wherein the first DNA molecule is complementary to the first nucleic acid molecule and the second DNA molecule is complementary to the second nucleic acid molecule. In other embodiments, the composition can further comprise a third primer and a fourth primer, wherein the third primer comprises a sequence that hybridizes to the first DNA molecule and the fourth primer comprises a sequence that hybridizes to the second DNA molecule. The third primer and the fourth primer may be linked by a 5'-5'-covalent linkage.

Another aspect of the present disclosure provides a circularized DNA molecule for linking and/or sequencing two ends of a nucleic acid molecules, comprising: a first primer, both ends of the nucleic acid molecule and an internal adapter sequence, wherein the internal adapter is inserted in the nucleic acid molecule, wherein the ends of the nucleic acid molecule are labeled with a forward (F) sequence and a reverse (R) sequence, wherein the first primer comprises at least two 5'-5'-linked arms linking the two ends of the nucleic acid molecule, wherein a first arm of the at least two 5'-5'-linked arms comprises a sequence that hybridizes to the forward (F) sequence and a second arm of the at least two 5'-5'-linked arms comprises a sequence that hybridizes to the reverse (R) sequence, and wherein the linked ends of the nucleic acid molecule are ligated by ligase at their distal ends.

In another aspect, the present disclosure provides a circularized DNA molecule for linking and/or sequencing two nucleic acid molecules, comprising: a primer and two nucleic acid molecules comprising a first and a second nucleic acid molecules, wherein the primer comprises at least two 5'-5'-linked arms linking the two nucleic acid molecules, wherein a first arm of the at least two 5'-5'-linked arms comprises a sequence that hybridizes to the first nucleic acid molecule and a second arm of the at least two 5'-5'-linked arms comprises a sequence that hybridizes to the second nucleic acid molecules, and wherein the linked two nucleic acid molecules are ligated by ligase at their distal ends. In some embodiments, the circularized DNA further comprises a second primer or a second adapter, wherein the second primer or second adapter labels the distal ends of the two nucleic acid molecules before they are ligated by ligase.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 17A shows sequencing results of Crab-Seq on 5-10 kb *E. coli* gDNA. FIG. 17B shows results on a different scale.

DETAILED DESCRIPTION OF THE EXAMPLE EMBODIMENTS

General Definitions

Figure 1:
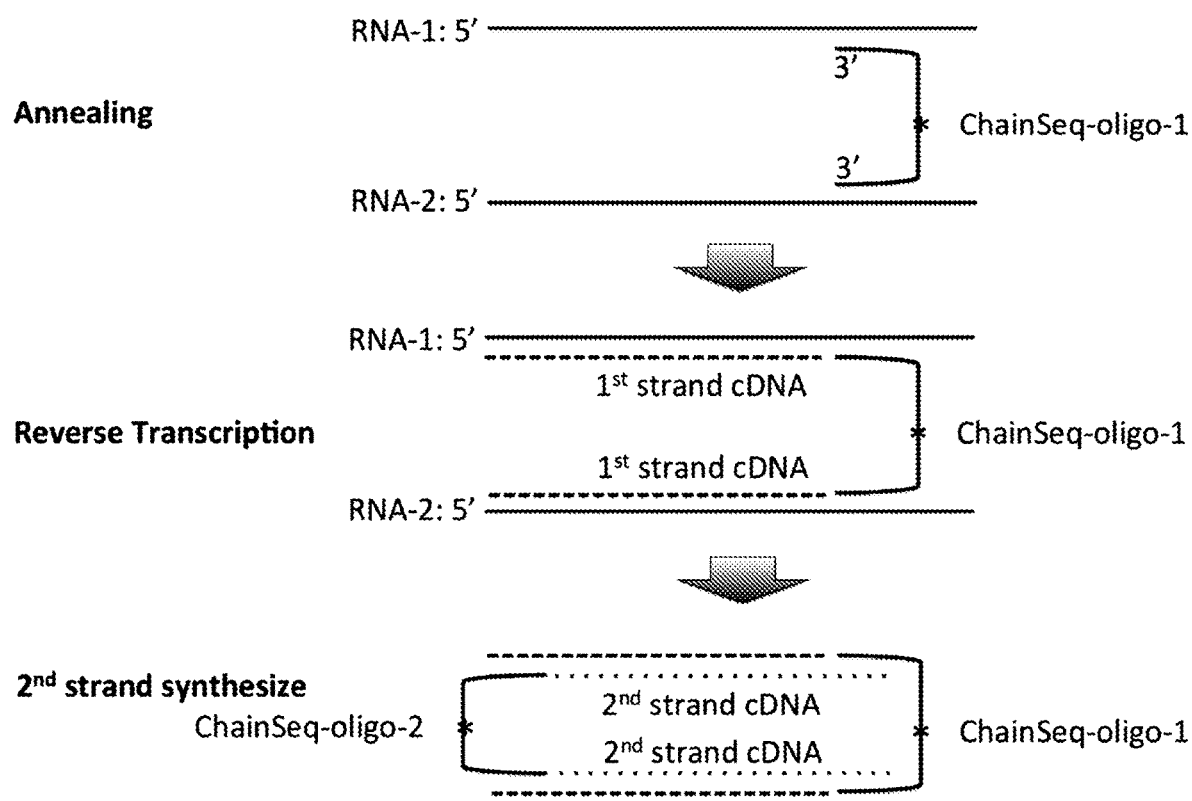
FIG. 1 shows a chain-oligo having two arms, in accordance with certain example embodiments.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "chain-oligo or oligonucleotide" and "craboligo or crab nucleotide" may be used interchangeably herein.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment", "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods, primers, and kits for covalently linking polynucleotides which has application in, for example, de novo genome assembly, long range mutation detection, mapping of repeating regions, and synthetic biology construct validation. In particular, the embodiments disclosed herein are well adapted for applications requiring the manipulation and/or sequencing of large polynucleotide molecules. Existing techniques sequencing large DNA reads are costly, require large DNA inputs, suffer from higher error rates than sequencing shorter reads, and are typically much less efficient when used with oligonucleotides that are greater than 5 kb.

In certain aspects, the embodiments disclosed herein utilizes amplification of target oligonucleotides using 5'-5' linked oligonucleotides, referred to herein as chain-seq oligos or crab oligos. The chain-seq oligos comprise two or more separate oligonucleotide arms that are linked to one another at the 5' end of each arm. Thus, each arm of the chain-oligo has two or more free 3' ends and comprise at least a hybridization domain capable of binding to a complementary sequence on a target oligonucleotide. The chain-seq oligos may be designed to bind to RNA, DNA, or a combination thereof. Amplification reactions utilizing the chain-seq oligo then result in a single amplicon or molecule that incorporates the sequence of both target molecules. This single amplicon or molecule may then be used in further processing steps such as, but not limited to, sequencing.

In certain example embodiments, the target oligonucleotides are smaller fragments originating from the same larger oligonucleotide. In certain example embodiments, the large oligonucleotide is a DNA oligonucleotide. In certain example embodiments, a "large oligonucleotide" is an oligonucleotide that is at least about 5 kB, 6 kB, 7 kB, 8 kB, 9 kB, 10 kB, 11 kB, 12 kB, 13 kB, 14 kB, 15 kB, 16 kB, 17 kB, 18 kB, 19 kB, 20 kB, 21 kB, 22 kB, 23 kB, 24 kB, 25 kB, 26 kB, 27 kB, 28 kB, 29 kB, 30 kB, 31 kB, 32 kB, 33 kB, 34 kB, 35 kB, 36 kB, 37 kB, 38 kB, 39 kB, 40 kB, and the like.

Before describing the various methods disclosed herein in detail, a brief discussion of various features of the component parts of the invention is provided.

5'-5' Linked Oligonucleotides

In certain embodiments, covalent linkage of polynucleotides is achieved using 5'-5' linked oligonucleotides, also referred to herein as a "chain-seq" or "crab-seq" oligonucleotide. A 5'-5' linked oligonucleotide comprises two or more "arms," each comprising an oligonucleotide sequence that is linked at the 5' end via a covalent or non-covalent biocompatible linkage. Thus, the chain-seq oligonucleotide comprises two or more free 3' ends. Each arm of the 5'-5' linked oligonucleotide may comprise the same oligonucleotide sequence, or each arm may comprise a different oligonucleotide sequence. Likewise, the oligonucleotide sequences of each arm may be the same or of different lengths. In certain embodiments, an individual arm may be from about 8 to about 1000 nucleotides in length. For example, an individual arm may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or the like. Linking together individual nucleic acid molecules as described herein may result in a nucleic acid construct of any size, containing any number of joined nucleic acid molecules appropriate in accordance with the invention.

Each arm may be single stranded, double stranded, or a combination thereof. The oligonucleotide may comprise DNA, RNA, or a combination thereof. The arms may also comprise, in full or in part, nucleotide analogs such as peptide nucleic acids, morpholino and locked nucleic acids, glycol nucleic acid, and threose nucleic acids.

In some embodiments, a portion of each arm of the 5'-5' linked oligonucleotide may comprise a binding domain comprising a nucleic acid sequence that is complementary to and hybridizes with a target sequence. A target sequence may be a naturally occurring nucleic acid sequence or may be artificially introduced into a target polynucleotide as appropriate depending on the application.

In certain embodiments, a 5'-5' linked oligonucleotide may comprise at least two, at least three, at least four, at least five, at least six, at least seven, at least eight arms, or any number of arms as appropriate for the number of target oligonucleotides to be linked via the methods disclosed herein. In some embodiments, the arms of an oligonucleotide as described herein may be connected via a common linkage. In certain embodiments, each arm may recognize the same target sequence. In other embodiments, each arm, or a subset of arms, may recognize a different target sequence. For example, given a four-arm 5'-5' linked oligonucleotide, each arm may recognize up to four different target sequences. Alternatively, two arms could hybridize to a single target sequence and the remaining two arms could hybridize to a second target sequence. Other similar variations are contemplated and are within the scope of this invention.

The 5' ends of each arm may be linked to each other using means known in the art for linking nucleic acids to each other. In some embodiments, nucleic acids are linked together via a biocompatible reaction. In certain embodiments, a biocompatible reaction may comprise use of "click chemistry" (see, e.g., Rostovtsev et al., *Angew Chem Int Ed* 41:2596-2599, 2002; Himo et al., *J Am Chem Soc* 127:210-216, 2005; Boren et al., *J Am Chem Soc* 130:8923-8930, 2008). An example of a click chemistry reaction is the Huisgen 1,3-dipolar cycloaddition of alkynes to azides to form 1,4-disubstituted-1,2,3-triazoles. The copper(I)-catalyzed reaction is mild and very efficient, requiring no protecting groups, and requiring no purification, in many cases. The azide (AZ) and alkyne (AK) functional groups are largely inert towards biological molecules and aqueous environments, which allows the use of the Huisgen 1,3-dipolar cycloaddition in target-guided synthesis and activity-based protein profiling. Thus, in some embodiments, a chain oligo is formed by linking the 5' end of one nucleic acid strand that includes an azide group to the 5' end of another nucleic acid strand that includes an alkyne group. Other example biocompatible reactions include copper(I)-catalyzed azide-alkyne cycloaddition (CuAAC) reaction, a copper-free strain-promoted azide-alkyne cycloaddition (SPAAC) reaction, and a thiol-ene reaction.

In certain example embodiments, each arm of the 5'-5' linked oligonucleotide may be connected indirectly via a binding or scaffolding molecule. In other embodiments, indirect means for linking the arms of such an oligo may include use of binding or scaffolding molecules such as, but not limited to polymers, such as polyethylene glycol (PEG) and other polyethers.

In certain example embodiments, spacers may be employed, for example, to reduce steric hindrance between individual arms. The spacer may be an alkyne or an azide spacer. In some embodiments, a spacer may be joined to an oligo of the invention using direct or indirect means, including, but not limited to polymers, such as polyethylene glycol (PEG) and other polyethers. In certain embodiments, a spacer may be 8 to 1000 nucleotides in length. For example, a spacer may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 250, 300, 350, 400, 450, 500, 550, 600, 650, 700, 750, 800, 850, 900, 950, 1000, or the like.

As used herein, a nucleic acid (a polymer of nucleotides) is "single-stranded" if nucleotides that form the nucleic acid are unpaired. That is, nucleotides of a single-stranded nucleic acid are not base-paired (via Watson-Crick base pairs, e.g., guanine-cytosine and adenine-thymine/uracil) to nucleotides of another nucleic acid. A single-stranded nucleic acid may be contrasted with a double-stranded (paired) nucleic acid, a typical example of which is a DNA double helix. Single-stranded nucleic acids may include a contiguous (uninterrupted) sequence of nucleotides or, in some embodiments, a single-stranded nucleic acid may be a conjugate that includes two nucleic acid strands joined together, for example, through a chemical (covalent) linkage.

In nature, a single strand of a nucleic acid (e.g., DNA or RNA) has a 5' end (five-prime end) and a 3' end (three-prime end). The 5' end typically contains a phosphate group attached to the 5' carbon of the ribose ring of a nucleotide and a 3' end, which is unmodified from the ribose —OH substituent. Nucleic acids are synthesized in vivo in the 5' to 3' direction. Polymerase relies on the energy produced by breaking nucleoside triphosphate bonds to attach new nucleoside monophosphates to the 3'-hydroxyl (—OH) group via a phosphodiester bond.

An engineered single-stranded nucleic acid of the present disclosure has two 3' ends (a chain oligo). Each terminus of the single-stranded nucleic acid includes a 3'-hydroxyl (—OH) group. In some embodiments, a single-stranded chain oligo is formed by joining (linking) the 5' end of one single-stranded nucleic acid to the 5' end of another single-stranded nucleic acid. In some embodiments, the linkage between two 5' ends is a covalent linkage. In other embodiments, the linkage is non-covalent.

Each arm of a chain-oligo may comprise a hybridization domain. A "domain" refers to a discrete, contiguous sequence of nucleotides or nucleotide base pairs, depending on whether the domain is unpaired (single-stranded nucleotides) or paired (double-stranded nucleotide base pairs), respectively. A hybridization domain facilitates binding of the chain-oligo to a complementary sequence on a target oligonucleotide i.e. the target sequence. A domain is "complementary to" a target sequence if the domain contains nucleotides that base pair (hybridize/bind through Watson-Crick nucleotide base pairing) with nucleotides of the target sequence such that a paired (double-stranded) or partially-paired molecular species/structure is formed. Complementary domains need not be perfectly (100%) complementary to form a paired structure, although perfect complementarity is provided, in some embodiments. The length of a hybridization domain may vary. In some embodiments, a hybridization domain may have a length of 5-50 nucleotides. For example, an anchor domain may have a length of 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-40, 25-35, 25-30, 30-40, 30-35, or 35-40 nucleotides. In other embodiments, a hybridization domain may have a length of 5, 10, 15, 20, 25, 30, 35, 40, 45, or 50 nucleotides. In some embodiments, a hybridization domain may have a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. A hybridization domain, in some embodiments, may be longer than 50 nucleotides, or shorter than 5 nucleotides.

In certain example embodiments, one or more chain-oligo arms may further comprise a primer domain. A primer domain is a domain to which a primer binds. A primer is a strand of short nucleotide sequence that serves as a starting point for nucleic acid (e.g., DNA) synthesis. In some embodiments, chain oligos may comprise a pair of internal primer domains (e.g., near the linked 5' ends), which may be used for amplification of sequence-ready barcoded constructs produced using the methods of the present disclosure. The length of a primer domain may vary. In some embodiments, a primer domain may have a length of 5-50 nucleotides, for example, a length of 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-40, 25-35, 25-30, 30-40, 30-35, or 35-40 nucleotides. In some embodiments, a primer domain has a length of 5, 10, 15, 20, 25, 30, 35, 40, 45, or 50 nucleotides. In some embodiments, a primer domain has a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. A primer domain, in some embodiments, may be longer than 50 nucleotides, or shorter than 5 nucleotides.

In certain example embodiments, one or more chain-oligo arms may further comprise a sequencing adapter. A sequencing adapter is nucleotide sequence that facilitates binding of oligonucleotide sequences generated using the methods disclosed herein to complementary sequences used in certain next-generation sequencing technologies.

In certain other example embodiments, one or more chain-oligo arms may further comprise a barcode. A barcode is short sequence of nucleotides used as an identifier for an associated molecule, such as a target molecule and/or target nucleic acid. A nucleic acid barcode, or unique molecular identifier (UMI), can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Chain-oligos can be labeled with multiple nucleic acid barcodes in combinatorial fashion, such as a nucleic acid barcode concatemer. Typically, a nucleic acid barcode is used to identify a nucleic acid as being from a particular compartment (for example a discrete volume), having a particular physical property (for example, affinity, length, sequence, etc.), or having been subject to certain treatment conditions. Chain-seq oligos can be associated with multiple nucleic acid barcodes to provide information about all of these features (and more). Each member of a given population of UMIs, on the other hand, is typically associated with individual members of a particular set of identical, specific (for example, discrete volume-, physical property-, or treatment condition-specific) nucleic acid barcodes. Thus, for example, each member of a set of origin-specific nucleic acid barcodes, having identical or matched barcode sequences, may be associated with (for example, covalently bound to or a component of the same molecule as) a distinct or different UMI.

In some embodiments, a method of the invention may involve the use of a binding tag. For example, a nucleic acid as described herein may be labeled with an affinity tag, for example an affinity pull-down functional group, on the first arm, or the second arm, or both. In some embodiments, an affinity tag may be used to isolate a biomolecule of interest, for example an amplified nucleic acid, such as an amplified segment of a template DNA molecule or fragment or portion thereof. Such an amplified nucleic acid may contain one or more adaptor molecules as described herein, which may serve as a means for isolation of the nucleic acid.

As described herein, a chain oligo may have more than two arms, and thus an affinity tag may be present on a chain oligo on only a single arm, on multiple arms, or on all arms of the chain oligo. As used herein, an affinity tag may be used to isolate a biomolecule of interest, such as a nucleic acid, polynucleotide, protein, or the like. Affinity tags attached to as described herein may be removed by chemical or enzymatic means. One of skill in the art will be able to identify appropriate tagmentation methods and means for an affinity tag in accordance with the invention. Non-limiting examples of affinity tags include an enzymatic modification such as biotin or desthiobiotin; a fluorescent tag, such as green fluorescent protein (GFP), a solubilization tag, such as thioredoxin, maltose binding protein, glutathione-S-transferase, or poly(NANP). In accordance with the invention, any binding tag appropriate for the specific application may be used to isolate or separate a biomolecule of interest as described herein.

In addition to linking together DNA molecules, some embodiments of the invention involve the use of chain oligos as described herein to link together two RNA molecules. For example, a chain oligo having two arms may be bound to a first and a second RNA molecule such that the RNA molecules are linked together to form a single long RNA molecule, wherein the chain oligo is located between the first and second RNA molecules, as shown, for example, in FIG. 1. Reverse transcription may then be performed to produce cDNA of both the first and the second RNA molecules, wherein both 3' ends of the chain oligo serve as primer molecules for first-strand cDNA synthesis according to methods known in the art. In some embodiments, the newly produced cDNA may be dissociated from the template RNA molecules and a second, distinct chain oligo may hybridize to the 3' ends of the cDNA than the first chain oligo and second strand synthesis as known in the art may be performed in order to produce a double-stranded DNA copy of the starting RNA molecule. In some embodiments, second strand cDNA may be synthesized using additional conventional mRNA specific primers, or using a common template switching adapter and a primer priming a sequence in the template switching adapter.

Figure 2:
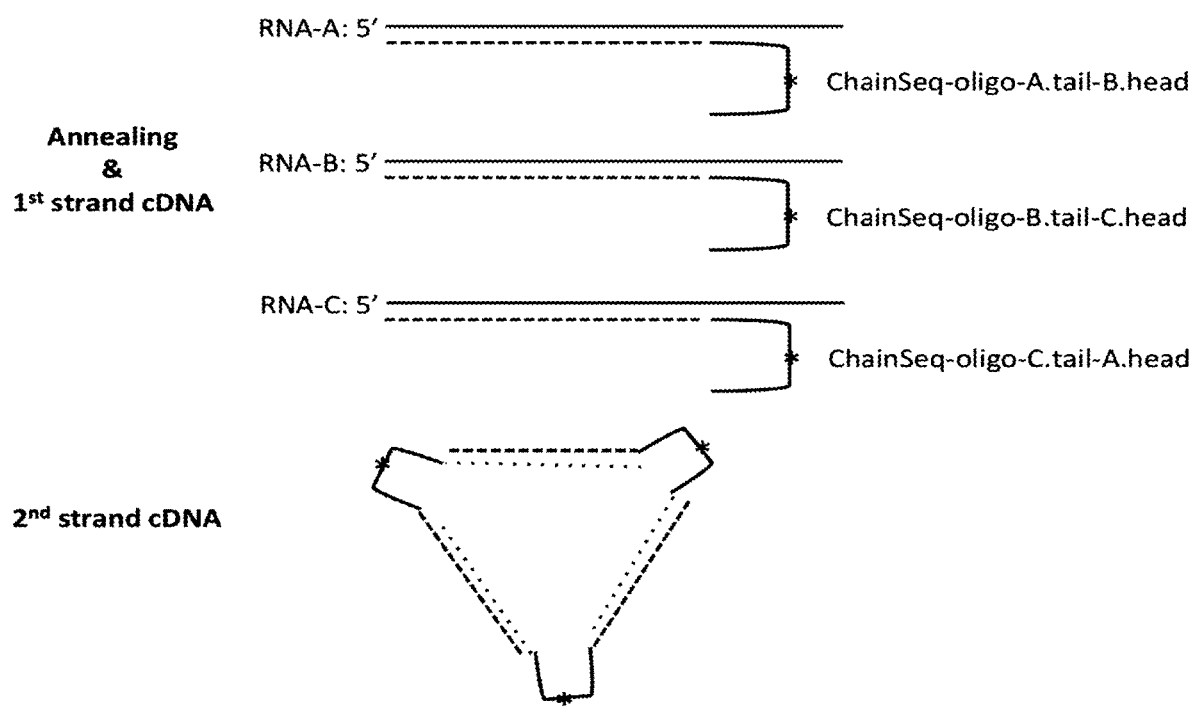
FIG. 2 shows a chain-oligo having three arms, in accordance with certain example embodiments.

In further embodiments, two or more chain oligos may be used to link together two or more RNA molecules. For example, a first chain oligo may be hybridized to a first RNA molecule, wherein the first 3' end of the first chain oligo hybridizes to the first RNA molecule and the second 3' end of the first chain oligo hybridizes to a second RNA molecule; a second chain oligo may be hybridized to a second RNA molecule, wherein the first 3' end of the second chain oligo hybridizes to the second RNA molecule and the second 3' end of the second chain oligo hybridizes to a third RNA molecule; a third chain oligo may be hybridized to a third RNA molecule, wherein the first 3' end of the third chain oligo hybridizes to the third RNA molecule and the second 3' end of the third chain oligo hybridizes to the first RNA molecule, such that a circular nucleic acid molecule is formed by the hybridization of the first, second, and third RNA molecules and the first, second, and third chain oligos as shown in FIG. 2. First strand cDNA synthesis may be performed as known in the art and as described herein.

The nucleic acid molecules linked by the 5'-5' linked oligonucleotides may be mRNA molecules encoding different transcripts. The nucleic acid molecules may encode immunoglobulin heavy and light changes, or T cell receptor α and T cell receptor β. The nucleic acid molecules linked by the 5'-5' linked oligonucleotides may be DNA molecules, for example, genomic DNAs harboring different mutations or polymorphisms. The nucleic acid molecules may be isolated from different cells, for example, immune cells including T cells, B cells, dendritic cells, macrophages, neutrophils, mast cells, eosinophils, basophils, and natural killer cells. The nucleic acid molecules may encode any cellular receptors or lectins.

In further embodiments, the 5'-5' linked oligonucleotides may be used in linking two ends of a nucleic acid molecule and downstream amplification and sequencing procedures. The nucleic acid molecule may be a DNA or RNA. The nucleic acid molecule may be at least 1 kb, at least 2 kb, at least 3 kb, at least 5 kb, at least 6 kb, at least 7 kb, at least 8 kb, at least 9 kb, or at least 10 kb in length. The use of the 5'-5' linked oligonucleotides in sequencing may be applied to archiving an immune repertoire by capturing all sequences in a Crab-Seq library derived from a human sample, such as a blood or urine sample. In further embodiments, the 5'-5' linked oligonucleotides may be used to characterize cell type specific mRNAs and to identify or profile any cell types.

Adaptor Molecules

Adaptor molecules may be used, in some embodiments, to add one or more elements to target oligonucleotides. For example, the adapter may be used to add a universal sequence complementary to the hybridization domain on a set of chain-oligos. Adapters may also be used to add primer binding sites Whether an adaptor is single-stranded, double-stranded, or partially double-stranded (partially single-stranded), depends on the target molecule to which the adaptor is being added. Typically, a double-stranded, or partially, double-stranded adaptor is added to the terminus (or termini) of a double-stranded target nucleic acid, and a single-stranded adaptor is added to the terminus of a single-stranded target nucleic acid. In some embodiments, an adaptor molecule as described herein may be a forward sequencing adaptor sequence or a reverse sequencing adaptor sequence.

A homopolymer domain is simply a contiguous stretch of the same nucleotides, such as for example, GGGG. A homopolymer may comprise adenines, guanines, cytosines or thymines (or variants thereof). It should be understood that the homopolymer domain is used to join the 3' ends of the extended whip molecule to each other to permit polymerization to form a circular, double-stranded molecule. Other means of joining the two 3' ends are encompassed by the present disclosure. Thus, the homopolymer domains may be substituted with other complementary nucleotide domains, for example.

In accordance with the invention, an adaptor molecule may be added to the outside of a template DNA molecule, referred to herein as an "outside adaptor." Other embodiments of the invention utilize an internal adaptor, which is described in more detail below. An adaptor molecule may provide a binding site for a chain oligo to hybridize to an/or provide a primer binding site for amplification or sequencing purposes. As described herein, the invention may provide for use of a number of adaptor molecules. For example, the methods described herein may use a single outside adaptor and a single internal adaptor. In other embodiments, a method of the invention may use multiple adaptor molecules, as appropriate for the particular application.

The present invention may provide in some embodiments an adaptor molecule containing one or more nucleic acid segments that may serve as a site location into which a nucleic acid segment is inserted or added. Such a segment or sequence may be introduced into an adaptor molecule through techniques known in the art, or it may be a naturally occurring sequence. For example, an adaptor molecule as described herein may be engineered or produced to contain a particular splice site, recombination or crossover site, or "hot spot," such as a Chi site or Chi sequence. This may serve as a tag for enzymatic removal of the adaptor molecule prior to sequencing of the template DNA, such as removal of a particular segment of nucleic acid by the RecBCD enzyme. In other embodiments, other sequences or sites that may stimulate or result in double-stranded DNA breakage and are useful for removal of an adaptor molecule or other nucleic acid segment at a specific location are encompassed by the present invention.

In accordance with the invention, an adaptor molecule may be any size appropriate for the particular use. In some embodiments, an adaptor as described herein may be from about 6 nucleotides in length to about 5000 nucleotides in length. For example, an adaptor may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, or the like.

In specific embodiments, more than one Chi site may be employed, such as 2 Chi sites, 3 Chi sites, or more. Instead of or in addition to a Chi site, a binding site for a restriction endonuclease may be incorporated into an adaptor molecule for addition to a template DNA as described herein. In such a case, a restriction endonuclease may be employed in order to cut the template DNA molecule at a desired location. In some embodiments, a restriction endonuclease useful in accordance with the invention may be a type IIS restriction endonuclease. One of skill in the art will recognize particular restriction endonucleases that may be useful for the invention, for example, SapI. In this regard, it should be noted that any restriction endonuclease that recognizes a particular sequence and will cut DNA as required for a particular application is appropriate for use with the invention, on the condition that the recognition site for the particular restriction endonuclease is added to the template DNA molecule. A restriction endonuclease may be employed to remove an adaptor molecule from the template DNA molecule. In some embodiments, the template DNA molecule may be in circular form or linear form when the adaptor molecule is removed using a restriction endonuclease.

The 5'-5' linked oligonucleotides described herein may be used to isolate, amplify and/or covalently link a number of nucleic acid fragments for a number of different applications, including but not limited to, de novo genome assembly, genomic deletion and insertion detection, genomic repeat detection, synthetic biology construct verification, T-cell receptor profiling, B-cell receptor profiling, T-cell receptor cloning, multiplex RNA or DNA molecule combination detection, such as multiple mutation combination detection and profiling in single cells, such as cancer cells, and cloning of multiplex DNA molecules, as described in further detail below.

Barcode Nucleic Acids

Systems and methods of the present disclosure, in some embodiments, may use a chain oligo in combination with a barcoded nucleic acid. A "barcoded nucleic acid" is a nucleic acid, typically single-stranded, that includes a barcode domain. A "barcode domain" is a domain that includes a nucleotide sequence that can be used to identify the barcoded nucleic acid or to identify one or more biomolecules to which the barcoded nucleic acid is directly or indirectly linked. A barcoded nucleic acid may include a barcode domain that is unique to that single nucleic acid (among a population of barcoded nucleic acids, the barcode is specific to that one nucleic acid) or a barcode domain that is unique to a subpopulation of nucleic acids (among multiple populations of barcoded nucleic acids, the barcode is specific to a single subpopulation of barcoded nucleic acids). The length of a barcode domain may vary. For example, a barcode domain may have a length of 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-40, 25-35, 25-30, 30-40, 30-35, or 35-40 nucleotides. In some embodiments, a barcode domain may have a length of 5, 10, 15, 20, 25, 30, 35, 40, 45, or 50 nucleotides. In some embodiments, a barcode domain may have a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. A barcode domain, in some embodiments, may be longer than 50 nucleotides, or shorter than 5 nucleotides.

The length of a barcoded nucleic acid itself may vary. In some embodiments, the length of a barcoded nucleic acid may be 20-1000 nucleotides, for example a length of 20-900, 20-800, 20-700, 20-600, 20-500, 20-400, 20-300, 20-200, 20-100, 20-50, or 20-25 nucleotides. In some embodiments, a barcoded nucleic acid has a length of 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450, or 500 nucleotides. In some embodiments, a barcoded nucleic acid may be longer than 1000 nucleotides.

A barcoded nucleic acid, in some embodiments, may further include a primer domain and/or an anchor domain that are complementary to one of the anchor domains of a chain oligo. A barcoded nucleic acid may be linked to or serve as a means to identify any biomolecule, as discussed below. The 3' end of a barcoded nucleic acid, in this example, may include an anchor domain that that is complementary to one 3' end of a chain oligo such that the two anchor domains bind to each other to form a paired domain. Anchor domains may be single-stranded, double-stranded, or partially double-stranded (containing a single-stranded and double-stranded nucleic acid). Barcoded nucleic acids may include a single-stranded anchor domain. An anchor domain may be added to, or may be a component of, a barcoded nucleic acid or a target biomolecule of interest.

Anchor domains, in some embodiments, are used for identifying or localizing a target biomolecule(s) of interest. When co-localizing two biomolecules, one of the biomolecules contains an anchor domain complementary to one of the anchor domains of a chain oligo, and the other biomolecule contains an anchor domain complementary to the other of the anchor domains of a whip molecule. When a chain oligo is used in combination with a barcoded nucleic acid linked to a target biomolecule, typically the barcoded nucleic acid contains an anchor domain complementary to one anchor domain of the chain oligo, and another biomolecule contains an anchor domain complementary to the other anchor domain of the chain oligo.

Linking of Oligonucleotides

As noted above, the methods disclosed herein can be used to link smaller oligonucleotide fragments originating from a single larger oligonucleotide. To avoid unwanted linkage between fragments, for example by fragments originating from different large oligonucleotides, individual oligonucleotides may first be isolated in individual discrete volumes prior to fragmentation. Fragmentation of oligonucleotides in individual discrete volumes may be accomplished using known methods in art. In certain example embodiments, fragmentation of oligonucleotides is accomplished using tagmentation.

An "individual discrete volume" is a discrete volume or discrete space, such as a container, receptacle, or other arbitrary defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electromagnetic, or light illumination, or any combination thereof that can contain a target molecule and a indexable nucleic acid identifier (for example nucleic acid barcode). By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electromagnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents may be passed in or through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others.

In certain embodiments, the compartment is an aqueous droplet in a water-in-oil emulsion. Said droplets may be formed using microfluidic devices according to known techniques in the art. Other methods for generating droplets as described herein may be used as appropriate, including, but not limited to, high speed vortex, ultrasonic waves, extrusion, filtering, microsieve chips, or the like. Individual oligonucleotides may be loaded into separate droplets according to known methods in the art.

In some embodiments, the invention provides a nucleic acid assembly method based on the technology described herein, wherein individual discrete containers or droplets are not required. This would enable a "one-pot" approach for performing the reactions described herein. For example, one or more chain oligos as described herein may be used to capture via PCR, two distinct, distal segments of DNA by having each arm of the chain oligo specific to a different target DNA, such that after PCR, they would then be joined by the chain oligo. This would allow linking of any number of nucleic acid sequences in "daisy chain" fashion, wherein multiple DNA segments may be held together or joined by chain oligos at each intersection. Once the individual DNA segments have been amplified and joined, a transposase may then be used to excise the intervening chain oligo, which would also contain recognition sequences for the transposase. The resulting products would be "scarless" assemblies of the DNA segments targeted by the chain oligos. In some embodiments, this could be done in a "one-pot" assembly. In other embodiments, such methods may be performed either with custom unique barcodes on adapters for each fragment, or by creating primers to match "natural" or native sequences of the particular nucleic acid. In addition, each chain oligo may be specifically designed to a particular genomic sequence. Alternatively, generic adaptors may also be used. Such methods may be useful for any application, including, but not limited to, synthetic biology methods, Golden Gate technologies, assembly of genes, assembly of entire genomes, cloning, or plasmid assembly. One particular advantage for such methods is that it is only necessary to perform several short PCRs, rather than long-range PCR, thereby eliminating the possibility of amplification error. One of skill in the art will be able to identify useful and appropriate applications in accordance with the invention.

In certain example embodiments, the individual discrete volume is a section of a thin capillary tube. For example, in some embodiments, alternative emulsion containers may be used, such as nano-particle hollow containers that act as capillaries (see, for example, Wang et al., "Synthesis, Properties, and Applications of Hollow Micro-/Nanostructures," Chemical Reviews 116(18):10983-11060, 2016).

Figure 4:
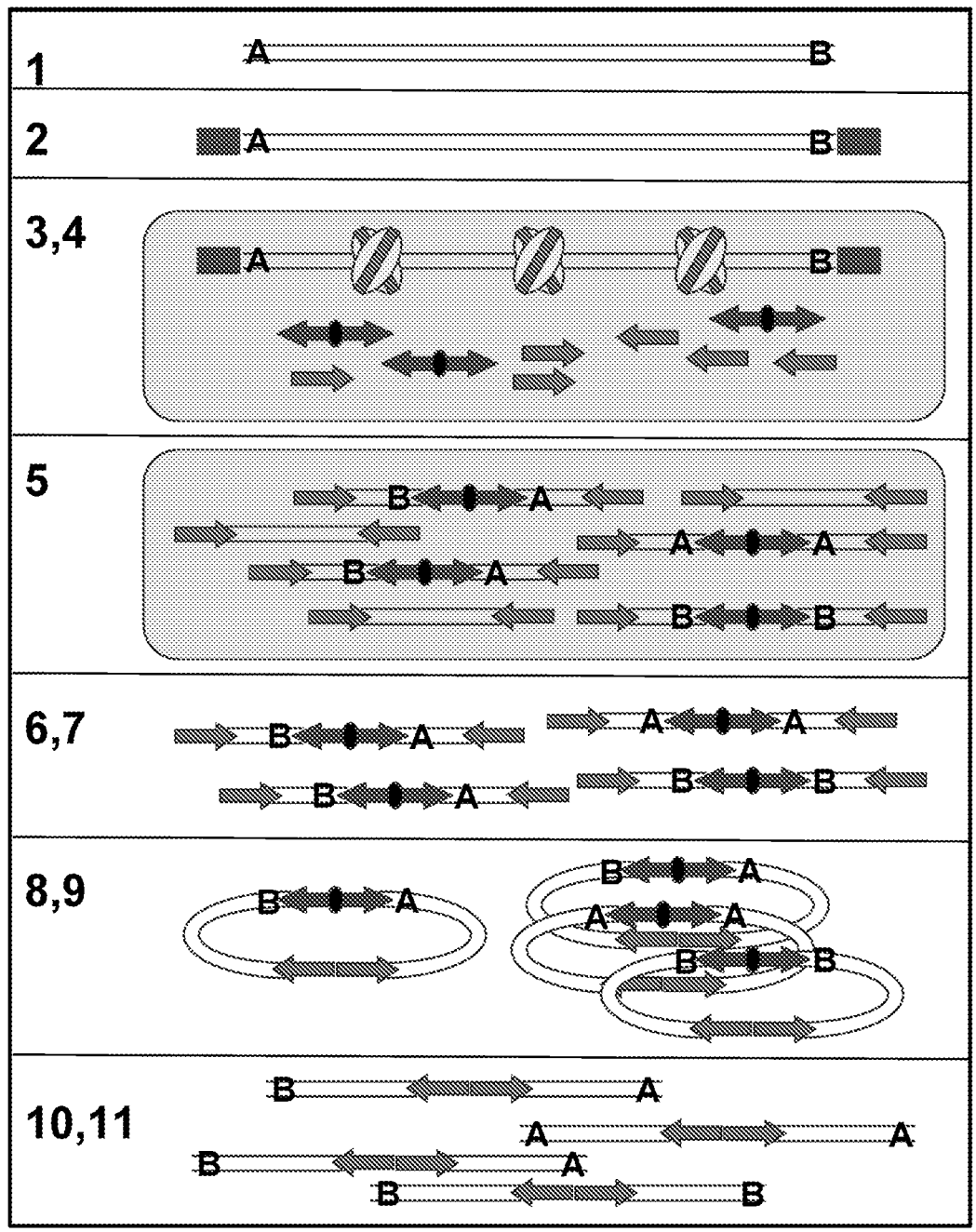
FIG. 4 shows a representation of the chain-seq technique as described herein. Step 1 shows template DNA, greater than 15 kb in length. Step 2 shows ligation of the outside adaptor (OA). Step 3 shows incorporation of the template DNA into emulsion droplets. Step 4 shows transposition to insert the internal adaptor (IA) into the template DNA. Step 5 shows whip-PCR or chain-PCR. Step 6 shows breaking of the emulsion droplets. Step 7 shows pull-down of the PCR-amplified DNA fragments using biotin. Step 8 shows circularization of the PCR-amplified DNA fragments. Step 9 shows removal of the uncircularized DNA fragments. Step 10 shows PCR to generate a library of DNA fragments. Step 11 shows removal of the chain outside adaptors.

Turning now to FIG. 4, an example embodiment is described in detail. In some particular embodiments, individual template DNA molecules may be encapsulated into droplets, and transposomes may be prepared to contain an internal adaptor. The transposomes may then be used to insert the internal adaptor into the encapsulated template DNA by incubation. The reactions may be incubated at 37° C. for 2 hr, or at 55° C. for 15 min. Other incubations times and/or temperatures may also be used in accordance with the invention as appropriate. The droplets may then be incubated at 95° C. for 10 minutes, to denature the transposase and break the interaction between transposase and the template DNA (FIG. 4, steps 3 and 4).

To accomplish this step, the reaction buffer may be optimized to be compatible with transposome insertion and/or PCR. In some embodiments described herein, various buffers, polymerases, conditions for transposome insertion and denaturing, and PCR amplification protocols may be used, as would be recognized by one of skill in the art. A buffer may be optimized in order to increase the efficiency of transposome insertion. The buffer components may also be adjusted using different polymerases and PCR protocols to identify conditions that produce reliable chain-PCR products.

As described above, a transposome may be synthesized or prepared to comprise an internal adaptor. An internal adaptor may be any size appropriate for use with the invention, and as appropriate for the particular application. For example, an internal adaptor may be 10-100 bp, including 10 bp, 15 bp, 20 bp, 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, or the like. An internal adaptor may also include a mosaic end. Similar to the internal adaptor, a mosaic end may be any size as described above. In addition, such elements may be artificial sequence or may be naturally occurring. One of skill in the art will recognize that internal adaptors smaller or larger than described herein may be appropriate for use in accordance with the invention. A mosaic end as described herein may be specifically recognized by a transposase, such as a Tn5 transposase, and may be included in order to provide additional length or sequence to the internal adaptor or for use in further embodiments of the invention, such as PCR.

In accordance with the invention, transposomes may be used for insertion of an internal adaptor or a mosaic end, or both, into a template DNA molecule. In some embodiments, the transposome is part of the reaction buffer for PCR in an emulsion droplet as described herein. In other embodiments, the methods described herein take place without breaking or disruption of the emulsion droplets.

In specific embodiments of the invention, transposases may be denatured and dissociated from DNA after addition of the internal adaptor or mosaic end, or both, into the template DNA. In accordance with the invention, chain-PCR may be performed subsequent to transposome activity in order to link and amplify the outside adaptor-ligated ends of the template DNA. To accomplish this step, the reaction buffer may be optimized to be compatible with both transposome insertion and subsequent PCR. Various buffers, polymerases, conditions for transposome insertion and denaturing, and PCR amplification protocols may be appropriate and useful as described herein.

After insertion of an internal adaptor into a template DNA using a transposase, chain-PCR may then be performed to link and amplify the outside adaptor-ligated ends of the template DNA. In some embodiments, suppression chain-PCR, using internal adaptor (IA) oligos and a limited amount of chain-oligos, may be used in order to minimize IA-IA product (FIG. 4, step 5).

After transposome insertion, one or more IA-spacer-IA segments may be inserted into the encapsulated template DNA. Thus, DNA amplified from internal DNA regions ("internal PCR products") may have an IA at both ends, while DNA amplified from the end regions of the template DNA ("end PCR products") may have an IA at one end and an OA at the other end. As described in the Examples, the IA used was 34 bp, and the OA had no complementary sequence with the IA. Thus, "internal PCR products" had 34 bp of IA sequence at both ends.

In some specific embodiments, after denaturing, the ends of single-stranded DNA from "internal PCR products" may anneal with each other and prevent the binding of IA oligos. By adjusting the annealing temperature of PCR, the production of "end PCR products" may be favored, and the production of "internal PCR products" may be minimized. In accordance with the invention, using a limited amount of chain-oligos may maximize the yield of two-ends chain-PCR products, and minimize free chain-oligos and one-end products. In addition, a limited amount of chain-oligos may be used when making emulsion droplets.

In some embodiments, 15-20 cycles of PCR amplification may be used in order to incorporate all chain-oligos into "ends PCR products." One of skill in the art will recognize that other conditions may be used in accordance with the invention. "Ends PCR products" may have two arms, in which each arm represents one end of the template DNA, with the chain-oligo in between the two ends. The ends of the "ends PCR products" may be the IAs, which were inserted into the template DNA molecule.

In some embodiments, emulsion droplets may then be broken according to the emulsion droplet oil phase components (FIG. 4, step 6). DNA may then be purified accordingly using compatible silicon-based column or DNA precipitation.

In further embodiments, "ends PCR products" contain incorporated chain-oligos, which may have been engineered to carry a desthiobiotin label. Streptavidin beads, for example Dynabeads M-280 Streptavidin from Thermo Fisher Scientific, were used to pull down "ends PCR products," while the "internal PCR products" were washed away. The "ends PCR products" were then eluted using biotin, which has higher affinity to streptavidin than desthiobiotin (FIG. 4, step 7).

Eluted "ends PCR products" were circularized using T4 DNA ligase following the blunt end ligation protocol (FIG. 4, step 8). The circularized products have two IAs at the ligated junction, which serves as a marker in the sequencing data analysis.

Figure 7:
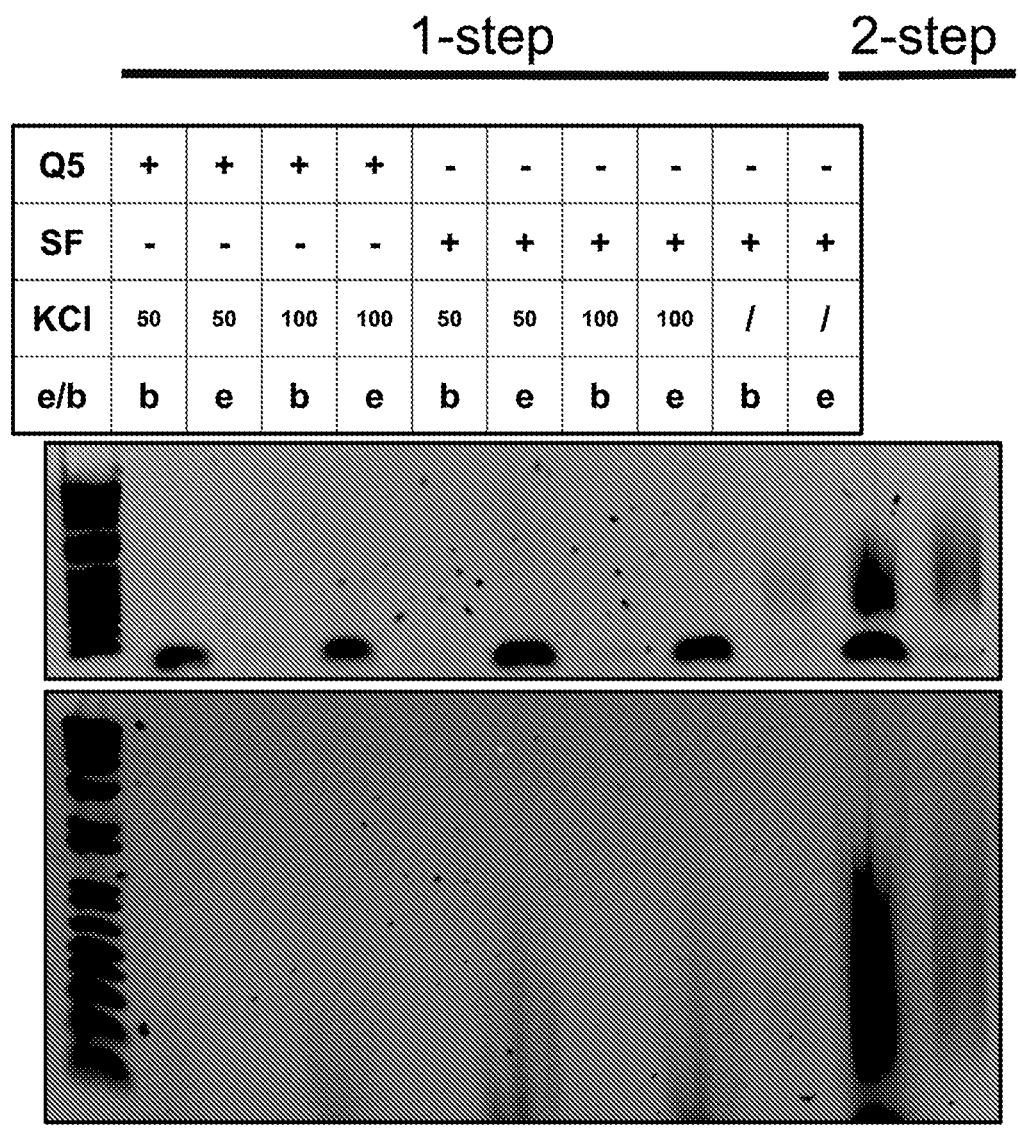
FIG. 7 shows results of integration of transposome insertion and PCR in emulsion.

For T7 DNA, PCR was used to check the size distribution of products, shown in FIG. 7. The ends of the template DNA, which could be any combination of the head end and the tail end, were now physically closer to each other on the DNA sequence (FIG. 4, step 10). Primers targeting the ends of T7 DNA were used to perform PCR. Intact T7 DNA was used as a control template, which produced a 40-kb linear DNA amplicon. Successful chain-seq produced a smear of DNA products ranging from approximately 150 bp to several kb.

ExoV was used to digest uncircularized DNA, and PCR was performed to amplify the products. Primers were used that annealed to the OA to amplify the end-joined products. The chain-OA was then removed using SapI digestion and DNA purification.

Figure 5:
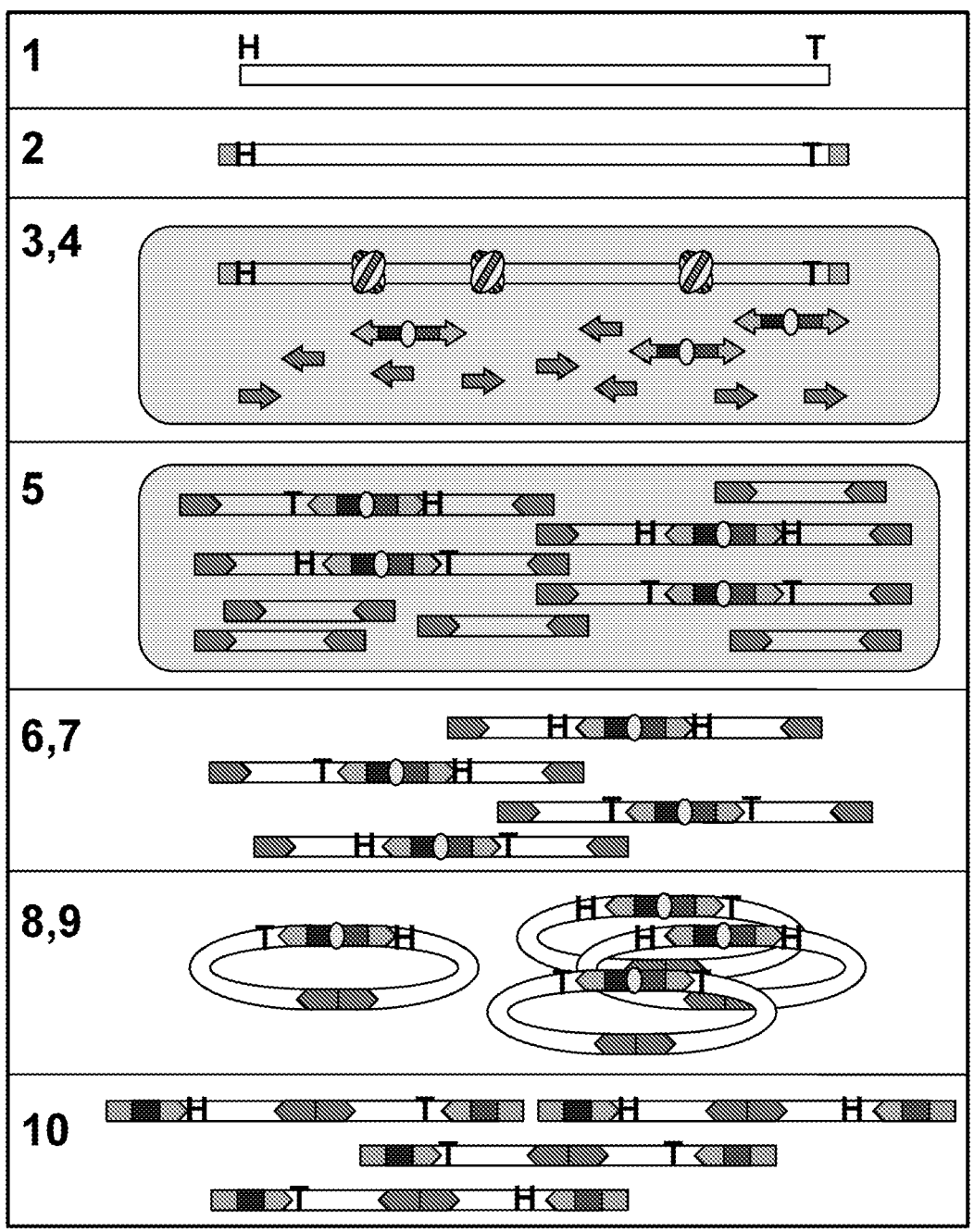
FIG. 5 shows a representation of the chain-seq technique as described herein. Step 1 shows template DNA, greater than 15 kb in length. Step 2 shows ligation of the outside adaptor (OA). Step 3 shows incorporation of the template DNA into emulsion droplets. Step 4 shows transposition to insert the internal adaptor (IA) into the template DNA. Step 5 shows whip-PCR or chain-PCR. Step 6 shows breaking of the emulsion droplets. Step 7 shows pull-down of the PCR-amplified DNA fragments using biotin. Step 8 shows circularization of the PCR-amplified DNA fragments. Step 9 shows removal of the uncircularized DNA fragments. Step 10 shows PCR to generate a library of DNA fragments.
Figure 5:
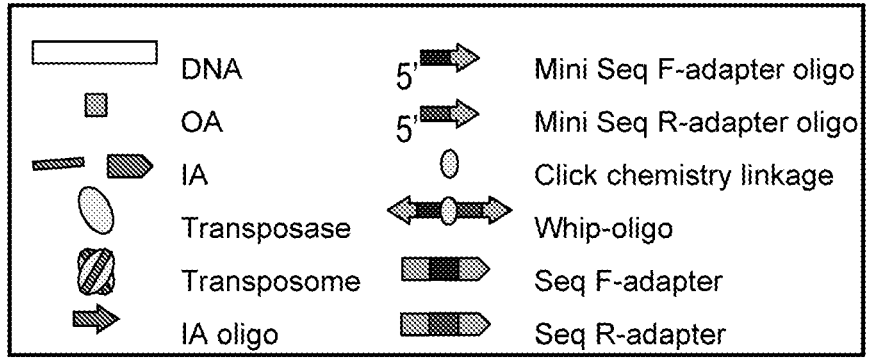

FIG. 5 provides an alternative embodiment wherein sequencing adaptors may be directly incorporated into the chain oligos. Such an alternative provides a means to streamline the process for sequencing purposes.

Long Range DNA Sequencing

Long range DNA sequencing is essential for many genomic studies, including de novo genome assembly, long range mutation detection, genomic repeats mapping, and highly similar synthetic biology constructs verification. See Gnerre et al. ("High-quality draft assemblies of mammalian genomes from massively parallel sequence data," PNAS 108(4):1513-1518, 2011) for a description of genome assembly methodology. Currently, there are two basic strategies to acquire long DNA sequencing results.

The first strategy is to make traditional jumping library, which relies on the circularization of the template DNA. Constructs with highly repetitive or similar elements require this step in order to resolve the order and orientation of sequences, which involves the circularization of long 3-8 kb molecules or cloning-based libraries using phage packaging to span 40 kb, a laborious and expensive process. Although the cost of sequencing has dropped dramatically during the past few years while the cost of construction of jumping libraries has not. In addition, due to the low yield, the starting material is high. Furthermore, the efficiency of circularization, the key step of building a jumping library, on DNA larger than 5 kb is dramatically low.

The second strategy is to use some long-read next generation sequencing technologies, like those from PacBio and Oxford Nanopore. But both platforms have much higher error rates than Illumina sequencing.

There are also some alternative strategies available. For example, Illumina's TruSeq Synthetic Long-Read DNA Library Prep Kit for Genome Assembly is claimed being capable of sequencing up to 10 kb DNA. But it relies on DNA barcoding and using proprietary informatics.

The present invention provides a more efficient method that is capable of replacing the jumping library, PacBio, and Oxford Nanopore methodologies. In some embodiments, any two or more nucleic acid molecules may be joined together using the chain oligos and methods described herein.

Screening Applications

One specific application of chain oligos is screening of a biological sample for a desired molecule. Examples of this include T-cell and B-cell receptor profiling, in which one or more chain oligos may be used to screen a population of nucleic acids to identify a particular desired cell type or clonotype.

In one example embodiment, a chain oligo as described herein may be designed to screen a population of RNA molecules to identify one or more RNA molecules of interest. In accordance with the invention, a chain oligo may be designed to recognize and hybridize to such RNA sequence(s). In some particular embodiments, more than one particular RNA molecule or sequence may be captured at once.

In some embodiments, a chain oligo may be designed to recognize two distinct RNA molecules. Such an oligo may have two arms, wherein one arm has a recognition sequence for the first RNA molecule, and the second arm has a recognition sequence for the second RNA molecule. In some embodiments, a biological sample may be obtained from a particular individual for which screening is necessary. A chain oligo may be designed with a sequence on one arm to recognize a particular RNA molecule, and a sequence on the other arm that recognizes a second, distinct RNA molecule. Each arm of the chain oligo therefore hybridizes to a separate RNA molecule. Reverse transcription may then be performed using appropriate reaction conditions and reagents in order to produce cDNA of both the first and the second RNA molecules. Such methods may be performed in droplets as described herein in some embodiments. In other embodiments, both 3' ends of the chain oligo may serve as primer molecules for first-strand cDNA synthesis according to methods known in the art. Second strand synthesis may then be performed using a second, distinct chain oligo. In particular, the newly produced cDNA may be dissociated from the template RNA molecules and the second, distinct chain oligo may hybridize to the 3' ends of the cDNA than the first chain oligo and second strand synthesis as known in the art may be performed in order to produce a double-stranded DNA copy of the starting RNA molecule.

As described herein, an appropriate reaction buffer may be optimized by one of skill in the art. In some embodiments described herein, various buffers, polymerases, and amplification protocols may be used, as would be recognized by one of skill in the art. In some embodiments, 15-20 cycles of PCR amplification may be used in order to produce a desired amount of cDNA. One of skill in the art will recognize that other conditions may be used in accordance with the invention.

In some embodiments, emulsion droplets may then be broken following PCR, and cDNA may then be purified accordingly using compatible silicon-based column or DNA precipitation.

In further embodiments, chain-oligos may be engineered to carry a desthiobiotin or other appropriate label. Streptavidin beads, for example Dynabeads M-280 Streptavidin from Thermo Fisher Scientific, may be used to pull down desired cDNA. The pulled down products may then be eluted using, for example, biotin, and eluted cDNA may be circularized for sequencing data analysis.

Screening techniques based on chain oligos may also be useful in cancer screening, in which multiple can oligos may be used simultaneously to identify multiple biomarkers. For example, two or more chain oligos may be used to link together two or more RNA molecules. For example, a first chain oligo may be hybridized to a first RNA molecule, wherein the first 3' end of the first chain oligo hybridizes to the first RNA molecule and the second 3' end of the first chain oligo hybridizes to a second RNA molecule; a second chain oligo may be hybridized to a second RNA molecule, wherein the first 3' end of the second chain oligo hybridizes to the second RNA molecule and the second 3' end of the second chain oligo hybridizes to a third RNA molecule; a third chain oligo may be hybridized to a third RNA molecule, wherein the first 3' end of the third chain oligo hybridizes to the third RNA molecule and the second 3' end of the third chain oligo hybridizes to the first RNA molecule, such that a circular nucleic acid molecule is formed by the hybridization of the first, second, and third RNA molecules and the first, second, and third chain oligos as shown in FIG. 2. First and second strand cDNA synthesis may be performed as known in the art and as described herein above. In some embodiments, a circular nucleic acid is produced as shown in FIG. 2. Subsequent amplification cycles may be performed in order to produce a desired number of copies of cDNA for detection of, for example, mutations present in cancer cells. In some embodiments, one or more restriction endonucleases may be employed to cut the amplified cDNA for further analysis. Additional details of these applications are provided below.

T-Cell and B-Cell Receptor Profiling

In humans and closely related species, cellular immunity is mediated by T cells (or T lymphocytes), which participate directly in the detection and neutralization of pathogenic threats. Essential to T-cell function are highly specialized extracellular receptors (T-cell receptors or TCRs) that selectively bind specific antigens displayed by major histocompatibility complex (MHC) molecules on the surface of antigen-presenting cells (APCs). Antigen recognition by TCRs activates T cells, causing them to proliferate rapidly and mount immune responses through the release of cytokines.

Given the relative specificity of TCR-antigen interactions, a tremendous diversity of TCRs are required to recognize the wide assortment of pathogenic agents one might encounter. To this end, the adaptive immune system has evolved a system for somatic diversification of TCRs that is unrivaled in all of biology. The vast majority of TCRs are heterodimers composed of two distinct subunit chains (α- and β-), which both contain variable domains and, in humans, are encoded by single-copy genes. The term "clonotype" is typically used to refer either to a particular TCR variant (TCR-α or TCR-β subunit), or to a particular pairing of TCR subunit variants (TCR-α+TCR-β) shared among a clonal population of T cells.

The state of arts for T-cell clonotype with pairing of TCR subunit variants (TCR-α+TCR-β) is using cell-based emulsion overlap-extension RT-PCR technique (Turchaninova et al., Eur J Immunol 43:2507-15, 2013). But there are critical shortcomings in this method. (1) It relies on blocker oligos to inhibit unfused molecule amplification, and can only use DNA polymerase without 3' to 5' exonuclease activity, like Taq polymerase, instead of any high fidelity polymerase. Otherwise, the blocker oligos will be degraded. Therefore, the final sequencing results will contain many artificial sequencing errors introduced by low fidelity polymerase. (2) Some of the unfused molecules from different cells are possibly fused and amplified with each other in the nested PCR step after breaking emulsion and pooled the molecules in bulk.

Using chain-oligos as described herein, these shortcomings can be overcome and accuracy and efficiency can be significantly increased. For example, for any specific clonotyped T-cell, specifically designed chain-oligos can be used to amplify and clone the coding sequences of TCR-α and TCR-β. Once sequenced, the coding sequences of TCR-α and TCR-β can in turn be cloned into B-cells. Chain-oligos may be designed that are specific to, for example, the constant regions in α-chain mRNAs, such as the 5' untranslated region (UTR) and "constant" (C) segment coding region, or to the constant regions in β-chain mRNAs. Following chain-Seq PCR as described in the Examples, the coding regions of the α- and β-chains that encode "variable" (V) and "joining" (J) segments may be linked using the methods described herein.

Furthermore, two chain-oligos can be used to isolate and/or amplify even longer sequences for sequencing. After a single chain-oligo grabs a pair of particular DNA sequences, only around 300 bp of nucleic acid sequence can be sequenced using an Illumina platform. However, using two compatible chain-oligos, two separate sequenceable molecules can be produced, allowing sequencing of twice the length of nucleic acid, i.e., 300+300 bp.

In some embodiments, the invention provides a diagnostic method to capture heavy and light chain transcripts of B-cells or TCR-α and TCR-β sequences wherein no adaptor is required. In such a case, one or more chain oligos may directly link the transcript pair via PCR. Such a method may only require isolation of a cell either in a container or spatially on a surface. In this case each chain oligo contains a primer pair corresponding to a conserved framework in, for example, the heavy (H) or light (L) chains of an antibody sequence, which can then extend and capture the full-length chain information. To ensure that each chain oligo contains H and L pairing, a cell or container barcode may be added to identify single cells or samples. In some embodiments, this could be performed in emulsion to ensure single-cell copies or in situ, such as within agarose, in a method similar to polymerase colonies (i.e., "polonies"). Such methods would enable very cost-effective preparation of single-cell resolution immune cell profiles, or the pairing of any transcript set of interest. In some embodiments, the B cell or T cell of interest can be isolated from a subject with a recent infection or with a vaccine administration.

In other embodiments, chain oligos as described herein may be used to produce an antibody of any combination of components, such as H and L chains. Any number of coding regions for antibody components may be joined together in any configuration using any number of chain oligos to link the nucleic acid sequences together. In a particular embodiment, once such nucleic acids are joined together using chain oligos, the chain oligos themselves may then be removed or excised from the joined complex using specific transposases, including, but not limited to a piggyback transposase, in order to remove the chain oligo such that there is no "scar" left in the joined nucleic acid complex. The resulting nucleic acid complex may then be introduced into a B-cell in order to produce a specific desired antibody. The present invention, therefore, enables the production of engineered antibodies having any desired sequence.

Detection of Polymorphism or Multiple Mutations in Single Cells

One or more chain-oligos may be used to target multiple specific genomic regions or multiple mRNAs in a single cell, which can enable detection of the presence of certain mRNAs or mutation combinations or polymorphism or profile single cells using sequencing. The detection of such polymorphism or mutations can be used in genotyping or cancer diagnostics. Profiling or detection of presentation of two or more specific mutations can be performed in a single cell, such as a cancer cell.

For RNA, chain oligos may be used to profile or detect two or more specific RNA molecules or RNA transcripts. Such oligos may be designed to specifically reverse transcribe, amplify, and link the resulting cDNA fragment converted from the target RNAs.

Kits

The invention further provides reagents and kits comprising one or more such reagents or components for use in a variety of assays, including for example, nucleic acid assays, e.g., an assay described herein. Such kits may preferably include at least a first chain oligo as described herein, and means for detecting or visualizing amplification of a target sequence. In some embodiments, such a kit may contain multiple chain oligos as described herein for the purpose of performing PCR or sequencing. Chain oligos may be provided in lyophilized, desiccated, or dried form, or may be provided in an aqueous solution or other liquid media appropriate for use in accordance with the invention.

Kits may also include additional reagents, e.g., PCR components, such as salts including $MgCl_2$, a polymerase enzyme, and deoxyribonucleotides, and the like, reagents for DNA isolation or sequencing, as described herein. Such reagents or components are well known in the art. Where appropriate, reagents included with such a kit may be provided either in the same container or media as the chain oligo or plurality chain oligos, or may alternatively be placed in a second or additional distinct container into which the additional composition or reagents may be placed and suitably aliquoted. Alternatively, reagents may be provided in a single container means.

Embodiments disclosed herein provide methods, primers, and kits for covalently linking polynucleotides which has application in, for example, de novo genome assembly, long range mutation detection, mapping of repeating regions, and synthetic biology construct validation. In particular, the embodiments disclosed herein are well adapted for applications requiring the manipulation and/or sequencing of large polynucleotide molecules. Existing techniques are costly, require large DNA inputs, suffer from error rates much higher than sequencing shorter reads, are typically much less efficient once the size of DNA exceeds 5 kb.

The invention is further described in the following examples, which do not limit the scope of the invention described in the claims.

EXAMPLES

Example 1—Development and Optimization of Chain-Seq Technique for Long DNA Sequencing Using T7 Phage DNA (40 kb Linear)

Version 1, without Built-in Sequencing Adapter, Compatible with any Sequencing Platform Outside Adaptor (OA)

The outside adaptor contains two Chi sites and a rare cut site (SapI). The Chi sites are included at the ends of the OA in order to provide protection of the ends of linear DNA from exonuclease V (RecBCD) digestion. Other end protection methods can be used, such as a hairpin. The SapI restriction enzyme recognizes a 7-bp sequence (one cut out of 16,384 bp of random DNA sequence) and cuts outside of recognition site. The SapI site was used to remove the OA before making a sequencing library. Other restriction enzyme sites may also be used to replace SapI.

The SapI recognition and cutting site was as follows:

(SEQ. ID. NO: 1)
GCTCTTCN^

(SEQ. ID. NO: 2)
CGAGAAGNNNN^

Chain Oligos

Chain oligos were linked using Copper(I)-Catalyzed Azide-Alkyne Cycloaddition (CuAAC) click chemistry reaction. Other click chemistry reactions, such as copper-free strain-promoted azide-alkyne cycloaddition (SPAAC) reaction, or other chemical reactions, such as the thiol-ene reaction, may be used, along with others known in the art.

The azide (AZ)-chain oligo contained the following components: AZ-Desthiobiotin-Chi-Chi-SapI. Desthiobiotin is a modified form of biotin that binds less tightly to avidin and streptavidin than biotin, while still providing excellent specificity in affinity purification methods. Desthiobiotin can be released from streptavidin with biotin. Biotin can also be used to replace desthiobiotin. The alkye (AK)-chain oligo contained the following components: AK-Desthiobiotin-Chi-Chi-SapI. The AZ-chain and AK-chain oligos were 5'-5'-linked as described herein, producing a chain oligo having two arms. Chain oligos may also be constructed with more than two arms, such as demonstrated in FIGS. 1 and 2. Chain oligos having two or more arms may be used to link together multiple DNA molecules for any number of applications described herein.

Internal Adapter (IA)

The internal adaptor used was 15 bp and included a mosaic end (ME). The mosaic end was 19 bp and is specifically recognized by Tn5 transposase. The 15-bp artificial sequence was included to elongate the internal adaptor and to facilitate suppression chain-PCR.

Version 2, with Built-in Illumina Sequencing Adapter, Compatible with Illumina Sequencing Platform
Outside Adapter (OA)

The outside adaptor consisted of 11 bp of common sequence from Illumina sequencing F-adapter and R-adapter, plus two Chi sites.
Chain-Oligos The AZ-chain oligo contained the following components: AZ-Desthiobiotin-Chi-Chi-SapI-F. The AK-chain oligo contained the following components: AK-Desthiobiotin-Chi-Chi-SapI-R. The AZ-chain and AK-chain oligos were 5'-5'-linked as described herein.

The SapI site can be omitted in this version of the outside adaptor, if desired. In this case, the SapI cut step was skipped and the circularized chain-PCR products were used as template to make final sequencing library.
Internal Adapter (IA)

The internal adaptor used was 15 bp and included a mosaic end. The mosaic end was 19 bp and is specifically recognized by Tn5 transposase. The 15-bp of artificial sequence was included to elongate the internal adaptor (IA) and to facilitate suppression chain-PCR.

Example 2—Method for Chain-Seq (Whip-Seq) Technique for Long DNA Sequencing Using T7 Phage DNA 1) End repair and addition of A-tails of template long DNA
2) Ligation of outside adapter (OA)
3) ExoV digestion to remove incomplete products
4) PCR to check OA ligation products
5) Click chemistry to produce chain-oligos
6) Assemble transposome
7) Combined transposome insertion and chain-PCR in emulsion droplets
   a) Generation of emulsion droplets
   b) Transposome insertion, with transposome loaded with IA
   c) Suppression chain-PCR, using IA oligos and limited amount of chain-oligos
      i) Suppression PCR to minimize IA-IA products
      ii) Limited amount of chain-oligos to maximize the yield of two-ends chain-PCR products, and minimize free chain-oligos and one-end products
8) Break emulsion
9) Pulldown chain-PCR products with built-in desthiobiotin in chain-oligos
10) Elute with biotin
11) Circularization
12) PCR to check the size distribution of products
13) ExoV digestion of uncircularized DNA
14) PCR to amplify
15) Remove chain-OA using SapI digestion
16) Library preparation
    a) Version 1: end repair, A-tailing, adapter ligation, PCR, size-selection
    b) Version 2: PCR, size-selection
17) Sequencing Detailed Method End Repair and A-Tailing of Template Long DNA—

This step is used for sequencing the ends of long DNA molecules 5-100 kb in size. The method was optimized using 40-kb T7 phage DNA. For genomic DNA, size selection may be performed, depending on the purpose of the experiment. The end repair and A-tailing steps are performed using NEBNext Ultra II kit, or other similar commercial kit, or home-made reagents.

Ligation of Outside Adapter (OA)—

The outside adaptor was ligated to the ends of the template DNA via T-A ligation using the NEBNext Ultra II kit, or other similar commercial kit. Alternatively, home-made reagents may be used.

ExoV Digestion to Remove Incomplete Products [Optional]—

Template DNA without a ligated outside adaptor at its ends may be digested using Exonuclease V (ExoV, RecBCD, from NEB).

PCR to Check Outside Adaptor Ligation—

For T7 DNA, outside adaptor ligation may be detected using primers, one annealed to the outside adaptor and one annealed to the T7 DNA at a position several hundreds of base pairs from the ends, for example.

Click Chemistry to Make Chain-Oligos—

Figure 3:
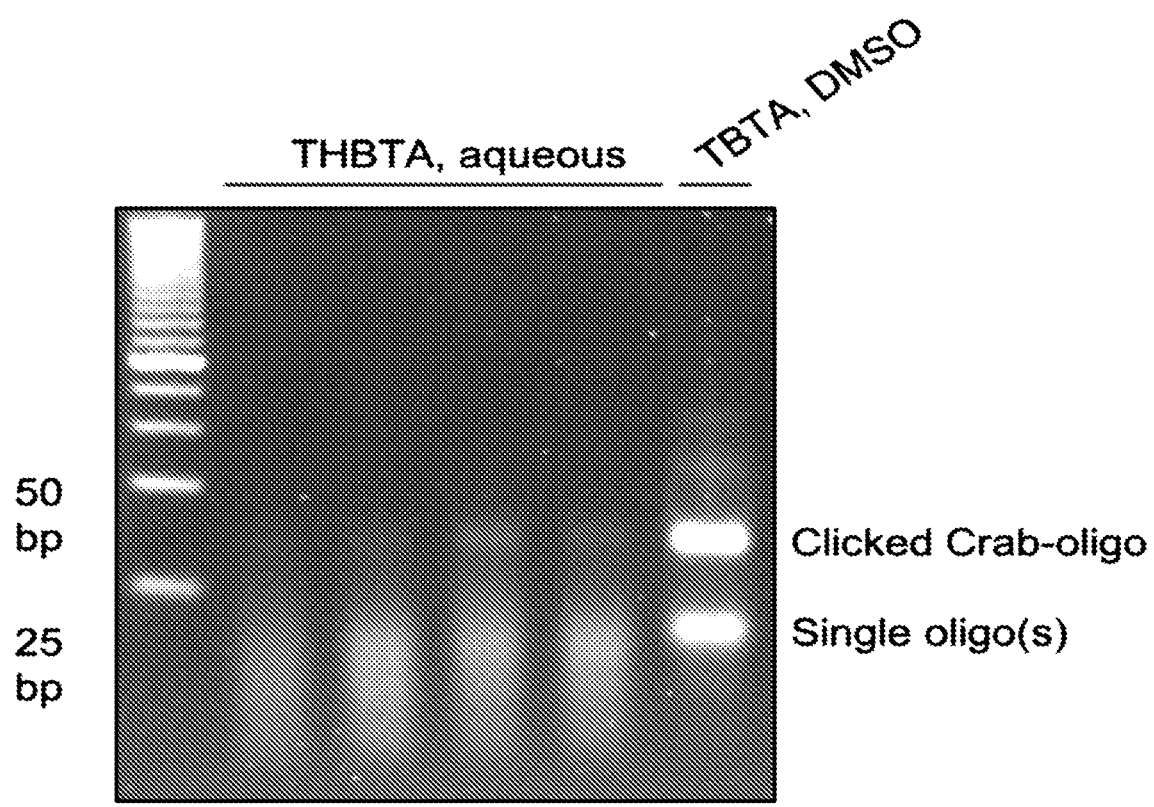
FIG. 3 shows results of click chemistry to construct chain-primers.

Copper(I)-Catalyzed Azide-Alkyne Cycloaddition (CuAAC) click chemistry reaction was used to make chain-oligos, as shown in FIG. 3. Other click chemistry reactions or other addition chemistry reactions may also be used to make chain-oligos.

Assemble Transposome—

Transposomes were assembled using Tn5 transposase and an internal adapter (IA) containing a Tn5-specific binding sequence and mosaic end. Transposomes were used to insert a known sequence, such as an internal adaptor, into the template DNA for subsequent PCR amplification. Other transposases, for example MuA, and its corresponding recognition/binding sequences, or other enzymes having similar functions, such as integrase, may also be used.

Example 3—Combined Transposon Insertion and Chain-PCR in Emulsion Droplets

The method described herein is demonstrated in FIG. 5. Single template DNA was first encapsulated into droplets, and transposomes were pre-assembled to contain the internal adaptor. The pre-assembled transposomes were then used to insert the internal adaptor into the encapsulated template DNA by incubating at 37° C. for 2 hr, or at 55° C. for 15 min. The droplets were then incubated at 95° C. for 10 minutes, to denature the transposase and break the interaction between transposase and the template DNA (FIG. 5, steps 3 and 4).

Figure 6:
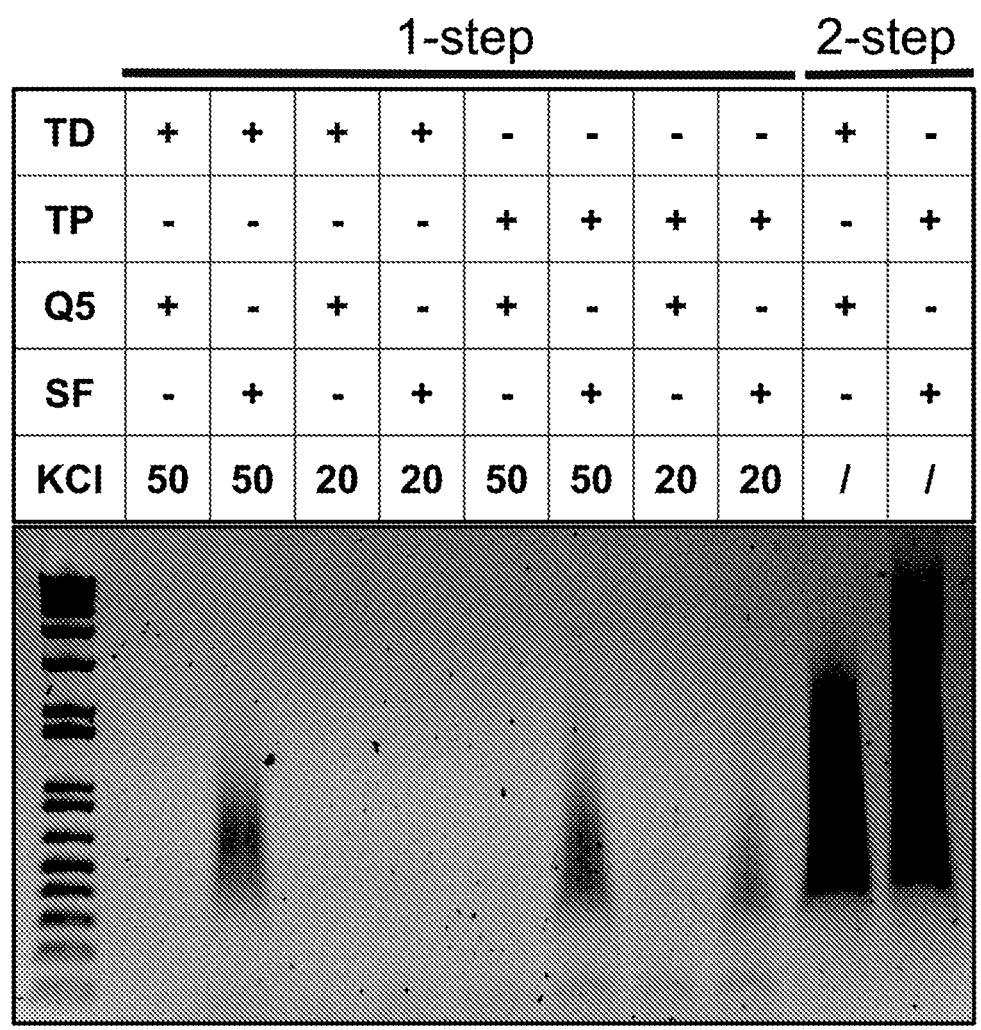
FIG. 6 shows results of integration of transposome insertion and PCR in bulk.

To accomplish this step, the reaction buffer was optimized to be compatible with both transposome insertion and PCR. Various buffers, polymerases, conditions for transposome insertion and denaturing, and PCR amplification protocols were tested. The buffer was optimized to favor transposome insertion, without which the efficiency of transposome insertion was too low. The buffer components were then adjusted using different polymerases and PCR protocols to identify conditions that would produce reliable chain-PCR products. The results of integration of transposome insertion and PCR in bulk and in emulsion are shown in FIGS. 6 and 7, respectively.

Example 4—Suppression PCR to Favor the "Ends PCR Products"

After the internal adaptor was inserted into the template DNA using transposase, chain-PCR was performed to link and amplify the outside adaptor-ligated ends of the template DNA. Suppression chain-PCR, using internal adaptor (IA)

oligos and a limited amount of chain-oligos, was used in order to minimize IA-IA product (FIG. 5, step 5).

After transposome insertion, many IA-spacer-IA segments were inserted into the encapsulated template DNA. Thus, DNA amplified from internal DNA regions ("internal PCR products") had an IA at both ends, while DNA amplified from the end regions of the template DNA ("end PCR products") had an IA at one end and an OA at the other end. The IA was 34 bp, and the OA had no complementary sequence with the IA. Thus, "internal PCR products" had 34 bp of IA sequence at both ends. After denaturing, the ends of the single stranded DNA from "internal PCR products" could annealed with each other and prevent the binding of IA oligos. Such annealing could not form between the IA and OA for the "end PCR products." Therefore, by adjusting the annealing temperature of PCR, the production of "end PCR products" was favored, and the production of "internal PCR products" was minimized. A limited amount of chain-oligos maximized the yield of two-ends chain-PCR products, and minimized free chain-oligos and one-end products. In addition, a limited amount of chain-oligos was used when making emulsion droplets.

After 15-20 cycles of PCR amplification, all chain-oligos were used and incorporated into "ends PCR products." This avoids possible cross-reaction between the ends from different template DNA after break emulsion. The success "ends PCR products" have two arms, which each arm is one end of the template DNA, and a chain-oligo in the middle, which are already incorporated into the PCR products. The ends of the "ends PCR products" are IAs.

Emulsion droplets were broken according to the emulsion droplet oil phase components (FIG. 5, step 6). DNA were purified accordingly using compatible silicon-based column or DNA precipitation.

Example 5—Biotin or Desthiobiotin to Pull Down the Chain-PCR Products of Ends Pulldown of Chain-PCR Products with Built-in Desthiobiotin in Chain-Oligos The "ends PCR products" incorporated chain-oligos, which carry desthiobiotin. Streptavidin beads, for example Dynabeads M-280 Streptavidin from Thermo Fisher Scientific, were used to pull down "ends PCR products," while the "internal PCR products" were washed away. The "ends PCR products" were then eluted using biotin, which has higher affinity to streptavidin than desthiobiotin (FIG. 5, step 7).

Example 6—Circularization of the Purified Chain-PCR Products of Ends

Eluted "ends PCR products" were circularized using T4 DNA ligase following the blunt end ligation protocol (FIG. 5, step 8). The circularized products have two IAs at the ligated junction, which serves as a marker in the sequencing data analysis.

Example 7—PCR to Verify the Size Distribution of Products

Figure 8:
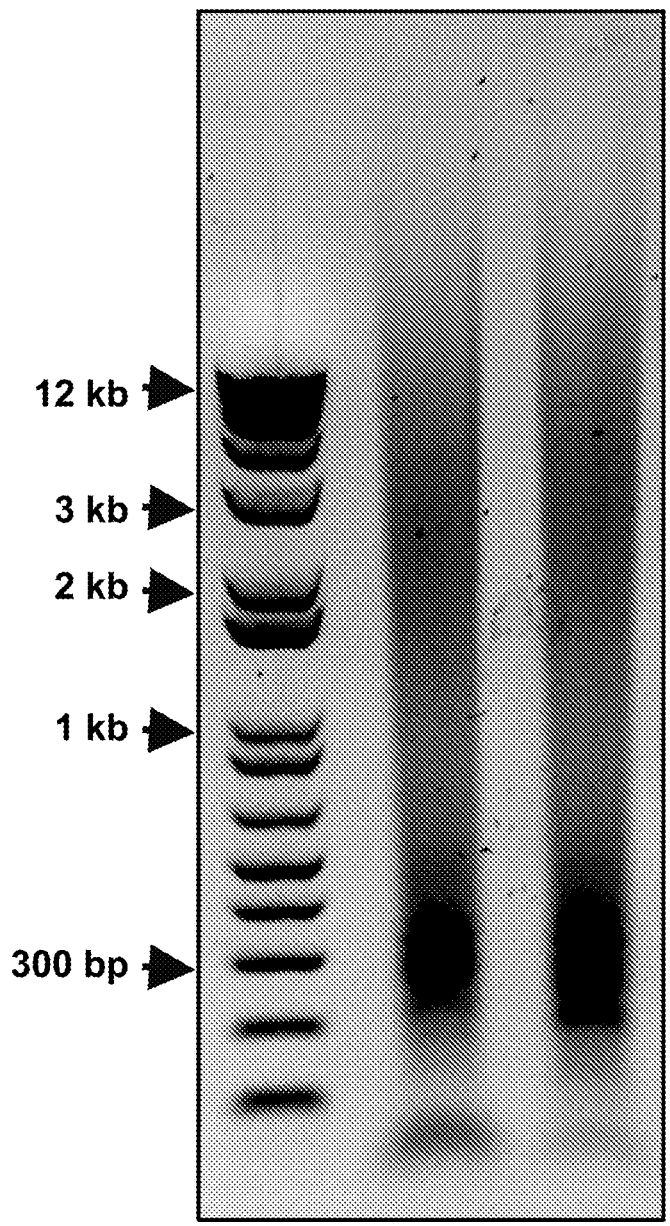
FIG. 8 shows PCR products of T7 phage DNA before library preparation.

For T7 DNA, PCR was used to check the size distribution of products, shown in FIG. 8. The ends of the template DNA, which could be any combination of the head end and the tail end, were now physically closer to each other on the DNA sequence (FIG. 5, step 10). Primers targeting the ends of T7 DNA were used to perform PCR. Intact T7 DNA was used as a control template, which produced a 40-kb linear DNA amplicon. Successful chain-seq produced a smear of DNA products ranging from approximately 150 bp to several kb.

ExoV was used to digest uncircularized DNA, and PCR was performed to amplify the products. Primers were used that annealed to the OA to amplify the end-joined products. The chain-OA was then removed using SapI digestion and DNA purification.

Figure 9:
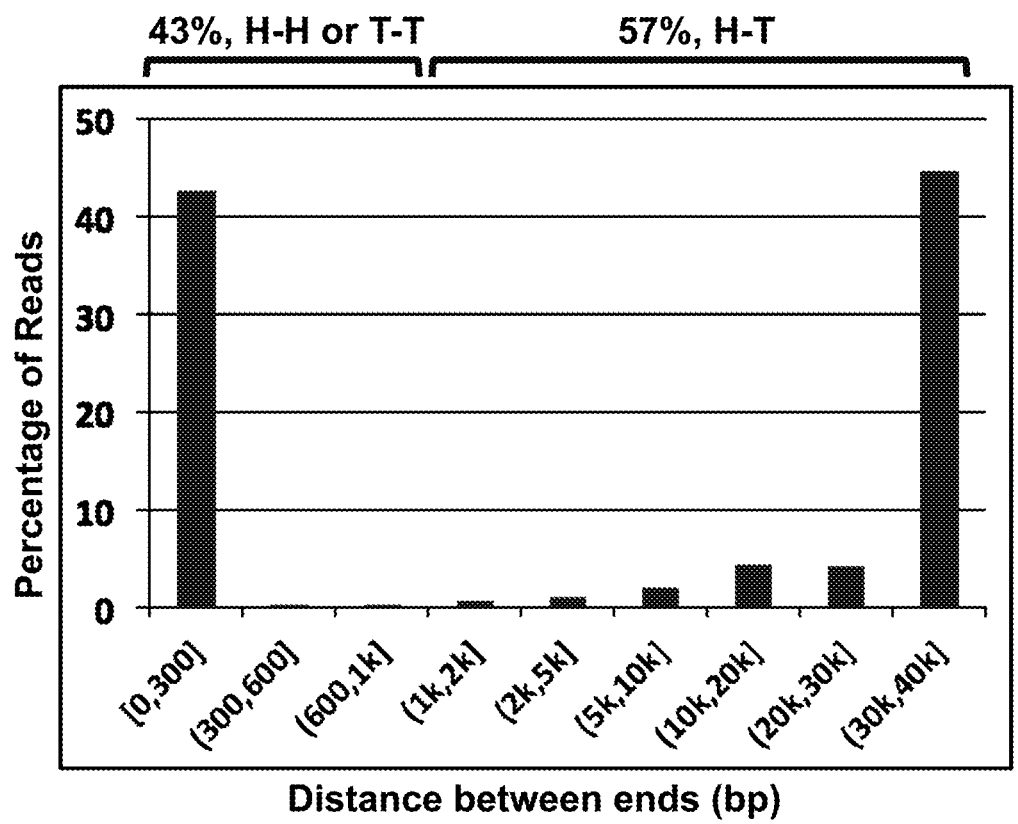
FIG. 9 shows results of sequencing of T7 DNA, indicating 43% head-head or tail-tail configuration, and 57% head-tail configuration.
Figure 10:
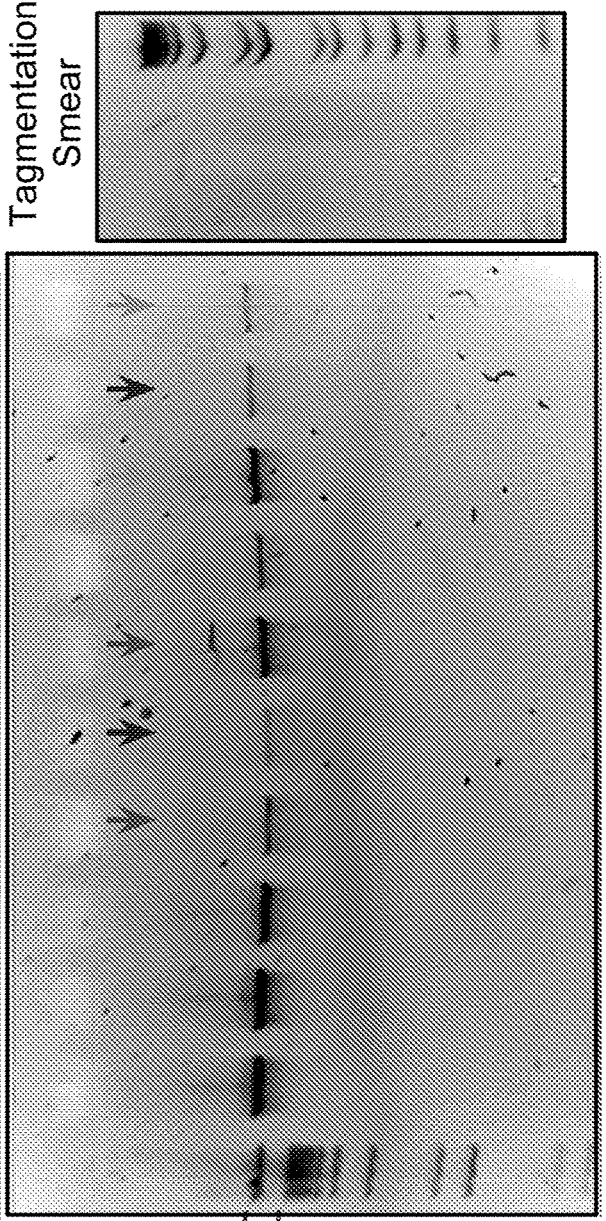
FIG. 10 shows results of "one-pot" reaction set up for optimization of tagmentation and assembly.
Figure 11:
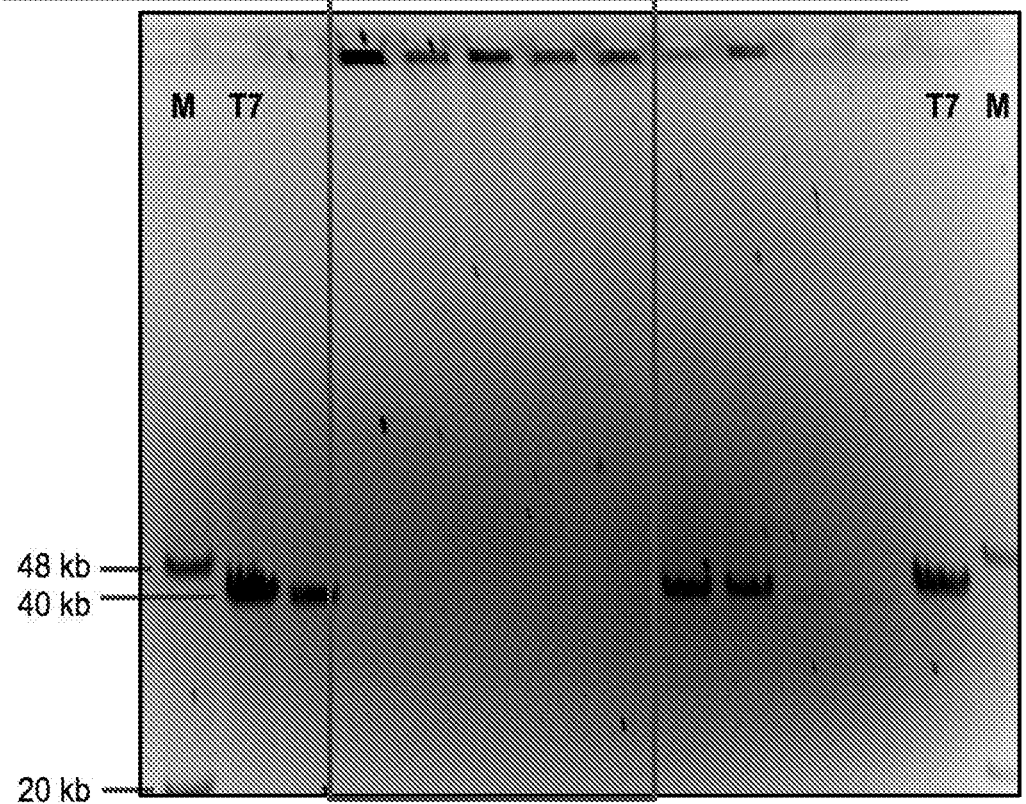
FIG. 11 shows that Tn5 transposome can tagment DNA on ice.
Figure 12:
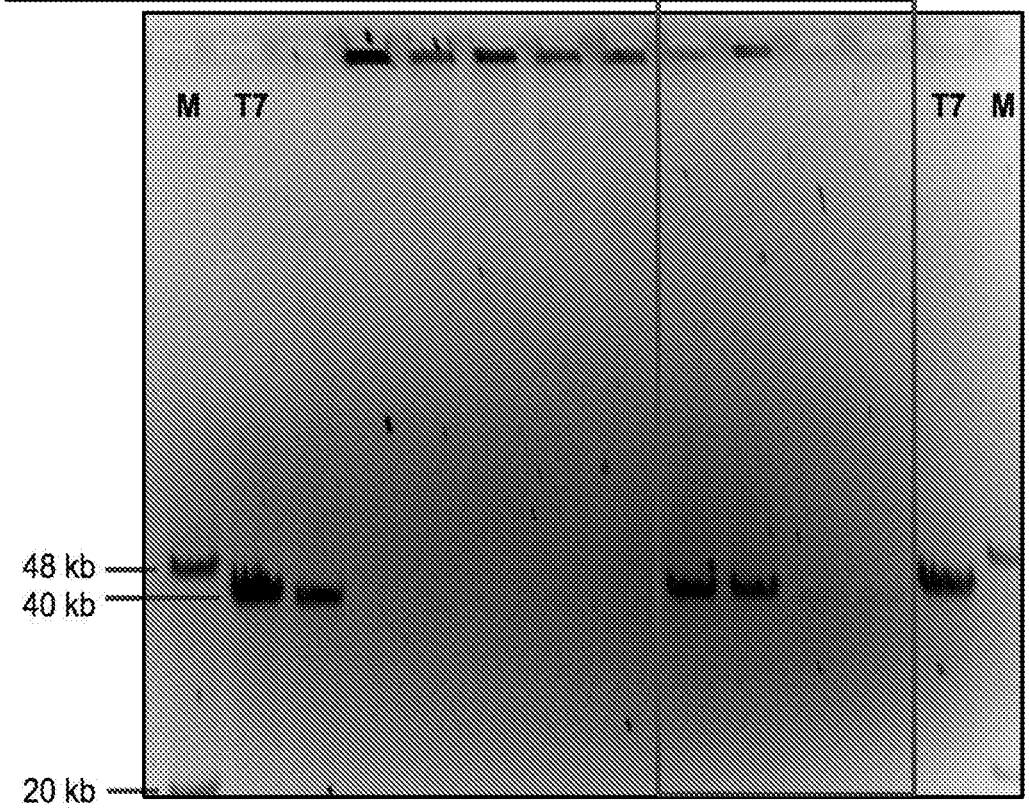
FIG. 12 shows that inactivated transposase did not bind DNA on ice.
Figure 13:
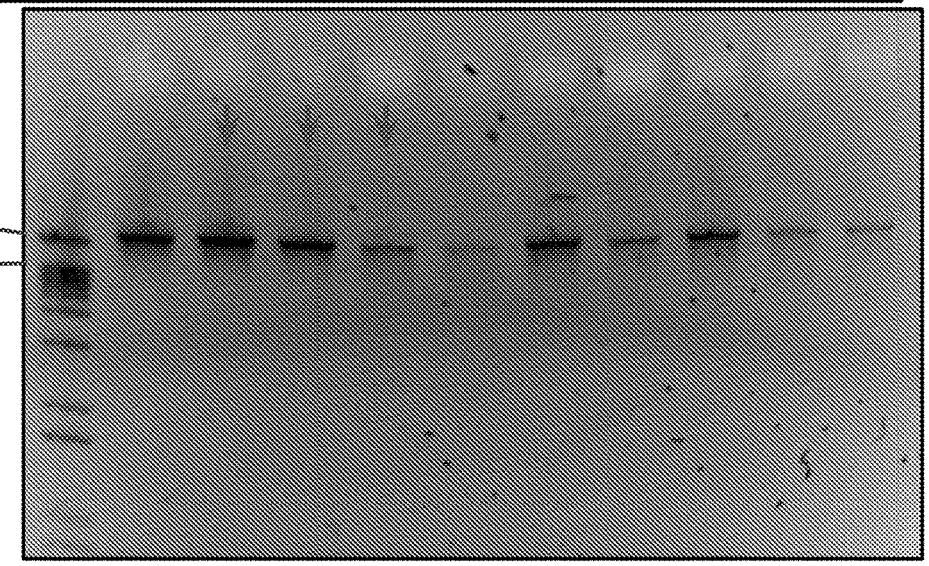
FIG. 13 shows that withholding Mg2+ can inhibit tagmentation.
Figure 14:
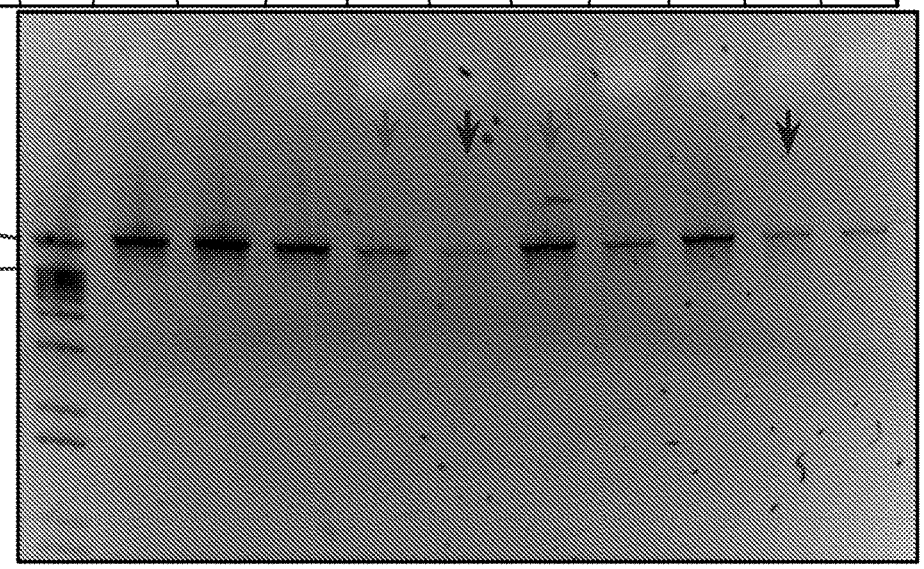
FIG. 14 shows that a temperature of −10° C. can inhibit Tn5 tagmentation.

Example 8—Removal of OA and Prepare Resulting Linear Product for Library Construction Library Preparation
Version 1: end repair, A-tailing, adapter ligation, PCR, size-selection
Version 2: PCR, size-selection
Sequencing was performed on the PCR-amplified products for a total of $2 \times 10^7$ reads, shown in Table 1 and FIG. 9.

TABLE 1

| Results of Sequencing using T7 DNA | |
| --- | --- |
| Total reads | $2 \times 10^7$ |
| Mapped both ends | $2.7 \times 10^6$ (13.4%) |
| Head-Tail | $1.53 \times 10^6$ (57.0%) |
| Head-head or tail-tail | $1.16 \times 10^6$ (43.0%) |

Example 9—Tagmentation and Polymerization Protocols

Tn5 Transposome Assembly:
25° C. for 30-60 min.
Tagmentation (if Performed Separately):
37° C. for 2 hr or 55° C. for 8-15 min.
Emulsion PCR (Integrated Tagmentation with PCR):
55° C. for 15 min (Tn5 transposome insertion)
95° C. for 10 min
25 cycles of: 95° C. for 15 sec; 51° C. for 15 sec (IA PCR primer Tm=56.4° C.);
70° C. for 60 sec
70° C. for 5 min
4° C. forever.
Two-Stage Emulsion PCR (Integrated Tagmentation with PCR):
37° C. for 15 min (USER, tagmentation)
55° C. for 10 min (tagmentation)
95° C. for 10 min (denature transposase)
8 cycles of: 95° C. for 15 sec; 40° C. for 15 sec; 70° C. for 30 sec (pre-amplification to generate F- and R-linked ends)
18 cycles of: 95° C. for 15 sec; 50° C. for 15 sec; 70° C. for 30 sec (amplification to generate products)
70° C. for 5 min
4° C. forever.
Final Library Amplification PCR:
Input 5 ng DNA
98° C. for 30 sec
7 or 8 cycles of: 98° C. for 10 sec; 65° C. for 75 sec;
65° C. for 5 min
4° C. forever Example 10—Protocol with emPCR 1. Make chain-oligos using click chemistry.
   a. AZ-F, AK-R->chain-oligo
   b. 4% E-Gel size-selection
2. Anneal Outside Adapter (OA) hairpin
   a. OA->OA hairpin
   b. no cleanup
3. Anneal Internal Adapter (IA)=double-stranded ME.
   a. ME-Chi, ME-Chic->IA
   b. no cleanup
4. Assemble transposome using Tn5 transposase and Internal Adapter (IA).
5. PreCR to repair template DNA (37° C. for 20 min), clean up.
   a. Nicks in template DNA
   b. Clean up using StrataClean and Nanosep 3K.
   c. PreCR reaction mixture cannot go to End Prep directly, because the $(NH_4)_2SO_4$ present in the ThermoPol buffer is known to inhibit T4 PNK.
6. Perform end repair and A-tailing on repaired template DNA (using NEBNext ultra II kit for Illumina).
7. Ligate OA to template DNA using 100× molarity of OA.
   a. OA, template DNA to form OA-template DNA
   b. Side-products: template DNA without OA ("non-OA DNA"), or template DNA with OA only on one end
8. Inactivate ligase by heating at 65° C. for 10 min.
9. Add Exo III and Exo VII to digest non-OA DNA at 37° C. for 2 hr (add fresh Exo at 1 hr).
   a. other nucleases may be used if desired, such as Lambda Exo or Exo I
10. Clean up using StrataClean (20 ul×4) and Nanosep 3K.
11. Integrated USER digestion and chain-PCR:
    a. longer time periods may be used if necessary (e.g., denaturing) to ensure migration/diffusion of ends and amplified ends in the droplets and to enable two ends to be linked by chain-oligos.
    b. PCR components:
       i. PCR mastermix
       ii. transposome inserted template DNA
       iii. IA-oligo=ME
       iv. chain-oligo (F and R chain-oligos may be used that do not carry the 12-bp seqcommon)
       v. USER (to cut at the dU in OA)
       vi. pre-assembled transposome
    c. Limited amount of chain-oligo maximizes the yield of two-arm PCR products and minimizes one-arm PCR products and free chain-oligo
    d. Break emulsion and purify chain-products.
    e. EURx emulsion PCR kit can effectively remove contaminants such as: ethidium bromide, primers (shorter than 40 nt), short, double-stranded DNA (shorter than 20 bp), RNA, Taq DNA Polymerase, Pfu DNA Polymerase, endo- and exonucleases, DNA binding and modifying proteins, BSA, and other enzymes/proteins, lipids, endotoxins, dyes, detergents, nucleotides, radio- and chemical labels, EDTA, problematic restriction and ligation inhibitors, buffers and salts.
    f. Zymo CC5 column can replace EURx column. But in some cases the precipitated salt (or emulsion formed from pipetting aqueous phase with the remaining trace of organic phase) blocks the flow of liquid.
    g. Biotin purification
    h. Desthiobiotin binding
    i. Elute with biotin
    j. Circularization ligation using blunt end ligation O/N.
    k. Insufficient circularization can bias to short products circularization
    l. Intermolecular ligation can result in randomly linked ends.
    m. To favor circularization, there is a balance between increasing temperature to facilitate molecule movement and decreasing temperature to favor blunt ends stabilization. Thus, using T4 DNA ligase, 16C is normally been used.
12. Use Lambda Exo and Exo I to digest uncircularized DNA and oligos, cleanup using zymo CC5.
    a. Use PS bonds to protect the 3' strand of dsDNA ends
    b. Lambda Exo: Lambda Exonuclease is a highly processive exodeoxyribonuclease that selectively digests the phosphorylated strand of double-stranded DNA. The preferred substrate is blunt-ended, 5'-phosphorylated double-stranded-DNA. The enzyme has reduced activity against nicked DNA and against single-stranded DNA and gapped DNA.
    c. Exo I: Exonuclease I specifically digests single stranded DNA, containing a 3'-OH in a 3'-OH, in a 3'→5' direction. Although the enzyme requires $Mg^{+2}$ for activity, it is active in a wide variety of buffers and can be added directly into most reaction mixes. Exonuclease I can be heat inactivated by incubation at 80° C. for 15 minutes.
13. PCR to amplify circularized OA'ed ends using F and R seq primers, and indexed seq adapter primers, like those from NEBNext kit
    a. low annealing temperature can cause unspecific amplification between F and R and result in F—F and R—R molecules
    b. NEB indexed primers contains the common seq part of seq F and R. Use indexprimers without this common part will be more specific to amplify F-Rmolecules.
14. Size-selection using 2% E-gel for 280-730 bp (150-600 bp inserts)
15. PE Seq of 150+150 bp Outside Adapter (OA)

(SEQ. ID. No: 3)
5'/5Phos/GATCGGAAGAGC
GC*T*G*T*G*GTAUCGC*C*A*C*C*A*GCGCTCTTCCGATC*T Annealed OA:

EndAmp Primers:

XX039:
(SEQ. ID. No: 4)
5'ACACTCTTTCCCTACACGACGCTCTTCCGATCT

XX038:
(SEQ. ID. No: 5)
5'GTGACTGGAGTTCAGACGTGTGCTCTTCCGATCT

Crab-Oligo:

```
XX109_crab_5AZ:
                                    (SEQ. ID. No: 6)
5'/5AzideN//iSp18/A*C*A*C*T*C*TTTCCCTACACGAC XX117_crab_5AK:
                                    (SEQ. ID. No: 7)
5'/5Hexynyl//iSp18//ideSBioTEG/G*T*G*A*C*T*G
GAGTTCAGACGTGT
```

Internal Adapter (IA), Blunt End Ligation

```
XX118_MEout_TOP:
                                    (SEQ. ID. No: 8)
5'CCACCAGCCTGTCTCTTATACACATCT XX119_MEout_BOT:
                                    (SEQ. ID. No: 9)
5'/5Phos/AGATGTGTATAAGAGACAGGCTGGTGG
```

Internal Adapter (IA), BseRI Sticky End Version

```
XX121-ME-BseRI-TOP:
                                   (SEQ. ID. No: 10)
5'GAGGAGAGATGTGTATAAGAGACAG

XX122-ME-BseR1-BOT:
                                   (SEQ. ID. No: 11)
5'CTGTCTCTTATACACATCTCTCCTC
```

Internal Adapter (IA), EciI Sticky End Version

```
XX123-ME-EciI-TOP:
                                   (SEQ. ID. No: 12)
5'GGCGGAAGATGTGTATAAGAGACAG

XX124-ME-EciI-BOT:
                                   (SEQ. ID. No: 13)
5'CTGTCTCTTATACACATCTTCCGCC
```

Custom Sequencing Primers
Sequencing read1 primer=XX039
Sequencing read2 primer=XX038

Example 11—One-Pot Setup Provides More Flexibility for Optimization

Transposome assembly and tagmentation reactions can be set up on a "one-pot" reaction, which can enable optimization of appropriate reaction conditions (FIGS. 10-14).

Example 12—Crab-Seq (Same Outside Adapters)

Figure 15:
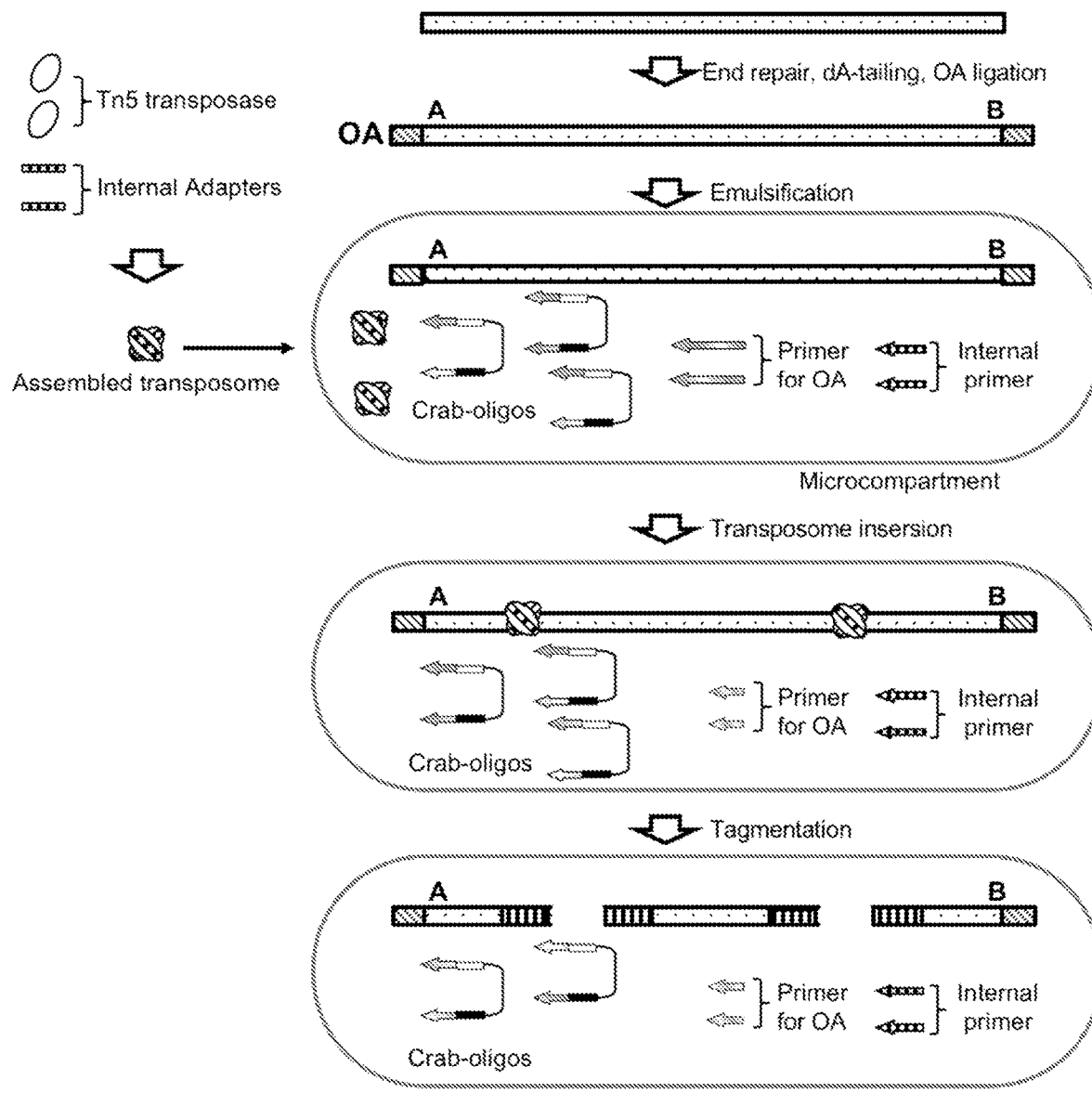
FIG. 15 shows a representation of the crab-seq technique as described herein with the following steps: Step 1 shows a DNA template with two ends labeled A and B. Step 2 shows end repair, dA-tailing and TA ligation of Outside Adapters (OA). Step 3 shows emulsification, droplet containing OA-ligated DNA template, Crab-oligos, free end oligos, internal oligos, and pre-assembled Tn5 transposome carrying Internal Adapter (IA). Step 4 shows transposition to insert IA. Step 5 shows PCR using heat to denature transposome and fragment DNA, DNA ends amplified by free end oligos, and amplification with Crab-oligos. Step 6 shows breakage of emulsion. Step 7 shows biotin pulldown to enrich Crab-products using built-in biotin in Crab-oligos. Step 8 shows circularization. Step 9 shows exonuclease digestions to remove linear DNA. Step 10 shows PCR to amplify circularized Crab-products and addition of indexed sequencing adapters.
Figure 15:
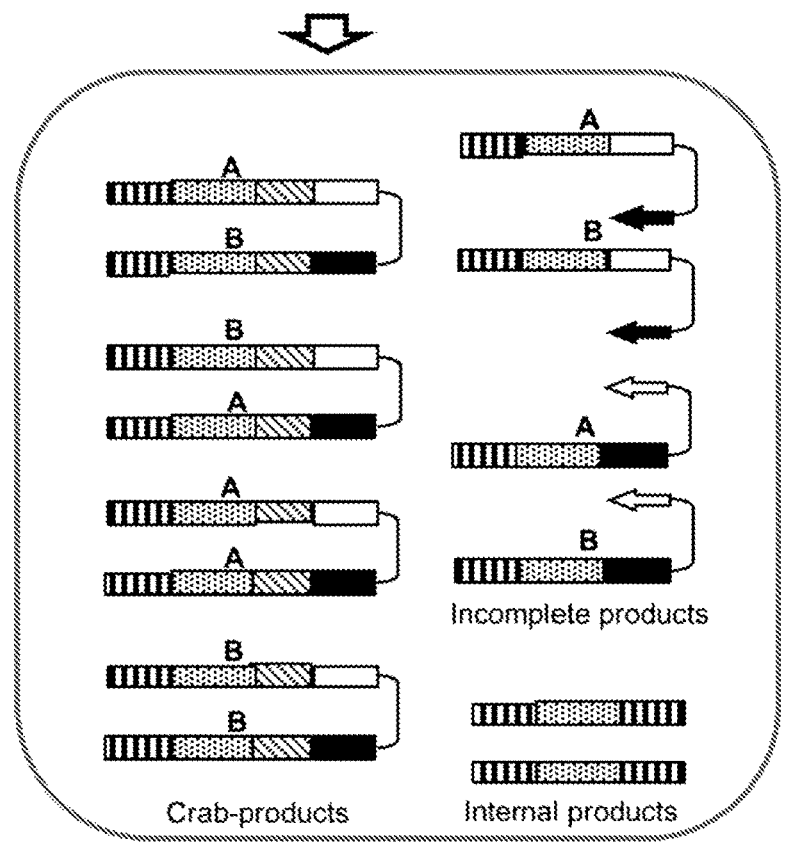
Figure 15:
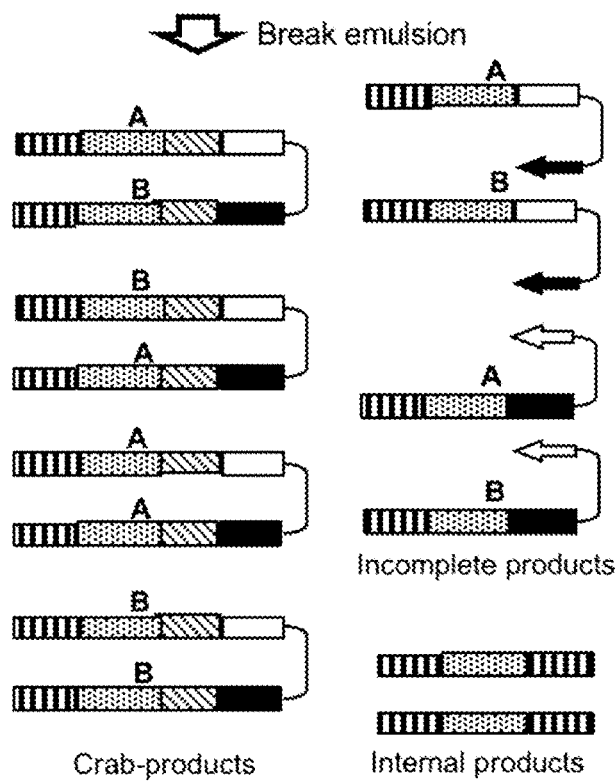
Figure 15:
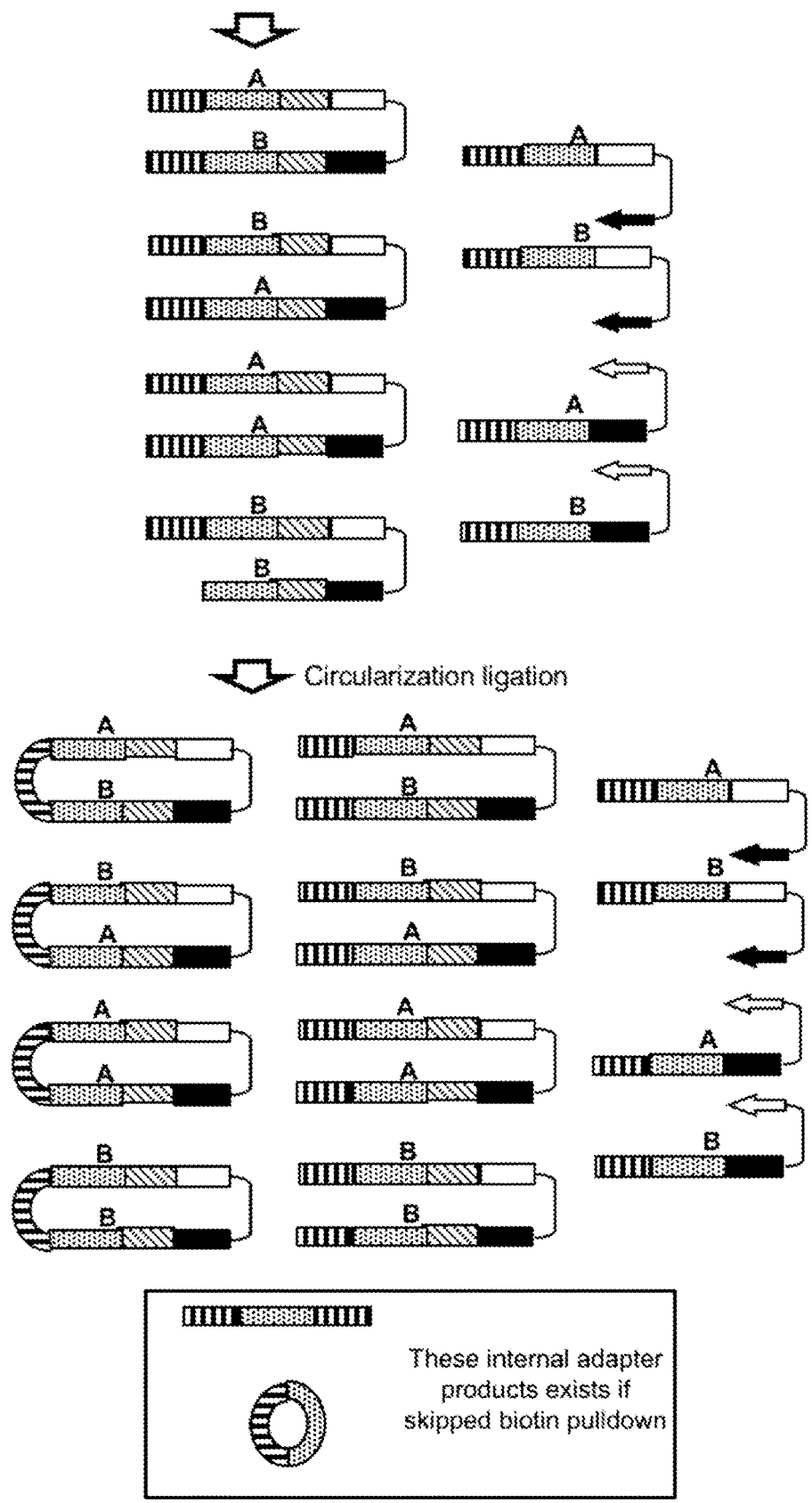
Figure 15:
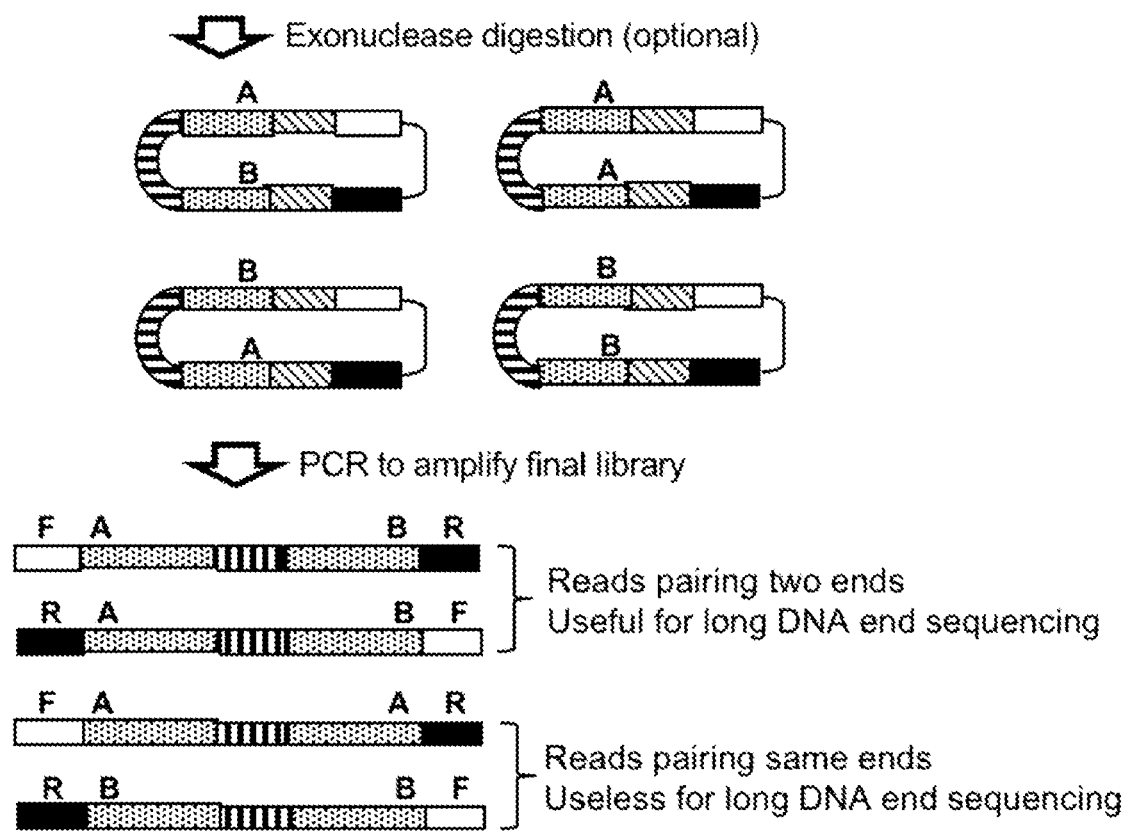
Figure 16A:
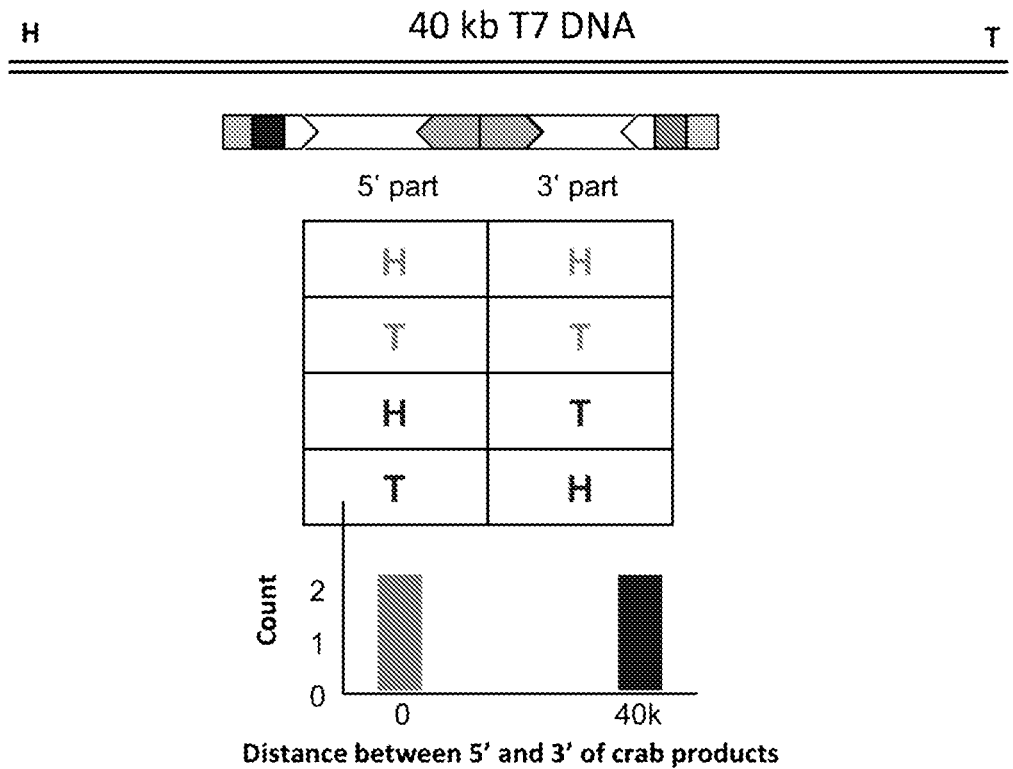
FIG. 16A shows distance between 5' and 3' of crab products with Crab-seq on 40 kb T7 DNA.
Figure 16B:
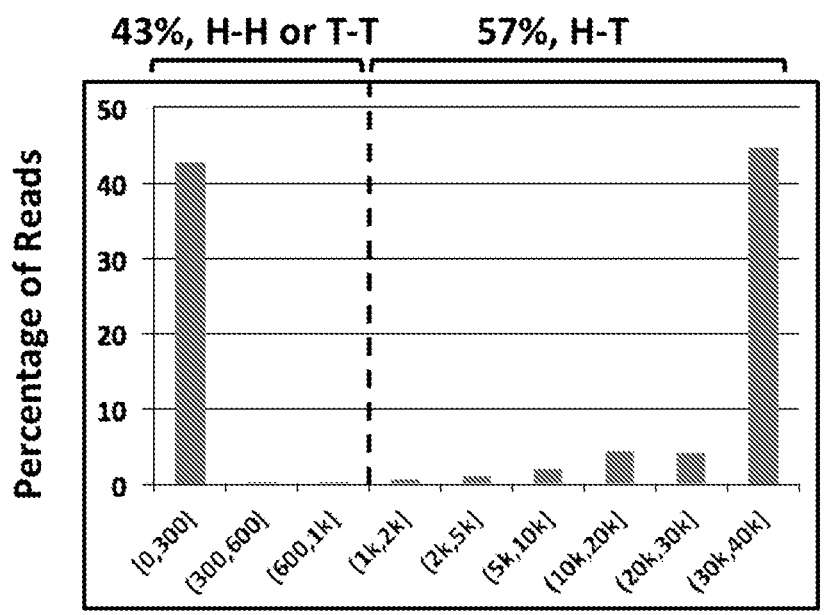
FIG. 16B shows percentage of reads, with 43% of the reads being head-head or tail-tail configuration, and 57% being head-tail configuration.

A schematic overview of Crab-Seq procedure is shown in FIG. 15.
A. Adapters and Oligos
a. Outside Adapter:
Outside Adapter is a hairpin formed from oligo OA.
OA (*=phosphothiate bond, /5Phos/=5' Phosphorylation):

```
                                   (SEQ. ID. No: 14)
5' /5'Pho/GATCGGAAGAGCGC*T*G*G*T*G*GTAUCGC*C*A*C*
C*A*GCGCTCTTCCGATC*T
```

OA Hairpin:

```
                                                 /T\
5'/5Phos/ GATCGGAAGAGCGC*T*G*G*T*G*G    A
         ||||||||||||||  | | | | |      U
3' T*CTAGCCTTCTCGCG*A*C*C*A*C*C    C
                                                 \G/
``` b. Outside Adapters Amplification Primers:

```
OA1-F-per:
                                   (SEQ. ID. No: 15)
5' ACACTCTTTCCCTACACGACGCTCTTCCGATCT OA2-R-per:
                                   (SEQ. ID. No: 16)
5' GTGACTGGAGTTCAGACGTGTGCTCTTCCGATCT
``` c. Covalently Linking Oligos:
Covalently linking oligos (Crab oligos) are covalently linked from these two oligos by their 5' and 5', using Azide-Alkyne Huisgen Cycloaddition.
Azide oligo (*=phosphothiate bond, /5AzideN/=5' Azide (NHS Ester), /iSp18/=Internal Spacer 18):

```
                                   (SEQ. ID. No: 17)
5' /5AzideN//iSp18/A*C*A*C*T*C*TTTCCCTACACGAC
```

Alkyne oligo (*=phosphothiate bond, /5Hexynyl/=5' Hexynyl, /iSp18/=Internal Spacer 18):

```
                                   (SEQ. ID. No: 18)
5' /5Hexynyl//iSp18//ideSBioTEG/G*T*G*A*C*T*GGAGTT
CAGACGTGT
``` d. Internal Adapter:
Internal Adapter was Annealed from Two Oligos:

```
IA_top:
                                   (SEQ. ID. No: 19)
5' GAGGAGAGATGTGTATAAGAGACAG IA_btm:
                                   (SEQ. ID. No: 20)
5' CTGTCTCTTATACACATCTCTCCTC
```

Anneal IA_Top and IA_btm to Form Internal Adapter:

```
5' GAGGAGAGATGTGTATAAGAGACAG
   |||||||||||||||||||||||||
3' CTCCTCTCTACACATATTCTCTGTC
``` e. Internal Adapter Amplification Primer:

```
IA_pcr:
                                   (SEQ. ID. No: 21)
5' GAGGAGAGATGTGTATAAGAGACAG
```

B. Steps:
1. Click chemistry to covalently link Azide oligo and Alkyne oligo
   To make 10 mM Copper (II)-TBTA Stock in 55% DMSO:
   Dissolve 50 mg of copper (II) sulfate pentahydrate in 10 ml of distilled water.
   Dissolve 116 mg of TBTA ligand in 11 mL of DMSO.
   Mix two solutions.

To make 2 M Triethylammonium Acetate Buffer, pH 7.0:

Mix 2.78 mL of triethylamine with 1.14 mL of acetic acid.
Add water to 10 mL volume, and adjust pH to 7.0.

Click chemistry reaction setup:

| | |
|---|---|
| 30 µl | Azide oligo, 10 µM |
| 30 µl | Alkyne oligo, 10 µM |
| 7.5 µl | Triethylammonium Acetate Buffer, pH 7.0, 2M |
| 67.5 µl | DMSO |
| 15 µl | Ascorbic Acid, 5 mM, freshly made |
| 8 µl | Copper (II)-TBTA Stock, 10 mM |
| Total 158 µl | |

Incubate at room temperature for 1-24 hours.
Purify DNA using Oligo Clean & Concentrator (Zymo Research).
Size-selected clicked oligos using 4% E-Gel (Thermo Fisher Scientific) and clean up using using Oligo Clean & Concentrator (Zymo Research).

2. *E. coli* DH5α genomic DNA was prepared using Gentra® Puregene® kit (Qiagen) following vender's protocol. DNA was stored at 4 until use.
3. To generate 5-10 kb templates DNA, genomic DNA was sheared using g-TUBE (Covaris) with a benchtop centrifuge according to vendor's protocol and then size-selected with BluePippin (Sage Science). The size ranges of size-selected genomic DNA was confirmed using Fragment Analyzer (Advanced Analytical Technologies).
4. End Repair, dA-tailing and Adapter ligation steps are performed on the size-selected templates DNA using KAPA Hyper Prep Kit (Kapa Biosystems), KAPA HyperPlus Kit (Kapa Biosystems) or NEBNext Ultra II kit (New England Biolabs) following vendors's protocols. An example of using Kapa HyperPlus Kit is listed below.

End Repair and dA-Tailing

| | |
|---|---|
| x µl | DNA (up to 1 µg) |
| 50-x µl | H2O |
| 7 µl | End Prep Buffer |
| 3 µl | End Prep Enzyme |
| Total 60 µl | |

Put PCR tube in a thermocycler and perform the following steps:
Incubate at 20 for 30 minutes with lid off.
Incubate at 65 for 30 minutes.
Take out reaction and perform the next step immediately.

Outside Adapters ligation

| | |
|---|---|
| 60 µl | DNA from above |
| 5 µl | Annealed OA1-F, 5 µM |
| 5 µl | Annealed OA2-R, 5 µM |
| 30 µl | Ligation Buffer |
| 10 µl | DNA Ligase |
| Total 110 µl | |

Incubate at 16 for 18 hours.

5. To minimize DNA damage we used a mild DNA clean up protocol. First, Proteinase K was added to the adapter ligation reaction to digest enzymes. Second, Proteinase K was extracted using StrataClean Resin (Agilent Genomics) twice. Last, reaction mixture was dialysed in Tris-EDTA pH 8.0 buffer (5 mM Tris base, 0.05 mM EDTA).
6. DNA that was not ligated Outside Adapters at both ends was digest with Exonucleases.

An example is showing below.

| | |
|---|---|
| 25 µl | DNA |
| 18 µl | H2O |
| 5 µl | CutSmart buffer (New England Biolabs) |
| 1 µl | Exonuclease III (New England Biolabs) |
| 1 µl | Exonuclease VII (New England Biolabs) |
| Total 50 µl | |

Incubate at 37 for 1 hour.

7. DNA was then size-selected using BluePippin (Sage Science).
8. Size-selected DNA was repaired using DNA damage repair enzymes, such as those included in the PreCR® Repair Mix (New England Biolabs). An example of using PreCR® Repair Mix (New England Biolabs) to repair DNA is showing below.

| | |
|---|---|
| x µl | DNA (up to 500 ng) |
| 43-x µl | H2O |
| 5 | 10x ThermoPol Buffer |
| 0.5 µl | dNTPs, 10 mM |
| 0.5 µl | 100x NAD+ |
| 1 µl | PreCR ® Repair Enzyme Mix |
| Total 50 µl | |

Incubate at 37 for 1 hour, then immediately perform the emulsion PCR step.

9. Tn5 transposome was assembled using EZ-Tn5 Transposase (Epicentre) or Robust Tn5 Transposase (Creative Biogene) and Internal Adapter following vendors's protocols. An example setup is showing below.

| | |
|---|---|
| 13 µl | H2O |
| 2 µl | 10x TPS buffer |
| 1 µl | Annealed Internal Adapter, 40 µM |
| 4 µl | Robust Tn5 transposase |
| Total 20 µl | |

Incubate at 25 for 30-60 minutes.

10. The integrated tagmentation and emulsion PCR was set up using Micellula DNA Emulsion & Purification Kit (EURx) or in-house microfluidics devices. Average number of template copies per droplet was kept below 0.1, to minimize multiple copies of templates presenting in droplets. An example of emulsion PCR setup using Micellula DNA Emulsion & Purification Kit (EURx) is listed below.

Set up the following 50 ul reaction in 200 ul PCR tube on ice.

| | |
|---|---|
| x μl | Outside Adapter ligated DNA (1x1^9 molecules) |
| 21.7-x μl | H2O |
| 10 μl | 5x TD (Creative Biogene) |
| 2.5 μl | dNTP, 10 mM |
| 2.5 μl | KCl, 2M |
| 0.5 μl | OA1-F-pcr, 2 μM |
| 0.5 μl | OA2-R-pcr, 2 μM |
| 1 μl | Crab_oligos, 10 μM |
| 0.4 μl | IA_pcr, 100 μM |
| 7.5 μl | Acetylated BSA, 10 mg/ml |
| 1 μl | USER (New England Biolabs) |
| 2 μl | SuperFi Polymerase (Thermo Fisher Scientific) |

Add pre-assembled Tn5 transposome right before adding oil and vortex.

| | |
|---|---|
| 0.4 μl | Pre-assembled Tn5 Transposome |

Add 300 ul ice cold emulsion PCR oil (220 μl of Emulsion Component 1, 20 μl of Emulsion Component 2, 60 μl of Emulsion Component 3, mix well).
Vortex at high speed at 4 for 3 minutes.
Put in thermocycler and run the following program:

| | |
|---|---|
| 37 , 30 min | (USER digestion, tagmentation) |
| 55 , 12 min | (tagmentation) |
| 94 , 10 min | (inactivate transposase) |
| 50 cycles | (amplification) |
| { | |
| 94 , 10 sec | |
| 60 , 45 sec | |
| 70 , 60 sec | |
| } | |
| 70 , 3 min | |
| 4 , hold | |

Breaking emulsion using Micellula DNA Emulsion & Purification Kit (EURx) following vendor's protocol.

11. Success PCR products, i.e., PCR products covalently linked by the Covalently linking oligos were enriched by biotin pulldown using the built-in DesthioBiotin in the Alkyne oligo and Dynabeads MyOne Streptavidin C1 (Thermo Fisher Scientific), following vendor's protocol. An example protocol is listed below.
Pulldown using MyOne C1 with Desthiobiotin-TEG
Wash 20 ul beads with 1000 ul 1× Binding and Washing Buffer (5 mM Tris-HCl (pH 7.5), 0.5 mM EDTA, 1 M NaCl) for 3 times.
Resuspend beads in 20 ul of 2× Binding and Washing Buffer (10 mM Tris-HCl (pH 7.5) 1 mM EDTA 2 M NaCl buffer.
Add beads to 20 ul eluted DNA from above breaking emulsion step.
Incubate at room temperature for 1 hour.
Wash twice with 200 ul of 1× Binding and Washing Buffer.
Remove washing buffer.
Add 50 ul of biotin elution buffer (100 mM Tris-HCl (pH 8.0), 250 mM NaCl, 1 mM EDTA, 10 mM D-biotin).
Incubate at room temperature for 1 hour.
Clean up DNA using DNA Clean & Concentrator Kit (Zymo Research).

12. PCR products were size-selected on 2% E-Gel (Thermo Fisher Scientific) for 500-1,000 bp range, and extracted using QIAquick Gel Extraction Kit (Qiagen).
13. Size-selected PCR products were digested using BseRI (New England Biolabs) at for 30 min following vendor's protocol and cleaned up using DNA Clean & Concentrator Kit (Zymo Research).
14. Circularization ligation was performed using T4 DNA ligase (New England Biolabs) at 16 for 1-16 hours and T4 DNA ligase was inactivated at 65 for 10 minutes.
15. Linear DNA was digested using Lambda Exonuclease (New England Biolabs) and Exonuclease I (New England Biolabs) at 37 for 30 min following vendor's protocol and cleaned up using DNA Clean & Concentrator Kit (Zymo Research).
16. Illumina sequencing adapters were added using PCR with indexed oligos (New England Biolabs) and NEBNext Ultra II Kit (New England Biolabs). Products were cleaned up using 0.9× Agencourt AMPure XP (Beckman Coulter) following NEBNext Ultra II Kit protocol.
17. Final library was sequenced on MiSeq System (Illumina) using MiSeq Reagent Kit v3 (600-cycle).
18. Illumina sequencing results was split at the internal adapter junction, then 5' part and 3' part of each read were mapped to *E. coli* DH5α reference genome using Burrows-Wheeler Aligner (BWA) (Li H. and Durbin R. (2009) Bioinformatics, 25:1754.). The distance between the locations of 5' and 3' parts mapped to the reference genome was calculated for all reads. For the reads that have distance in the range of the length of the templates DNA, they were generated from the two ends of the template DNAs and provide long distance sequencing information. The results of Crab-Seq on 5-10 kb *E. coli* gDNA are shown in FIG. 17A-17B.

Example 13—Fiddler-Crab-Seq (Two Types of Outside Adapters)

The major difference between Crab-Seq and Fiddler-Crab-Seq is that Fiddler-Crab-Seq uses two different outside adapters to ligate to the ends of template DNA. Though the protocols of these two versions of Crab-Seq look similar, they are significantly different.

In Crab-Seq, there is only one type of outside adapter. After outside adapter ligation, there are mixture of various products, including two-end ligated templates, one-end ligated templates, and non-ligated templates. In the following emulsion PCR step, one-end ligated templates will produce covalently linked PCR products that are generated from the same template ends, i.e., Crab linked the copies of the same template ends in emulsion PCR. These "same end" products are not useful for long distance DNA sequencing and will waste sequencing reads.

To remove one-end ligated templates before emulsion PCR, one can use exonuclease digestion. However, due to the long length of DNA templates (up to 30 kb) and the ligation mixture is not optimal for typical exonucleases (such as Exonuclease V, or Exonuclease III plus Exonuclease VII) activities, the exonuclease digestion is not complete and thus does not remove all of (if any) one-end ligated templates. If one chooses to clean up outside adapter ligated DNA before exonuclease digestion, long DNA are very easily broken or tangled together during the cleaning up step. This will result in many newly one-end ligated templates and will lead to the same problem described above.

Figure 18:
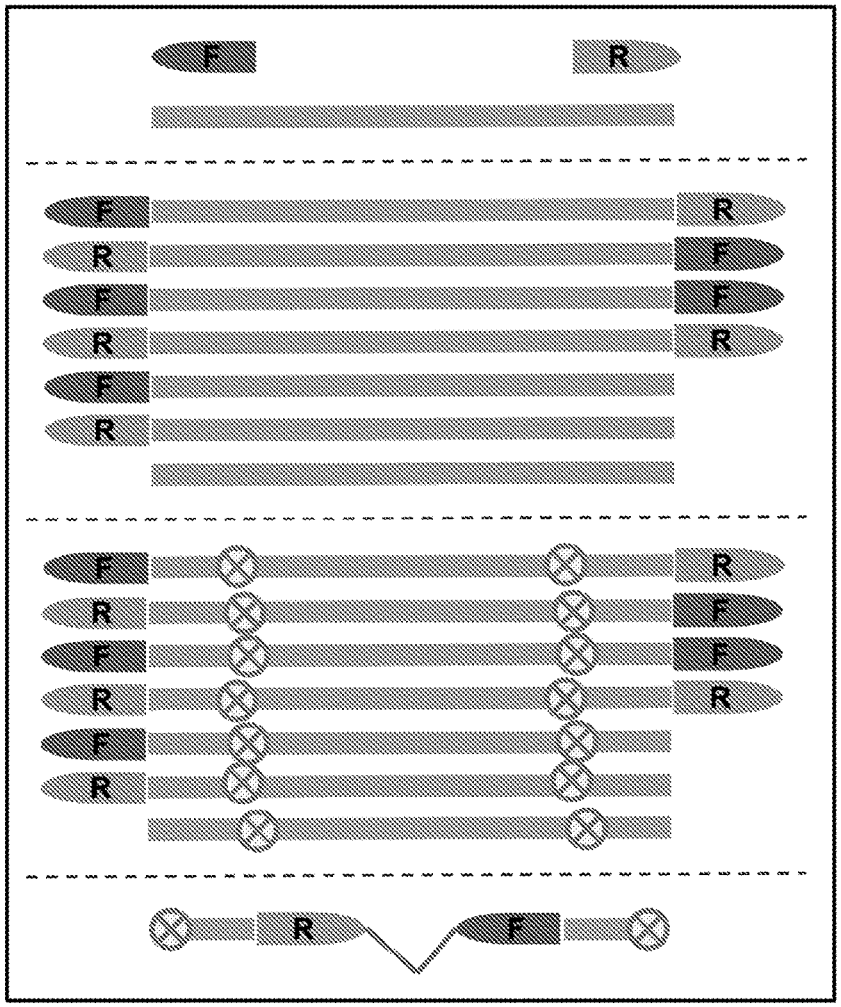
FIG. 18 shows Fiddler-Crab-Seq strategy for suppression PCR to eliminate damaged or partially end-labeled molecules and keep only proper "Forward and Reverse".
Figure 19:
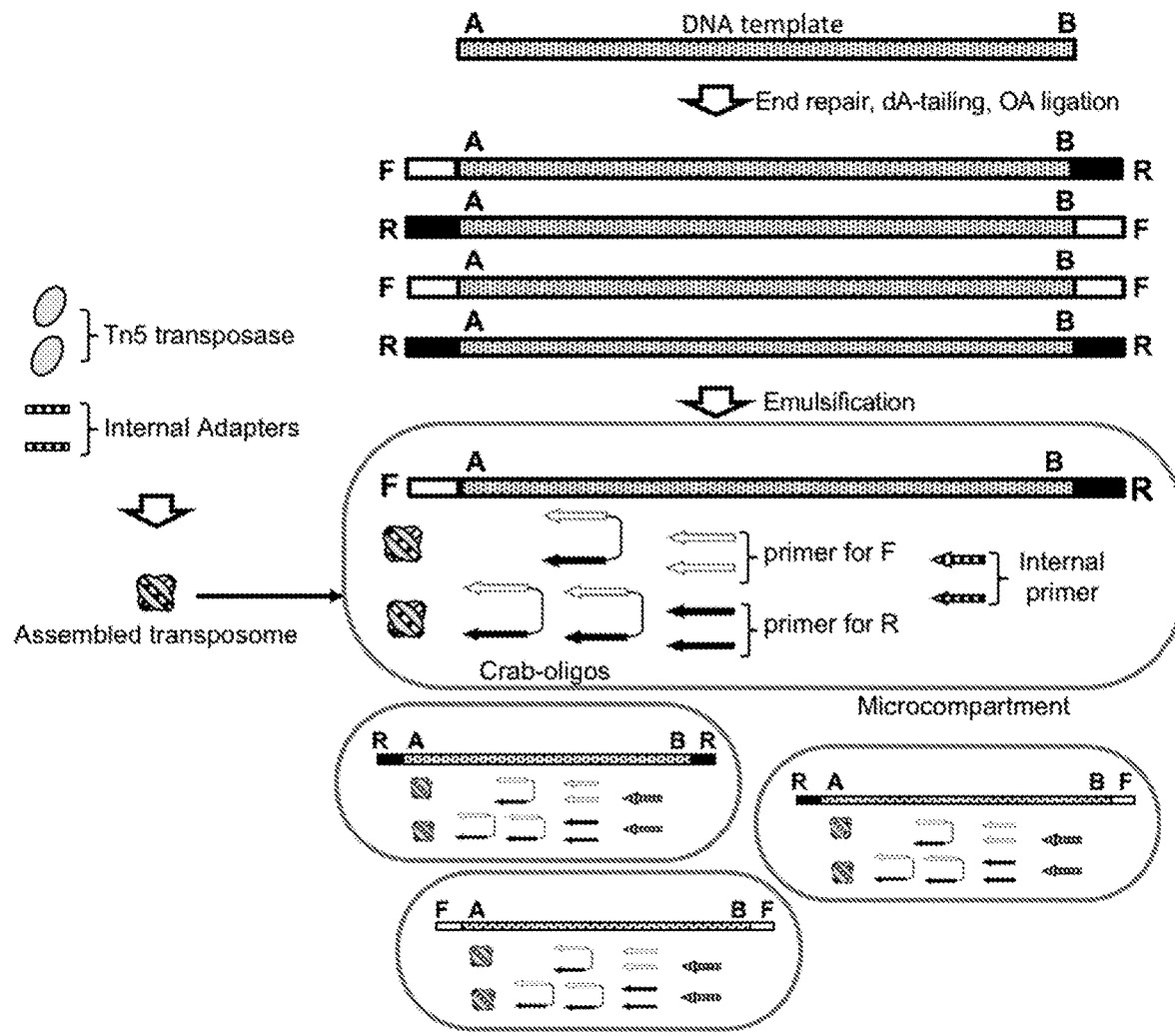
FIG. 19 shows a representation of the Fiddler-Crab-Seq technique as described herein with the following steps: Step 1 shows a DNA template with two ends labeled A and B. Step 2 shows end repair, dA-tailing and TA ligation of Outside Adapters (OA) F and R. Step 3 shows emulsification, droplet containing OA-ligated DNA template, Crab-oligos, free end oligos, internal oligos, and pre-assembled Tn5 transposome carrying Internal Adapter (IA). Step 4 shows transposition to insert IA. Step 5 shows PCR using heat to denature transposome and fragment DNA, DNA ends amplified by free end oligos, and amplification with Crab-oligos. Step 6 shows breakage of emulsion. Step 7 shows biotin pulldown to enrich Crab-products using built-in biotin in Crab-oligos. Step 8 shows circularization. Step 9 shows exonuclease digestions to remove linear DNA. Step 10 shows PCR to amplify circularized Crab-products and addition of indexed sequencing adapters.
Figure 19:
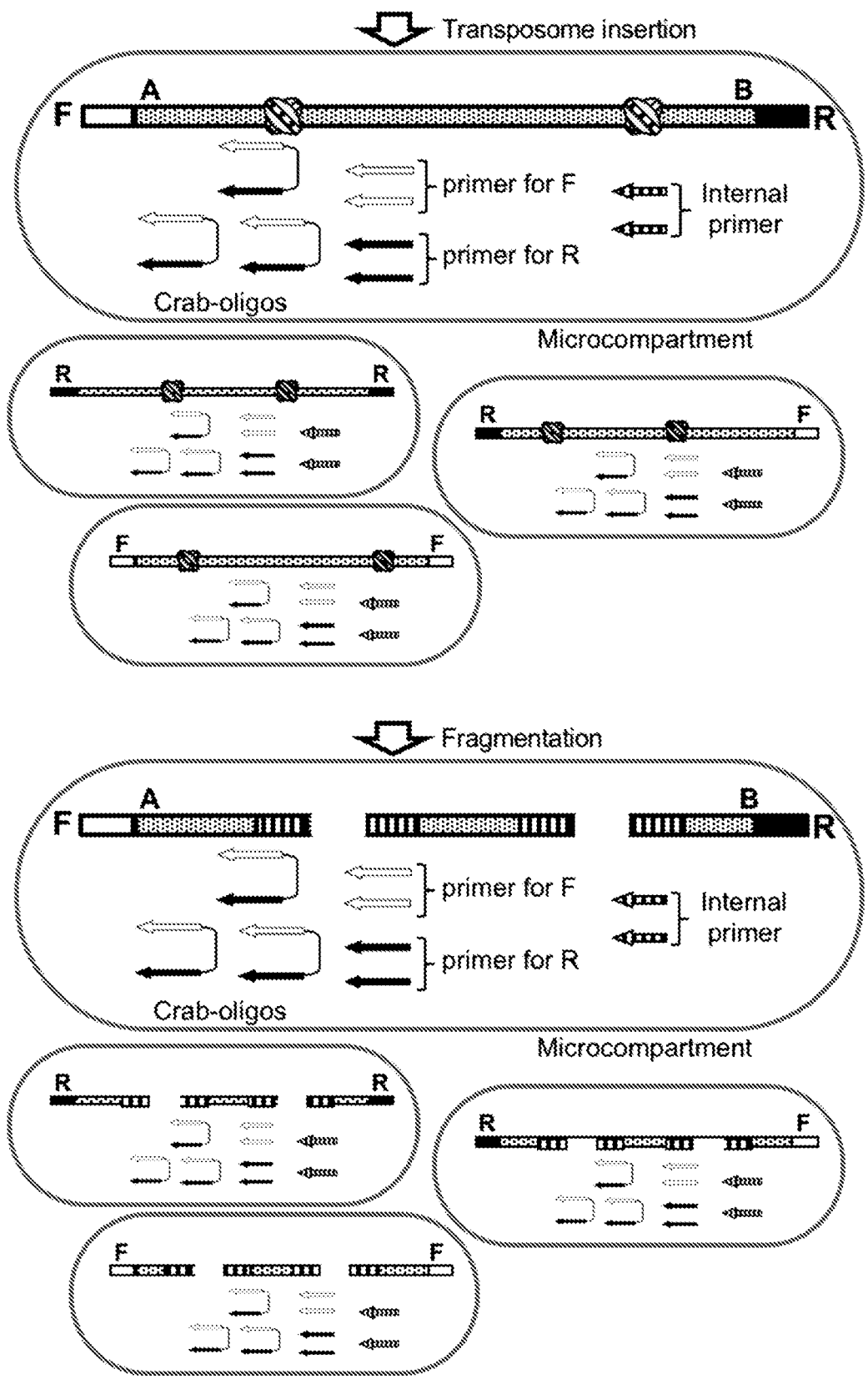
Figure 19:
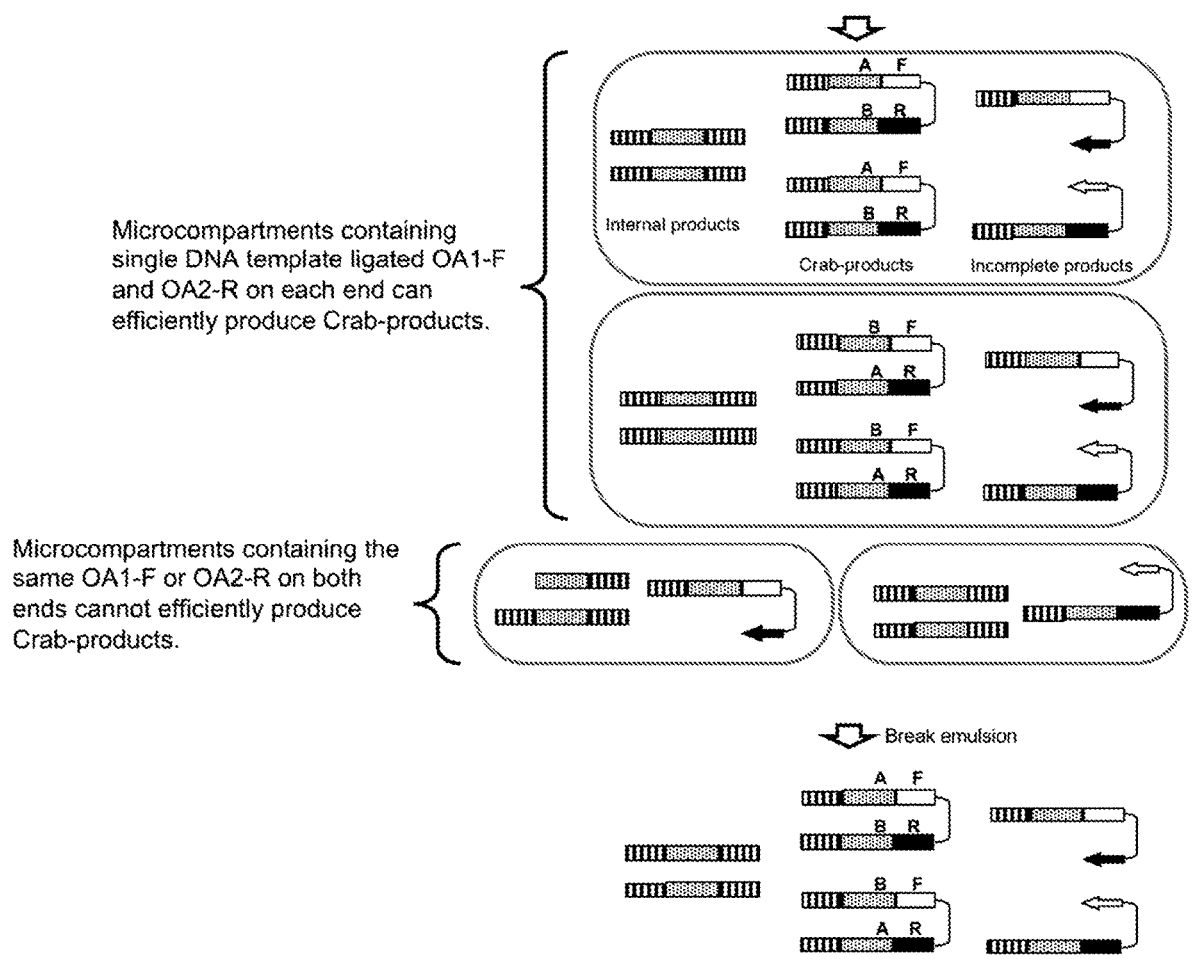
Figure 19:
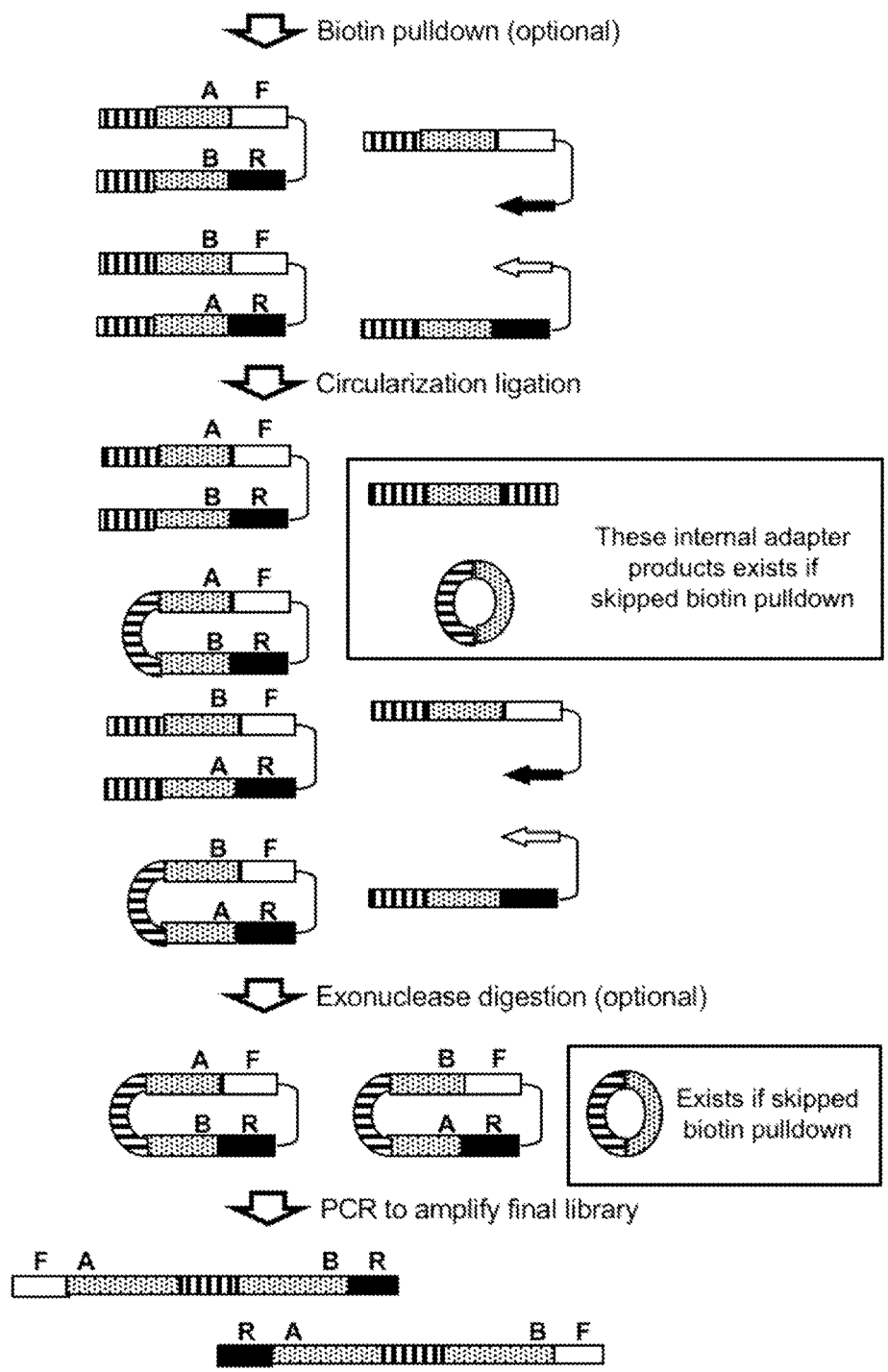

In Fiddler-Crab-Seq, two different outside adapters were used and each compatible with one arm of the covalently linked oligos (crab). Theoretically, if 100% ligation efficiency can be achieved, only as much as 50% DNA templates will be ligated two types of outside adapters at each ends, with the other 50% been ligated the same adapter at both ends. This sounds like a drawback to the efficiency. But the significant advantage of this strategy is that only two-end ligated templates can produce covalently linked PCR products in emulsion PCR. And all of the other templates, including one-end ligated, non-ligated, and even broken templates, cannot produce covalently linked PCR products. This significantly reduced the background noise in the sequencing results that were produced from two randomly paired DNA template ends which most likely resulted from random pairing of one-end ligated or broken templates ends in the same emulsion droplets. FIG. 18 shows Fiddler-Crab-Seq strategy for suppression PCR to eliminate damaged or partially end-labeled molecules and keep only proper "Forward and Reverse". A schematic overview of the Fiddler-Crab-Seq procedure is shown in FIG. 19.

A. Adapters and Oligos a. Outside Adapters:

1. Outside Adapter 1 is a hairpin formed from oligo OA1-F.

OA1-F (*=Phosphothiate Bond, /5Phos/=5' Phosphorylation):

(SEQ. ID. No: 22)
5' /5Phos/GATCGGAAGAGCGTCGTGTAGGGAAAGAGTGTTUTCCTTC

CCTTCCCTTCCCTTCCTUTACACTCTTTCCCTACACGACGCTCTTCCGAT

C*T

OA1-F Hairpin:

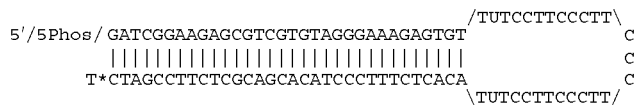

OA1-F carrying other type of loop containing dU also work, such as TAUCG.

(SEQ. ID. No: 23)

2. Outside Adapter 2 is a hairpin formed from oligo OA2-R.

OA2-R (*=phosphothiate bond, /5Phos/=5' Phosphorylation):

(SEQ. ID. No: 24)
5' /5Phos/GATCGGAAGAGCACACGTCTGAACTCCAGTCACTUTGGTG

GTGGTGGGTTGTTGTTGTUTGTGACTGGAGTTCAGACGTGTGCTCTTCCG

ATC*T

OA2-R Hairpin:

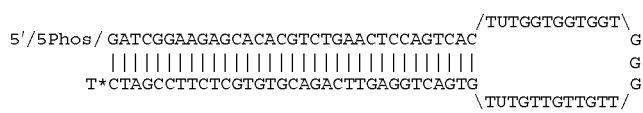

OA2-R carrying other type of loop containing dU also work, such as TAUCG.

(SEQ. ID. No: 29)

b. Outside Adapters Amplification Primers:

```
OA1-F-pcr:
                                   (SEQ. ID. No: 26)
5' ACACTCTTTCCCTACACGAC OA2-R-pcr:
                                   (SEQ. ID. No: 27)
5' GTGACTGGAGTTCAGACGTGT
``` c. Covalently Linking Oligos:

Covalently linking oligos (Crab_oligos) are covalently linked from these two oligos by their 5' and 5', using Azide-Alkyne Huisgen Cycloaddition.

Azide oligo (*=phosphothiate bond, /5AzideN/=5' Azide (NHS Ester), /iSp18/=Internal Spacer 18):

```
                                   (SEQ. ID. No: 28)
5' /5AzideN//iSp18/A*C*A*C*T*C*TTTCCCTACACGAC
```

Alkyne oligo (*=phosphothiate bond, /5Hexynyl/=5' Hexynyl, /iSp18/=Internal Spacer 18):

```
                                   (SEQ. ID. No: 29)
5' /5Hexynyl//iSp18//ideSBioTEG/G*T*G*A*C*T*GGAGT
TCAGACGTGT
``` d. Internal Adapter:

Internal Adapter was Annealed from Two Oligos:

```
IA_top:
                                   (SEQ. ID. No: 30)
5' GAGGAGAGATGTGTATAAGAGACAG IA_btm:
                                   (SEQ. ID. No: 31)
5' CTGTCTCTTATACACATCTCTCCTC
```

Anneal IA_Top and IA_btm to Form Internal Adapter:

```
5' GAGGAGAGATGTGTATAAGAGACAG
   |||||||||||||||||||||||||
3' CTCCTCTCTACACATATTCTCTGTC
``` e. Internal Adapter Amplification Primer:

```
IA_pcr:
                                   (SEQ. ID. No: 32)
5' GAGGAGAGATGTGTATAAGAGACAG
```

B. Steps:

1. Click chemistry to covalently link Azide oligo and Alkyne oligo

To make 10 mM Copper (II)-TBTA Stock in 55% DMSO:

Dissolve 50 mg of copper (II) sulfate pentahydrate in 10 ml of distilled water.

Dissolve 116 mg of TBTA ligand in 11 mL of DMSO.

Mix two solutions.

To make 2 M Triethylammonium Acetate Buffer, pH 7.0:

Mix 2.78 mL of triethylamine with 1.14 mL of acetic acid.

Add water to 10 mL volume, and adjust pH to 7.0.

Click chemistry reaction setup:

| | |
|---|---|
| 30 µl | Azide oligo, 10 µM |
| 30 µl | Alkyne oligo, 10 µM |
| 7.5 µl | Triethylammonium Acetate Buffer, pH 7.0, 2M |
| 67.5 µl | DMSO |
| 15 µl | Ascorbic Acid, 5 mM, freshly made |
| 8 µl | Copper (II)-TBTA Stock, 10 mM |

Total 158 µl

Incubate at room temperature for 1-24 hours.

Purify DNA using Oligo Clean & Concentrator (Zymo Research).

Size-selected clicked oligos using 4% E-Gel (Thermo Fisher Scientific) and clean up using using Oligo Clean & Concentrator (Zymo Research).

2. *E. coli* DH5α genomic DNA was prepared using Gentra® Puregene® kit (Qiagen) following vender's protocol. DNA was stored at 4 until use.

3. To generate templates DNA of 1-2 kb, genomic DNA was treated with NEBNext® dsDNA Fragmentase® (New England Biolabs), size-selected on 1% E-Gel (Thermo Fisher Scientific), and purified using QIAquick Gel Extraction Kit (Qiagen). To generate 5-10 kb and 10-30 kb templates DNA, based on the size range of the purified genomic DNA, genomic DNA was either used directly for size-selection with BluePippin (Sage Science), or was sheared using g-TUBE (Covaris) with a benchtop centrifuge according to vendor's protocol and then size-selected with BluePippin (Sage Science). The size ranges of size-selected genomic DNA was confirmed using Fragment Analyzer (Advanced Analytical Technologies).

4. End Repair, dA-tailing and Outside Adapter ligation steps are performed on the size-selected templates DNA using KAPA Hyper Prep Kit (Kapa Biosystems), KAPA HyperPlus Kit (Kapa Biosystems) or NEBNext Ultra II kit (New England Biolabs) following vendors's protocols. An example of using Kapa HyperPlus Kit is listed below.

End Repair and dA-Tailing

| | |
|---|---|
| x µl | DNA (up to 1 µg) |
| 50-x µl | H2O |
| 7 µl | End Prep Buffer |
| 3 µl | End Prep Enzyme |

Total 60 µl

Put PCR tube in a thermocycler and perform the following steps:

Incubate at 20 for 30 minutes with lid off.

Incubate at 65 for 30 minutes.

Take out reaction and perform the next step immediately.

Outside Adapters Ligation

| | |
|---|---|
| 60 µl | DNA from above |
| 5 µl | Annealed OA1-F, 5 µM |
| 5 µl | Annealed OA2-R, 5 µM |
| 30 µl | Ligation Buffer |
| 10 µl | DNA Ligase |

Total 110 µl incubate at 16 for 18 hours.

Figure 21:
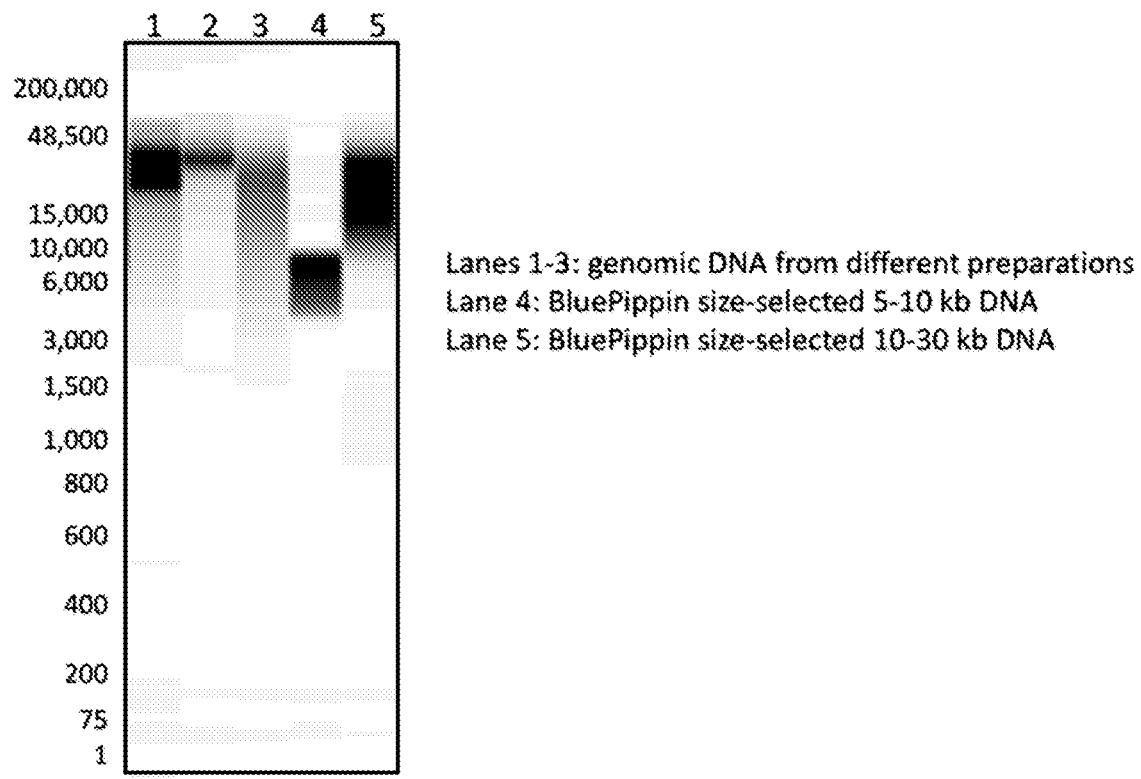
FIG. 21 shows DNA size selection using BluePippin (Sage Science) during Fiddler-Crab-Seq.

5. For 1-2 kb DNA, DNA from the adapter ligation reaction was purified using DNA Clean & Concentrator Kit (Zymo Research). For 5-10 kb and 10-30 kb DNA, to minimize DNA damage we used a mild DNA clean up protocol. First, Proteinase K was added to the adapter ligation reaction to digest enzymes. Second, Proteinase K was extracted using StrataClean Resin (Agilent Genomics) twice. Last, reaction mixture was dialysed in Tris-EDTA pH 8.0 buffer (5 mM Tris base, 0.05 mM EDTA). DNA was then size-selected using BluePippin (Sage Science) (FIG. 21).

6. Tn5 transposome was assembled using EZ-Tn5 Transposase (Epicentre) or Robust Tn5 Transposase (Creative Biogene) and Internal Adapter following vendors's protocols. An example setup is showing below.

| | |
|---|---|
| 13 μl | H2O |
| 2 μl | 10x TPS buffer |
| 1 μl | Annealed Internal Adapter, 40 μM |
| 4 μl | Robust Tn5 transposase |
| Total 20 μl | |

Incubate at 25 for 30-60 minutes.

7. The integrated tagmentation and emulsion PCR was set up using Micellula DNA Emulsion & Purification Kit (EURx) or in-house microfluidics devices. Average number of template copies per droplet was kept below 0.1, to minimize multiple copies of templates presenting in droplets. An example of emulsion PCR setup using Micellula DNA Emulsion & Purification Kit (EURx) is listed below.
Set up the following 50 ul reaction on ice.

| | |
|---|---|
| x μl | Outside Adapter ligated DNA (1x10^9 molecules) |
| 21.7-x μl | H2O |
| 10 μl | 5x TD (Creative Biogene) |
| 2.5 μl | dNTP, 10 mM |
| 2.5 μl | KCl, 2M |
| 0.5 μl | OA1-F-pcr, 2 μM |
| 0.5 μl | OA2-R-pcr, 2 μM |
| 1 μl | Crab_oligos, 10 μM |
| 0.4 μl | IA_pcr, 100 μM |
| 7.5 μl | Acetylated BSA, 10 mg/ml |
| 1 μl | USER (New England Biolabs) |
| 2 μl | SuperFi Polymerase (Thermo Fisher Scientific) |

Add pre-assembled Tn5 transposome right before adding oil and vortex.

| | |
|---|---|
| 0.4 μl | Pre-assembled Tn5 Transposome |

Add 300 ul ice cold emulsion PCR oil (220 μl of Emulsion Component 1, 20 μl of Emulsion Component 2, 60 μl of Emulsion Component 3, mix well).
Vortex at high speed at 4 for 3 minutes.
Put in thermocycler and run the following program:

| | |
|---|---|
| 37 , 30 min | (USER digestion, tagmentation) |
| 55 , 12 min | (tagmentation) |
| 94 , 10 min | (inactivate transposase) |
| 50 cycles | (amplification) |
| { | |
| 94 , 10 sec | |
| 60 , 45 sec | |
| 70 , 60 sec | |
| } | |

| | |
|---|---|
| 70 , 3 min | |
| 4 , hold | |

Breaking emulsion using Micellula DNA Emulsion & Purification Kit (EURx) following vendor's protocol.

8. Success PCR products, i.e., PCR products covalently linked by the Covalently linking oligos were enriched by biotin pulldown using the built-in DesthioBiotin in the Alkyne oligo and Dynabeads MyOne Streptavidin C1 (Thermo Fisher Scientific), following vendor's protocol. An example protocol is listed below.
Pulldown using MyOne C1 with Desthiobiotin-TEG
Wash 20 ul beads with 1000 ul 1× Binding and Washing Buffer (5 mM Tris-HCl (pH 7.5), 0.5 mM EDTA, 1 M NaCl) for 3 times.
Resuspend beads in 20 ul of 2× Binding and Washing Buffer (10 mM Tris-HCl (pH 7.5) 1 mM EDTA 2 M NaCl buffer.
Add beads to 20 ul eluted DNA from above breaking emulsion step.
Incubate at room temperature for 1 hour.
Wash twice with 200 ul of 1× Binding and Washing Buffer.
Remove washing buffer.
Add 50 ul of biotin elution buffer (100 mM Tris-HCl (pH 8.0), 250 mM NaCl, 1 mM EDTA, 10 mM D-biotin).
Incubate at room temperature for 1 hour.
Clean up DNA using DNA Clean & Concentrator Kit (Zymo Research).

9. PCR products were size-selected on 2% E-Gel (Thermo Fisher Scientific) for 500-1,000 bp range, and extracted using QIAquick Gel Extraction Kit (Qiagen).

10. Size-selected PCR products were digested using BseRI (New England Biolabs) at for 30 min following vendor's protocol and cleaned up using DNA Clean & Concentrator Kit (Zymo Research).

11. Circularization ligation was performed using T4 DNA ligase (New England Biolabs) at 16 for 1-16 hours and T4 DNA ligase was inactivated at 65 for 10 minutes.

12. Linear DNA was digested using Lambda Exonuclease (New England Biolabs) and Exonuclease I (New England Biolabs) at 37 for 30 min following vendor's protocol and cleaned up using DNA Clean & Concentrator Kit (Zymo Research).

13. Illumina sequencing adapters were added using PCR with indexed oligos (New England Biolabs) and NEBNext Ultra II Kit (New England Biolabs). Products were cleaned up using 0.9× Agencourt AMPure XP (Beckman Coulter) following NEBNext Ultra II Kit protocol.

14. Final library was sequenced on MiSeq System (Illumina) using MiSeq Reagent Kit v3 (600-cycle).

Figure 20A:
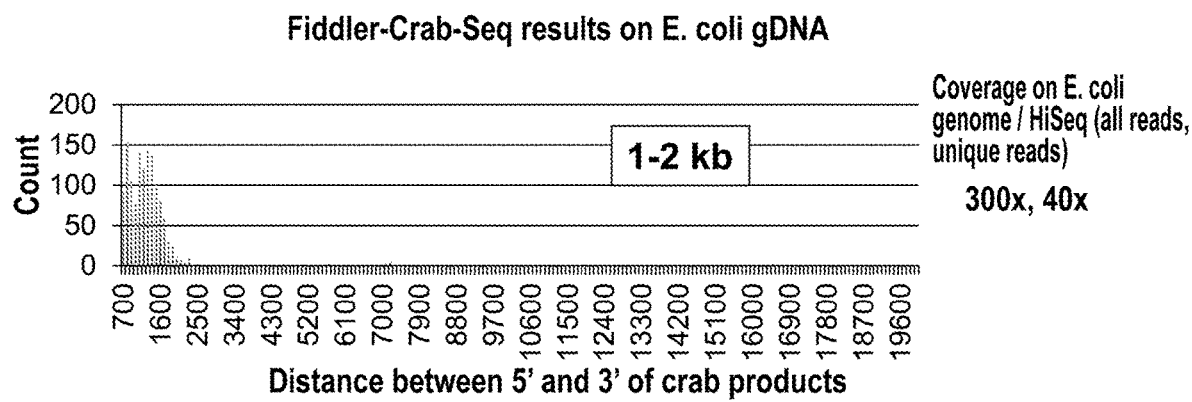
FIG. 20A shows Fiddler-Crab-Seq results on 1-2 kb *E. coli* gDNA.
Figure 20B:
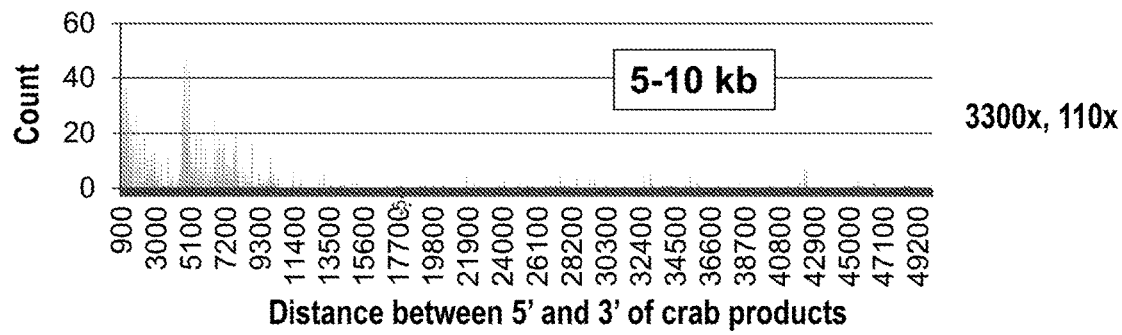
FIG. 20B shows Fiddler-Crab-Seq results on 5-10 kb *E. coli* gDNA.
Figure 20C:
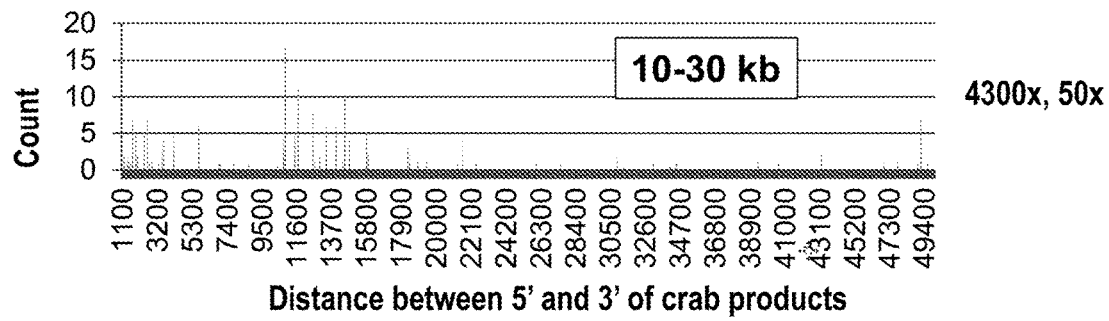
FIG. 20C shows Fiddler-Crab-Seq results on 10-30 kb *E. coli* gDNA.

15. Illumina sequencing results was split at the internal adapter junction, then 5' part and 3' part of each read were mapped to E. coli DH5α reference genome using Burrows-Wheeler Aligner (BWA) (Li H. and Durbin R. (2009) Bioinformatics, 25:1754.). The distance between the locations of 5' and 3' parts mapped to the reference genome was calculated for all reads. For the reads that have distance in the range of the length of the templates DNA, they were generated from the two ends of the template DNAs and provide long distance sequencing information. FIGS. 20A-20C show results of Fiddler-Crab-Seq results on *E. coli* gDNA.

Figure 22:
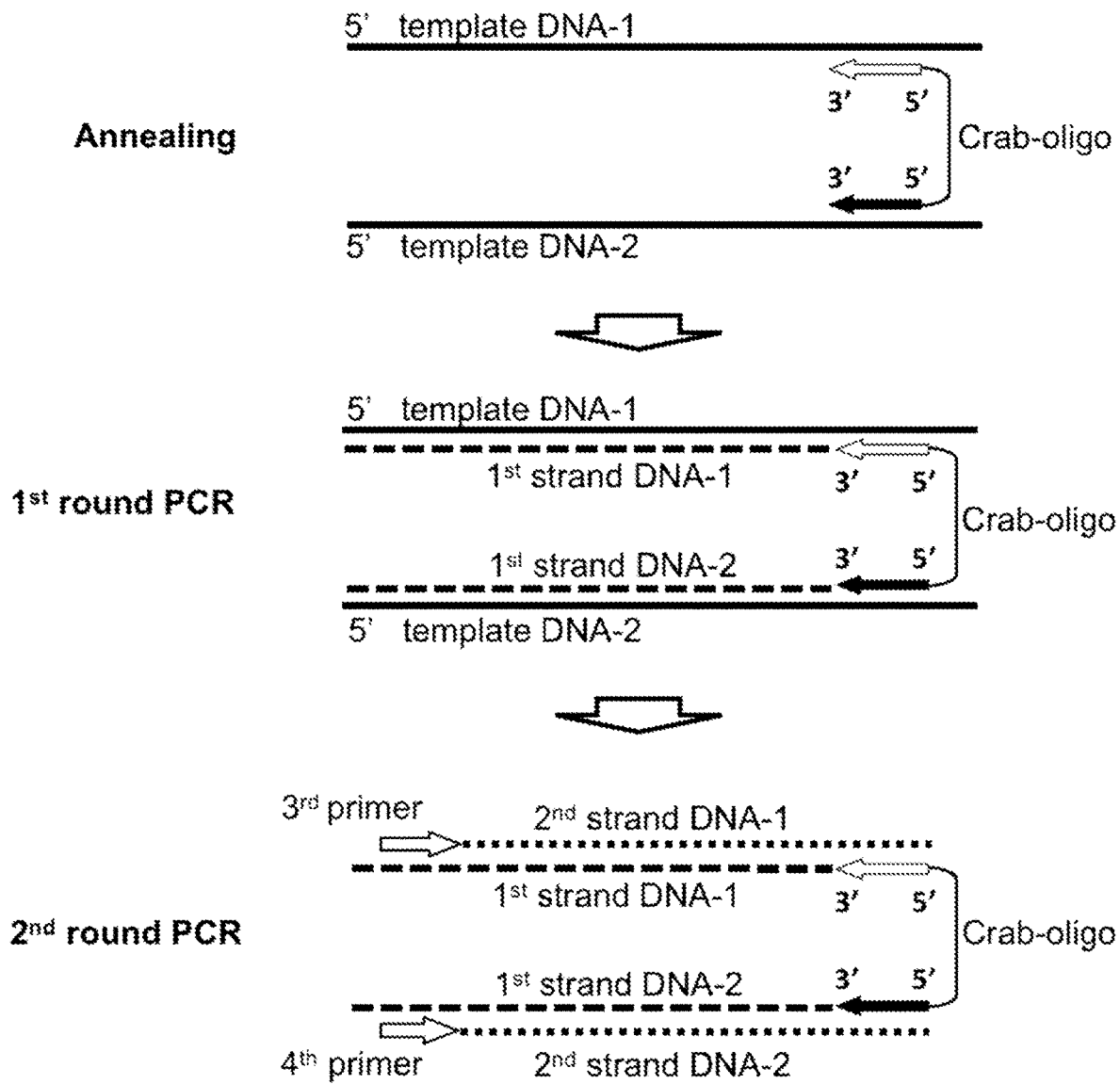
FIG. 22 shows a representation of the Crab-PCR procedure using DNA template.
Figure 23:
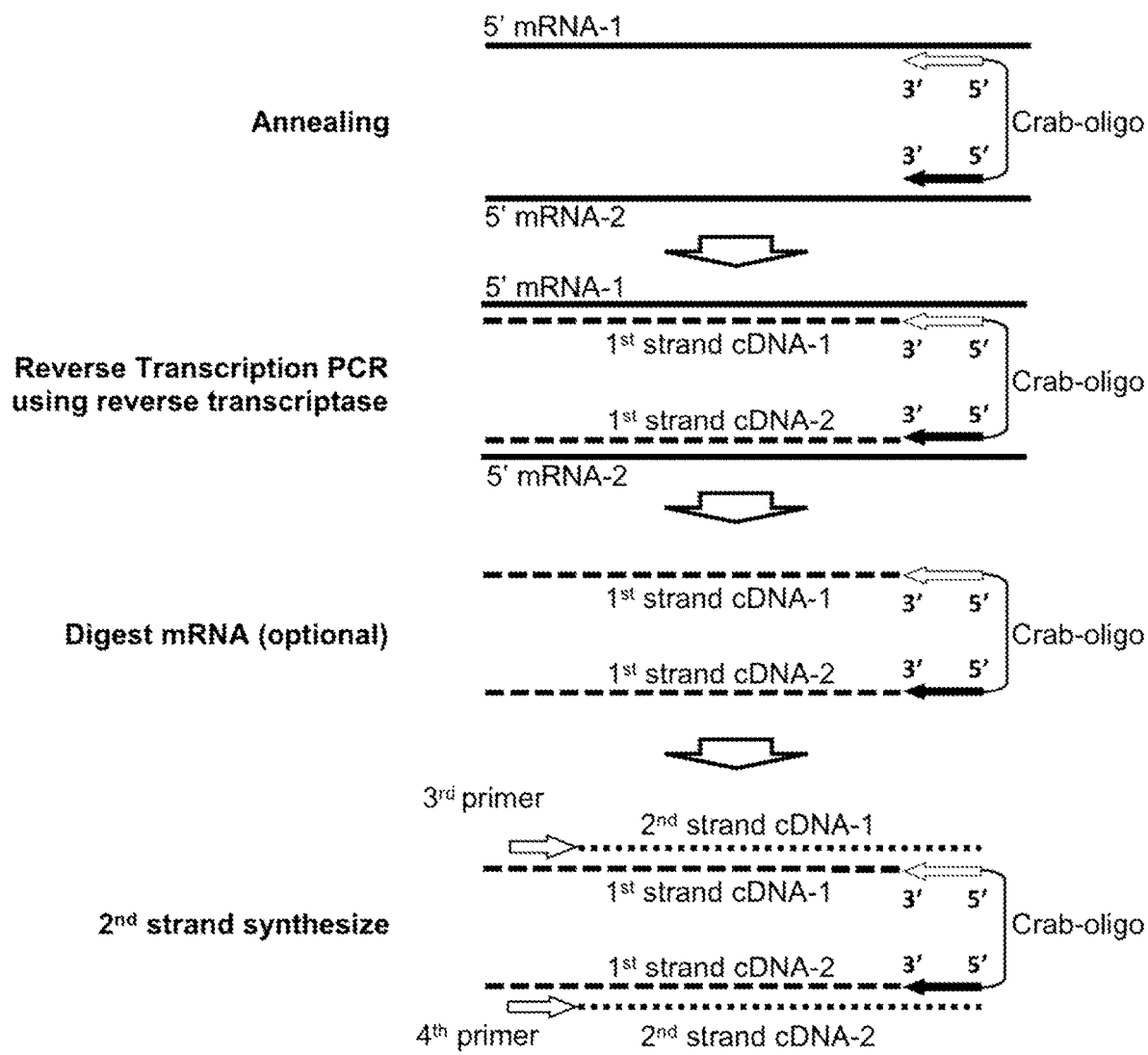
FIG. 23 shows a representation of the Crab-PCR procedure using mRNA template and mRNA specific third and fourth primers.
Figure 24:
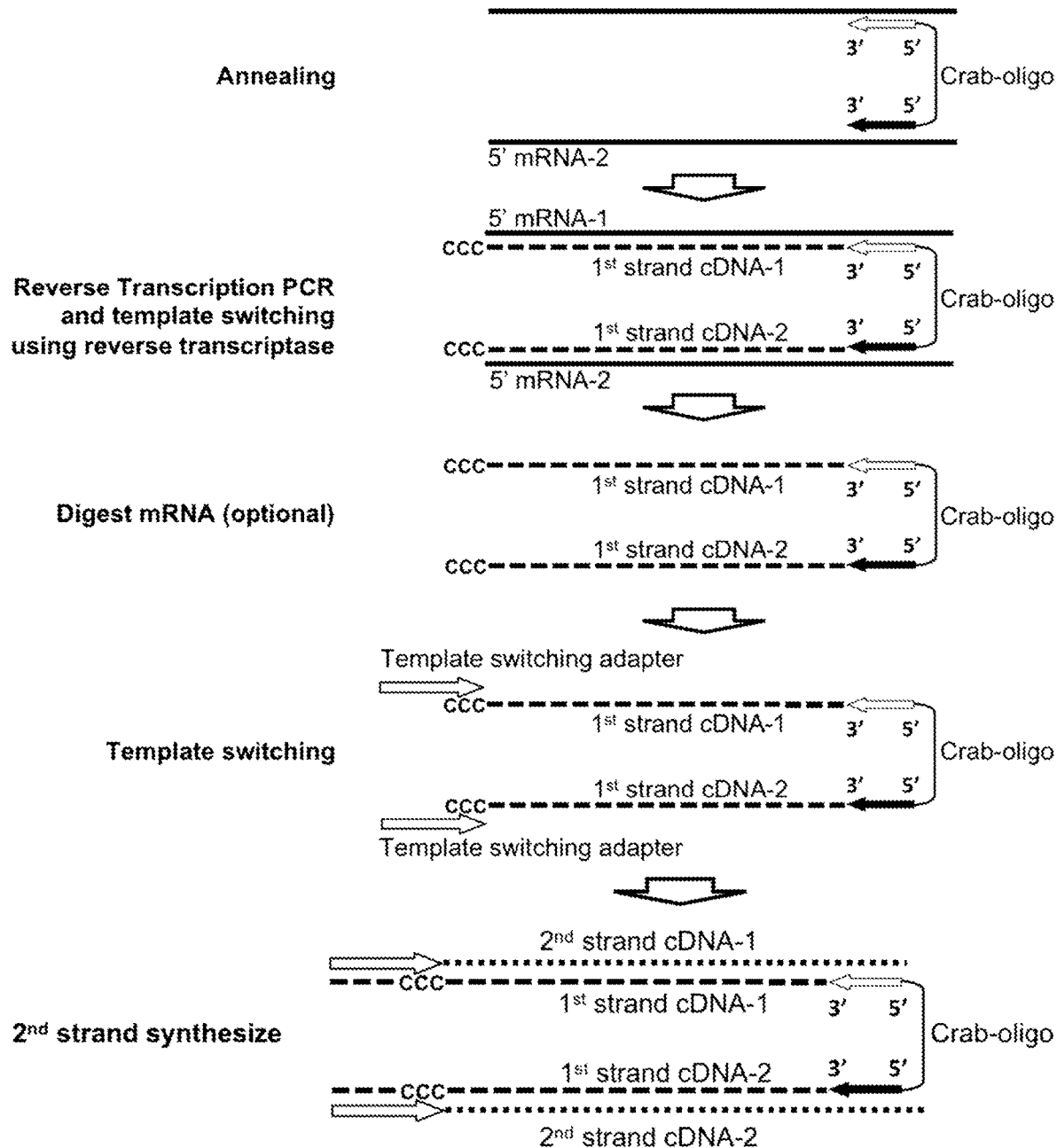
FIG. 24 shows a representation of the Crab-PCR procedure using mRNA template and a template switching adapter.

Example 14—Crab-PCR to Link and Pair Heavy and Light Chains mRNAs from Individual B Lymphocyte Hybridoma Cells FIG. 22 shows a schematic overview of the Crab-PCR using DNA templates. FIG. 23 shows a schematic overview of the Crab-PCR using mRNA template and mRNA specific amplification primers. FIG. 24 shows a schematic overview of the Crab-PCR using mRNA template, a template switching adapter and a common amplification primer, which is used by the Example below.

A. Cells:
*Mus musculus* B lymphocyte hybridoma MYC1-9E10.2 [9E10] (ATCC® CRL-1729™) from ATCC B. Oligos:

```
1. Hrev:
                                    (SEQ. ID. No: 33)
   5' AGGGGCCAGTGGATAGAC 2. Lrev:
                                    (SEQ. ID. No: 34)
   5' GATGGTGGGAAGATGGATAC 3. TSO:
                                    (SEQ. ID. No: 35)
   5' AAGCAGTGGTATCAACGCAGAGTACATrGrGrG 4. ISPCR:
                                    (SEQ. ID. No: 36)
   5' AAGCAGTGGTATCAACGCAGAGT
```

5. Covalently linking oligos:
Covalently linking oligos (Crab oligos) are covalently linked from these two oligos by their 5' and 5', using Azide-Alkyne Huisgen Cycloaddition.
Azide Hrev oligo (/5AzideN/=5' Azide (NHS Ester), /iSp-18/=Internal Spacer 18):

```
                                    (SEQ. ID. No: 37)
   5' /5AzideN//iSp18/AGGGGCCAGTGGATAGAC
```

Alkyne Lrev oligo (/5Hexynyl/=5' Hexynyl, /iSp18/=Internal Spacer 18):

```
                                    (SEQ. ID. No: 38)
   5'/5Hexynyl//iSp18/GATGGIGGGAAGATGGATAC
```

6. Type IIS site ISPCR:

```
ISPCR_AcuI:
                                    (SEQ. ID. No: 39)
   5' ACCAGCCTGAAGAGCAGTGGTATCAACGCAGAGT

ISPCR_BpuEI:
                                    (SEQ. ID. No: 40)
   5' ACCAGCCTTGAGAGCAGTGGTATCAACGCAGAGT

ISPCR_BsgI:
                                    (SEQ. ID. No: 41)
   5' ACCAGC GTGCAGAGCAGTGGTATCAACGCAGAGT
```

C. Steps:
1. Click chemistry to covalently link Azide oligo and Alkyne oligo.
   To make 10 mM Copper (II)-TBTA Stock in 55% DMSO:
   Dissolve 50 mg of copper (II) sulfate pentahydrate in 10 ml of distilled water.
   Dissolve 116 mg of TBTA ligand in 11 mL of DMSO.
   Mix two solutions.
   To make 2 M Triethylammonium Acetate Buffer, pH 7.0:
   Mix 2.78 mL of triethylamine with 1.14 mL of acetic acid.
   Add water to 10 mL volume, and adjust pH to 7.0.
   Click chemistry reaction setup:

| | |
   |---|---|
   | 30 µl | Azide Hrev oligo, 10 µM |
   | 30 µl | Alkyne Lrev oligo, 10 µM |
   | 7.5 µl | Triethylammonium Acetate Buffer, pH 7.0, 2M |
   | 67.5 µl | DMSO |
   | 15 µl | Ascorbic Acid, 5 mM, freshly made |
   | 8 µl | Copper (II)-TBTA Stock, 10 mM |

Total 158 µl

Incubate at room temperature for 1-24 hours.
   Purify DNA using Oligo Clean & Concentrator (Zymo Research).
   Size-selected clicked oligos using 4% E-Gel (Thermo Fisher Scientific) and clean up using using Oligo Clean & Concentrator (Zymo Research).
2. Single cells are sorted using FACS into PCR tubes or strips with each well containing 2.5 µl of $H_2O$ and 2.5 µl of OneTaq One-Step Reaction mix (2×) (New England Biolabs).
3. One-step reverse transcription PCR, template switching and PCR. OneTaq One-Step (New England Biolabs).

| | |
   |---|---|
   | 5 µl | Sorted single cell in OneTaq One-Step Reaction mix, 1x |
   | 1 µl | H2O |
   | 2.5 µl | OneTaq One-Step Reaction mix, 2x |
   | 0.5 µl | OneTaq One-Step Enzyme mix |
   | 0.2 µl | TSO, 100 µM |
   | 0.2 µl | ISPCR, 50 µM |
   | 0.2 µl | Hrev, 1 µM |
   | 0.2 µl | Lrev, 1 µM |
   | 0.2 µl | Crab, 10 µM |

Total 10 µl

Put in thermocycler and run the following program:

| | |
   |---|---|
   | 42 | 90 min |
   | 10 cycles | |
   | { | |
   | 50 | 2 min |
   | 42 | 2 min |
   | } | |
   | 94 | 1 min |
   | 50 cycles | |
   | { | |
   | 94 | 15 sec |
   | 52 | 30 sec |
   | 68 | 45 sec |
   | } | |
   | 68 | 5 min |
   | 4 | hold |

4. DNA clean up.
   AMPure beads purification, using 1× AMPure XP beads (Beckman Coulter).
   Elute in 10 µl of low TE buffer (Tris-EDTA pH 8.0 buffer (10 mM Tris base, 0.1 mM EDTA)).

Steps 5-8 are optional if using Sanger sequencing for final products readout. But these steps are required for Next Generation Sequencing, like Illumina Sequencing. Because without Type IIS digestion to remove part of the adapter, the junction region formed by the two adapters from two ends of the covalently linked PCR products will form hairpin on Illumina flowcell and affect sequencing results.

Steps 9-10 are optional if the DNA yield is sufficient for size-selection and Sanger sequencing after step 4. If the DNA yield is low, these steps are required, because the covalently linked PCR products need to be circularized and amplified to generate more DNA molecules. If Next Generation Sequencing, like Illumina Sequencing, will be performed, these steps are required because the covalently linked PCR products need to be circularized, and furthermore sequencing adapters need to be added.

5. One step PCR to add Type IIS restriction site.

| | |
|---|---|
| 9 μl | DNA from above step |
| 10 μl | Q5 Master Mix (New England Biolabs) |
| 1 μl | ISPCR_AcuI (or ISPCR_BpuEI, or ISPCR_BsgI), 20 μM |

Total 20 μl

Put in thermocycler and run the following program:

| | |
|---|---|
| 98 | 2 min |
| 52 | 30 sec |
| 68 | 3 min |
| 4 | hold |

6. DNA clean up.
   AMPure beads purification, using 1× AMPure XP beads (Beckman Coulter).
   Elute in 10 μl of low TE buffer (Tris-EDTA pH 8.0 buffer (10 mM Tris base, 0.1 mM EDTA)).
7. Type IIS restriction digestion.

| | |
|---|---|
| 10 μl | DNA from above step |
| 7.5 μl | H2O |
| 2 μl | Reaction buffer, 10x |
| 0.5 μl | AcuI (or BpuEI, or BsgI, if used according oligo in the above step) (New England Biolabs) |

Total 20 μl

Incubate at 37 for 30 minutes.
8. DNA clean up.
   AMPure beads purification, using 1× AMPure XP beads (Beckman Coulter).
   Elute in 10 μl of low TE buffer (Tris-EDTA pH 8.0 buffer (10 mM Tris base, 0.1 mM EDTA)).
9. Circularization ligation using T4 DNA ligase.

| | |
|---|---|
| 10 μl | DNA from above step |
| 7 μl | H2O |
| 2 μl | T4 DNA ligase reaction buffer, 10x |
| 1 μl | T4 DNA ligase |

Incubate at 16 for 12-20 hours.
Clean up using DNA Clean & Concentrator Kit (Zymo Research) and elute in 10 μl of low TE buffer.

10. PCR to amplify circularized DNA.

| | |
|---|---|
| 9 μl | DNA from above step |
| 10 μl | Q5 Master Mix (New England Biolabs) |
| 0.5 μl | Hrev (20 μM) |
| 0.5 μl | Lrev (20 μM) |

Total 20 μl

Put in thermocycler and run the following program:

| | |
|---|---|
| 98 | 1 min |
| 20 cycles { | |
| 98 | 10 sec |
| 52 | 30 sec |
| 68 | 45 sec |
| } | |
| 68 | 5 min |
| 4 | hold |

11. Size-selection.
    Size-select band of ~900 bp on 1% E-Gel (Thermo Fisher Scientific).
    Extract DNA using QIAquick Gel Extraction Kit (Qiagen).
12. Sanger sequencing using Hrev and Lrev.
    Sequencing results:

Heavy chain variable region (reverse complement of the sequencing result, in the direction of mRNA):
(SEQ. ID. No: 42)
5' GTCCTGGATTCGATTCCCAGTTCCTCACATTCAGGCAGCACTGAACA

CGGACCCCTCACCATGAACTTCGGGCTCAGCTTGATTTTCCTTGCCCTCA

TTTTAAAAGGTGTCCAGTGTGAGGTGCACCTGGTGGAGTCTGGGGGAGAC

TTAGTGAAGCCTGGAGGGTCCCTGAAACTCTCCTGTGCAGCCTCTGGATT

CACTTTCAGTCACTATGGCATGTCTTGGGTTCGCCAGACTCCAGACAAGA

GGCTGGAGTGGGTCGCAACCATTGGTAGTCGTGGTACTTACACCCACTAT

CCAGACAGTGTGAAGGGACGATTCACCATCTCCAGAGACAATGACAAGAA

CGCCCTGTACCTGCAAATGAACAGTCTGAAGTCTGAAGACACAGCCATGT

ATTACTGTGCAAGAAGAAGTGAATTTTATTACTACGGTAATACCTACTAT

TACTCTGCTATGGACTACTGGGGTCAAGGAGCCTCAGTCAC

Light chain variable region (reverse complement of the sequencing result, in the direction of mRNA):
(SEQ. ID. No: 43)
5' CTCAGAGATGGAGAAAGACACACTCCTGCTATGGGTCCTGCTTCTCT

GGGTTCCAGGTTCCACAGGTGACATTGTGCTGACCCAATCTCCAGCTTCT

TTGGCTGTATCTCTAGGACAGAGGGCCACCATCTCCTGCAGAGCCAGCGA

AAGTGTTGATAATTATGGCTTTAGTTTTATGAACTGGTTCCAGCAGAAAC

-continued

CAGGACAGCCCCCCAAACTCCTCATCTATGCTATATCCAACCGAGGATCC

GGGGTCCCTGCCAGGTTTAGTGGCAGTGGGTCTGGGACAGACTTCAGCCT

CAACATCCATCCTGTAGAGGAGGATGATCCTGCAATGTATTTCTGTCAGC

AAACTAAGGAGGTTCCGTGGACGTTCGGTGGAGGCACCAAGCTGGAAATC

AAACG

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for linking nucleic acid molecules or fragments thereof, comprising:
   (a) segregating individual nucleic acid molecules labeled on both terminal ends with a first adapter pair comprising a forward sequence (F) and a reverse sequence (R), into individual discrete volumes;
   (b) inserting, within the individual discrete volumes, at least a second adapter into two or more interior locations of the nucleic acid molecule;
   (c) fragmenting the nucleic acid molecules to generate nucleic acid fragments of the nucleic acid molecule of which a least a portion are labeled with both the first adapter pair and the second adapter;
   (d) contacting the nucleic acid fragments with at least a first and a second primer, wherein the first primer comprises at least two 5'-5'-linked arms, wherein a first arm of the at least two 5'-5'-linked arms comprises a sequence that hybridizes to the forward (F) sequence of the first adapter pair and a second arm of the at least two 5'-5'-linked arms comprises a sequence that hybridizes to the reverse (R) sequence of the first adapter pair, and wherein the second primer comprises a sequence that hybridizes to the second adapter; and
   (e) amplifying the nucleic acid molecules using both the first and second primers by PCR amplification or isothermal amplification.

2. The method of claim 1, further comprising:
   (f) pooling the amplified nucleic acid fragments from each individual discrete volume; and
   (g) circularizing the amplified nucleic acid fragments by joining the second adapters.

3. The method of claim 2, further comprising isolating the amplified nucleic acid fragments labeled with the first primer prior to the circularization step.

4. The method of claim 1, further comprising:
   (h) PCR amplification to generate linearized nucleic acid molecules comprising the second adapter; and
   (i) sequencing the linearized nucleic acid molecules to generate a set of nucleic acid reads.

5. The method of claim 4, further comprising:
   exonuclease digestion prior to the PCR amplification step;
   removing the first adapter pair sequence from the circularized nucleic acid molecules to generate linearized nucleic acid molecules comprising the second adapter prior to the PCR amplification step; or
   assembling a nucleic acid sequence of the nucleic acid molecules based, at least in part, on the set of nucleic acid sequencing reads.

6. The method of claim 3, wherein the amplified nucleic acid fragments labeled with the first primer are isolated via the binding tag.

7. The method of claim 1, wherein the forward (F) sequence and the reverse (R) sequence are:
- between 6 and 5000 nucleotides in length;
- the same; or
- different.

8. The method of claim 1, wherein the forward (F) sequence, the reverse (R) sequence, or the second adapter:
- further comprises a restriction site; or
- is removed or shortened from the circularized nucleic acid fragments by a restriction enzyme recognizing the restriction site.

9. The method of claim 8, wherein the restriction site is a Type IIS restriction site.

10. The method of claim 9, wherein the Type IIS restriction site is a SapI, AcuI, BpuEI, BsgI, BseRI, or EciI restriction site.

11. The method of any of claim 1, wherein the first arm of the first primer comprises a forward sequencing adapter sequence or a fragment thereof, and the second arm of the first primer comprises a reverse sequencing adapter sequence or a fragment thereof.

12. The method of claim 1, wherein the end-labeled nucleic acid molecules are fragmented by a transposase.

13. The method of claim 1, wherein the individual discrete volume is:
- a droplet generated by emulsification;
- a droplet generated by vortexing or shaking;
- a droplet generated on a microfluidic device;
- a droplet that comprises the transposase, the second adapter, and the first and the second primers;
- a hollow particle of sufficient size to hold reaction mixture; or
- a particle that is a section of a thin capillary tube and has a sufficient size to hold reaction mixture.

14. The method of claim 1, wherein the nucleic acid molecules:
- are DNA molecules;
- are RNA molecules;
- are 5 kb or longer;
- are 40-100 kb or longer; or
- encode T-cell receptor, B-cell receptor, or immunoglobulin heavy or light chain.

* * * * *

SEQUENCE LISTING

```
<160> NUMBER OF SEQ ID NOS: 43

<210> SEQ ID NO 1
<211> LENGTH: 8
<212> TYPE: DNA
<213> ORGANISM: Artificial Sequence
<220> FEATURE:
<223> OTHER INFORMATION: SapI restriction site
<220> FEATURE:
<221> NAME/KEY: misc_feature
<222> LOCATION: (8)..(8)
<223> OTHER INFORMATION: N = A or T or C or G

<400> SEQUENCE: 1 gctcttcn                                                              8

<210> SEQ ID NO 2
<211> LENGTH: 11
<212> TYPE: DNA
<213> ORGANISM: Artificial Sequence
<220> FEATURE:
<223> OTHER INFORMATION: SapI restriction site
<220> FEATURE:
<221> NAME/KEY: misc_feature
<222> LOCATION: (8)..(11)
<223> OTHER INFORMATION: N = A or T or G or C

<400> SEQUENCE: 2
cgagaagnnn n                                                         11

<210> SEQ ID NO 3
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (14)..(15)
<223> OTHER INFORMATION: Phosphorothioate bond
<220> FEATURE:
<221> NAME/KEY: misc_feature
<222> LOCATION: (15)..(16)
<223> OTHER INFORMATION: Phosphorothioate bond
<220> FEATURE:
<221> NAME/KEY: misc_feature
<222> LOCATION: (16)..(17)
<223> OTHER INFORMATION: Phosphorothioate bond
<220> FEATURE:
<221> NAME/KEY: misc_feature
<222> LOCATION: (17)..(18)
```

<223> OTHER INFORMATION: Phosphorothioate bond
<220> FEATURE:
<221> NAME/KEY: misc_feature
<222> LOCATION: (18)..(19)
<223> OTHER INFORMATION: Phosphorothioate bond
<220> FEATURE:
<221> NAME/KEY: misc_feature
<222> LOCATION: (19)..(20)
<223> OTHER INFORMATION: Phosphorothioate bond
<220> FEATURE:
<221> NAME/KEY: misc_feature
<222> LOCATION: (26)..(27)
<223> OTHER INFORMATION: Phosphorothioate bond
<220> FEATURE:
<221> NAME/KEY: misc_feature
<222> LOCATION: (27)..(28)
<223> OTHER INFORMATION: Phosphorothioate bond
<220> FEATURE:
<221> NAME/KEY: misc_feature
<222> LOCATION: (28)..(29)
<223> OTHER INFORMATION: Phosphorothioate bond
<220> FEATURE:
<221> NAME/KEY: misc_feature
<222> LOCATION: (29)..(30)
<223> OTHER INFORMATION: Phosphorothioate bond
<220> FEATURE:
<221> NAME/KEY: misc_feature
<222> LOCATION: (30)..(31)
<223> OTHER INFORMATION: Phosphorothioate bond
<220> FEATURE:
<221> NAME/KEY: misc_feature
<222> LOCATION: (31)..(32)
<223> OTHER INFORMATION: Phosphorothioate bond
<220> FEATURE:
<221> NAME/KEY: misc_feature
<222> LOCATION: (45)..(46)
<223> OTHER INFORMATION: Phosphorothioate bond

<400> SEQUENCE: 3
gatcggaaga gcgctggtgg taucgccacc agcgctcttc cgatct        46

<210> SEQ ID NO 4
<211> LENGTH: 33
<212> TYPE: DNA
<213> ORGANISM: Artificial Sequence
<220> FEATURE:
<223> OTHER INFORMATION: Synthetic Primer

<400> SEQUENCE: 4
acactctttc cctacacgac gctcttccga tct        33

<210> SEQ ID NO 5
<211> LENGTH: 34
<212> TYPE: DNA
<213> ORGANISM: Artificial Sequence
<220> FEATURE:
<223> OTHER INFORMATION: Synthetic Primer

<400> SEQUENCE: 5
gtgactggag ttcagacgtg tgctcttccg atct        34

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Azide modification followed by an internal
      spacer 18
<220> FEATURE:

```
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (2)..(3)
<223> OTHER INFORMATION: Phosphorothioate bond
<220> FEATURE:
<221> NAME/KEY: misc_feature
<222> LOCATION: (3)..(4)
<223> OTHER INFORMATION: Phosphorothioate bond
<220> FEATURE:
<221> NAME/KEY: misc_feature
<222> LOCATION: (4)..(5)
<223> OTHER INFORMATION: Phosphorothioate bond
<220> FEATURE:
<221> NAME/KEY: misc_feature
<222> LOCATION: (5)..(6)
<223> OTHER INFORMATION: Phosphorothioate bond
<220> FEATURE:
<221> NAME/KEY: misc_feature
<222> LOCATION: (6)..(7)
<223> OTHER INFORMATION: Phosphorothioate bond

<400> SEQUENCE: 6
acactctttc cctacacgac                                              20

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Hexynyl modification followed by an internal
      spacer 18
<220> FEATURE:
<221> NAME/KEY: misc_feature
<222> LOCATION: (1)..(2)
<223> OTHER INFORMATION: Phophorothioate bond
<220> FEATURE:
<221> NAME/KEY: misc_feature
<222> LOCATION: (2)..(3)
<223> OTHER INFORMATION: Phophorothioate bond
<220> FEATURE:
<221> NAME/KEY: misc_feature
<222> LOCATION: (3)..(4)
<223> OTHER INFORMATION: Phophorothioate bond
<220> FEATURE:
<221> NAME/KEY: misc_feature
<222> LOCATION: (4)..(5)
<223> OTHER INFORMATION: Phophorothioate bond
<220> FEATURE:
<221> NAME/KEY: misc_feature
<222> LOCATION: (5)..(6)
<223> OTHER INFORMATION: Phophorothioate bond
<220> FEATURE:
<221> NAME/KEY: misc_feature
<222> LOCATION: (6)..(7)
<223> OTHER INFORMATION: Phophorothioate bond

<400> SEQUENCE: 7
gtgactggag ttcagacgtg t                                            21

<210> SEQ ID NO 8
<211> LENGTH: 27
<212> TYPE: DNA
<213> ORGANISM: Artificial Sequence
<220> FEATURE:
<223> OTHER INFORMATION: Synthetic Primer

<400> SEQUENCE: 8
```
ccaccagcct gtctcttata cacatct                                              27

<210> SEQ ID NO 9
<211> LENGTH: 27
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Phosphorylation

<400> SEQUENCE: 9
agatgtgtat aagagacagg ctggtgg                                              27

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
gaggagagat gtgtataaga gacag                                                25

<210> SEQ ID NO 11
<211> LENGTH: 25
<212> TYPE: DNA
<213> ORGANISM: Artificial Sequence
<220> FEATURE:
<223> OTHER INFORMATION: Synthetic Primer

<400> SEQUENCE: 11
ctgtctctta tacacatctc tcctc                                                25

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
ggcggaagat gtgtataaga gacag                                                25

<210> SEQ ID NO 13
<211> LENGTH: 25
<212> TYPE: DNA
<213> ORGANISM: Artificial Sequence
<220> FEATURE:
<223> OTHER INFORMATION: Synthetic Primer

<400> SEQUENCE: 13
ctgtctctta tacacatctt ccgcc                                                25

<210> SEQ ID NO 14
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Phosphorylation
<220> FEATURE:
<221> NAME/KEY: misc_feature

```
<222> LOCATION: (14)..(15)
<223> OTHER INFORMATION: Phosphorothioate bond
<220> FEATURE:
<221> NAME/KEY: misc_feature
<222> LOCATION: (15)..(16)
<223> OTHER INFORMATION: Phosphorothioate bond
<220> FEATURE:
<221> NAME/KEY: misc_feature
<222> LOCATION: (16)..(17)
<223> OTHER INFORMATION: Phosphorothioate bond
<220> FEATURE:
<221> NAME/KEY: misc_feature
<222> LOCATION: (17)..(18)
<223> OTHER INFORMATION: Phosphorothioate bond
<220> FEATURE:
<221> NAME/KEY: misc_feature
<222> LOCATION: (18)..(19)
<223> OTHER INFORMATION: Phosphorothioate bond
<220> FEATURE:
<221> NAME/KEY: misc_feature
<222> LOCATION: (19)..(20)
<223> OTHER INFORMATION: Phosphorothioate bond
<220> FEATURE:
<221> NAME/KEY: misc_feature
<222> LOCATION: (26)..(27)
<223> OTHER INFORMATION: Phosphorothioate bond
<220> FEATURE:
<221> NAME/KEY: misc_feature
<222> LOCATION: (27)..(28)
<223> OTHER INFORMATION: Phosphorothioate bond
<220> FEATURE:
<221> NAME/KEY: misc_feature
<222> LOCATION: (28)..(29)
<223> OTHER INFORMATION: Phosphorothioate bond
<220> FEATURE:
<221> NAME/KEY: misc_feature
<222> LOCATION: (29)..(30)
<223> OTHER INFORMATION: Phosphorothioate bond
<220> FEATURE:
<221> NAME/KEY: misc_feature
<222> LOCATION: (30)..(31)
<223> OTHER INFORMATION: Phosphorothioate bond
<220> FEATURE:
<221> NAME/KEY: misc_feature
<222> LOCATION: (31)..(32)
<223> OTHER INFORMATION: Phosphorothioate bond
<220> FEATURE:
<221> NAME/KEY: misc_feature
<222> LOCATION: (45)..(46)
<223> OTHER INFORMATION: Phosphorothioate bond

<400> SEQUENCE: 14
gatcggaaga gcgctggtgg taucgccacc agcgctcttc cgatct          46

<210> SEQ ID NO 15
<211> LENGTH: 33
<212> TYPE: DNA
<213> ORGANISM: Artificial Sequence
<220> FEATURE:
<223> OTHER INFORMATION: Synthetic Primer

<400> SEQUENCE: 15
acactctttc cctacacgac gctcttccga tct                         33

<210> SEQ ID NO 16
<211> LENGTH: 34
<212> TYPE: DNA
<213> ORGANISM: Artificial Sequence
<220> FEATURE:
<223> OTHER INFORMATION: Synthetic Primer

<400> SEQUENCE: 16
gtgactggag ttcagacgtg tgctcttccg atct                        34
```

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Azide modification followed by an internal
      spacer 18
<220> FEATURE:
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (2)..(3)
<223> OTHER INFORMATION: Phosphorothioate bond
<220> FEATURE:
<221> NAME/KEY: misc_feature
<222> LOCATION: (3)..(4)
<223> OTHER INFORMATION: Phosphorothioate bond
<220> FEATURE:
<221> NAME/KEY: misc_feature
<222> LOCATION: (4)..(5)
<223> OTHER INFORMATION: Phosphorothioate bond
<220> FEATURE:
<221> NAME/KEY: misc_feature
<222> LOCATION: (5)..(6)
<223> OTHER INFORMATION: Phosphorothioate bond
<220> FEATURE:
<221> NAME/KEY: misc_feature
<222> LOCATION: (6)..(7)
<223> OTHER INFORMATION: Phosphorothioate bond

<400> SEQUENCE: 17
acactctttc cctacacgac                                              20

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Hexynyl modification followed by an internal
      spacer 18
<220> FEATURE:
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (2)..(3)
<223> OTHER INFORMATION: Phosphorothioate bond
<220> FEATURE:
<221> NAME/KEY: misc_feature
<222> LOCATION: (3)..(4)
<223> OTHER INFORMATION: Phosphorothioate bond
<220> FEATURE:
<221> NAME/KEY: misc_feature
<222> LOCATION: (4)..(5)
<223> OTHER INFORMATION: Phosphorothioate bond
<220> FEATURE:
<221> NAME/KEY: misc_feature
<222> LOCATION: (5)..(6)
<223> OTHER INFORMATION: Phosphorothioate bond
<220> FEATURE:
<221> NAME/KEY: misc_feature
<222> LOCATION: (6)..(7)
<223> OTHER INFORMATION: Phosphorothioate bond

<400> SEQUENCE: 18
gtgactggag ttcagacgtg t                                              21

<210> SEQ ID NO 19
<211> LENGTH: 25
<212> TYPE: DNA
<213> ORGANISM: Artificial Sequence
<220> FEATURE:
<223> OTHER INFORMATION: Synthetic Primer

<400> SEQUENCE: 19
gaggagagat gtgtataaga gacag                                          25

<210> SEQ ID NO 20
<211> LENGTH: 25
<212> TYPE: DNA
<213> ORGANISM: Artificial Sequence
<220> FEATURE:
<223> OTHER INFORMATION: Synthetic Primer

<400> SEQUENCE: 20
ctgtctctta tacacatctc tcctc                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic Primer

<400> SEQUENCE: 21
gaggagagat gtgtataaga gacag                                          25

<210> SEQ ID NO 22
<211> LENGTH: 92
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Phosphorylation
<220> FEATURE:
<221> NAME/KEY: misc_feature
<222> LOCATION: (91)..(92)
<223> OTHER INFORMATION: Phosphorothioate bond

<400> SEQUENCE: 22
gatcggaaga gcgtcgtgta gggaaagagt gttutccttc ccttcccttc ccttcctuta    60
cactctttcc ctacacgacg ctcttccgat ct                                  92

<210> SEQ ID NO 23
<211> LENGTH: 70
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Phosphorylation
<220> FEATURE:
<221> NAME/KEY: misc_feature
<222> LOCATION: (69)..(70)
<223> OTHER INFORMATION: Phosphorothioate bond

<400> SEQUENCE: 23

```
gatcggaaga gcgtcgtgta gggaaagagt gttaucgaca ctctttccct acacgacgct    60
cttccgatct                                                          70
```

<210> SEQ ID NO 24
<211> LENGTH: 94
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Phosphorylation
<220> FEATURE:
<221> NAME/KEY: misc_feature
<222> LOCATION: (93)..(94)
<223> OTHER INFORMATION: Phosphorothioate bond

<400> SEQUENCE: 24

```
gatcggaaga gcacacgtct gaactccagt cactutggtg gtggtgggtt gttgttgtut    60
gtgactggag ttcagacgtg tgctcttccg atct                               94
```

<210> SEQ ID NO 25
<211> LENGTH: 72
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Phosphorylation
<220> FEATURE:
<221> NAME/KEY: misc_feature
<222> LOCATION: (71)..(72)
<223> OTHER INFORMATION: Phosphorothioate bond

<400> SEQUENCE: 25

```
gatcggaaga gcacacgtct gaactccagt cactaugcgt gactggagtt cagacgtgtg    60
ctcttccgat ct                                                       72
```

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26

```
acactctttc cctacacgac                                               20
```

<210> SEQ ID NO 27
<211> LENGTH: 21
<212> TYPE: DNA
<213> ORGANISM: Artificial Sequence
<220> FEATURE:
<223> OTHER INFORMATION: Synthetic Primer

<400> SEQUENCE: 27

```
gtgactggag ttcagacgtg t                                             21
```

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: misc_feature
<222> LOCATION: (1)..(1)
<223> OTHER INFORMATION: 5' Azide modification followed by internal
      spacer 18
<220> FEATURE:
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (2)..(3)
<223> OTHER INFORMATION: Phosphorothioate bond
<220> FEATURE:
<221> NAME/KEY: misc_feature
<222> LOCATION: (3)..(4)
<223> OTHER INFORMATION: Phosphorothioate bond
<220> FEATURE:
<221> NAME/KEY: misc_feature
<222> LOCATION: (4)..(5)
<223> OTHER INFORMATION: Phosphorothioate bond
<220> FEATURE:
<221> NAME/KEY: misc_feature
<222> LOCATION: (5)..(6)
<223> OTHER INFORMATION: Phosphorothioate bond
<220> FEATURE:
<221> NAME/KEY: misc_feature
<222> LOCATION: (6)..(7)
<223> OTHER INFORMATION: Phosphorothioate bond

<400> SEQUENCE: 28
acactctttc cctacacgac                                                     20

<210> SEQ ID NO 29
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Hexynyl modification followed by internal
      spacer 18
<220> FEATURE:
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (2)..(3)
<223> OTHER INFORMATION: Phosphorothioate bond
<220> FEATURE:
<221> NAME/KEY: misc_feature
<222> LOCATION: (3)..(4)
<223> OTHER INFORMATION: Phosphorothioate bond
<220> FEATURE:
<221> NAME/KEY: misc_feature
<222> LOCATION: (4)..(5)
<223> OTHER INFORMATION: Phosphorothioate bond
<220> FEATURE:
<221> NAME/KEY: misc_feature
<222> LOCATION: (5)..(6)
<223> OTHER INFORMATION: Phosphorothioate bond
<220> FEATURE:
<221> NAME/KEY: misc_feature
<222> LOCATION: (6)..(7)
<223> OTHER INFORMATION: Phosphorothioate bond

<400> SEQUENCE: 29
gtgactggag ttcagacgtg t                                                   21

<210> SEQ ID NO 30
<211> LENGTH: 25
<212> TYPE: DNA
```

<213> ORGANISM: Artificial Sequence
<220> FEATURE:
<223> OTHER INFORMATION: Synthetic Primer

<400> SEQUENCE: 30
gaggagagat gtgtataaga gacag                                            25

<210> SEQ ID NO 31
<211> LENGTH: 25
<212> TYPE: DNA
<213> ORGANISM: Artificial Sequence
<220> FEATURE:
<223> OTHER INFORMATION: Synthetic Primer

<400> SEQUENCE: 31
ctgtctctta tacacatctc tcctc                                            25

<210> SEQ ID NO 32
<211> LENGTH: 25
<212> TYPE: DNA
<213> ORGANISM: Artificial Sequence
<220> FEATURE:
<223> OTHER INFORMATION: Synthetic Primer

<400> SEQUENCE: 32
gaggagagat gtgtataaga gacag                                            25

<210> SEQ ID NO 33
<211> LENGTH: 18
<212> TYPE: DNA
<213> ORGANISM: Artificial Sequence
<220> FEATURE:
<223> OTHER INFORMATION: Synthetic Primer

<400> SEQUENCE: 33
aggggccagt ggatagac                                                    18

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
gatggtggga agatggatac                                                  20

<210> SEQ ID NO 35
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(30)
<223> OTHER INFORMATION: this base is a ribonucleotide

<400> SEQUENCE: 35
aagcagtggt atcaacgcag agtacatggg                                       30

<210> SEQ ID NO 36
<211> LENGTH: 23
<212> TYPE: DNA
<213> ORGANISM: Artificial Sequence
<220> FEATURE:
<223> OTHER INFORMATION: Synthetic Primer -continued

<400> SEQUENCE: 36
aagcagtggt atcaacgcag agt                                            23

<210> SEQ ID NO 37
<211> LENGTH: 18
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (1)..(1)
<223> OTHER INFORMATION: 5' Azide modification followed by internal
      spacer 18

<400> SEQUENCE: 37
aggggccagt ggatagac                                                  18

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Hexynyl modification followed by internal
      spacer 18

<400> SEQUENCE: 38
gatggtggga agatggata                                                 19

<210> SEQ ID NO 39
<211> LENGTH: 34
<212> TYPE: DNA
<213> ORGANISM: Artificial Sequence
<220> FEATURE:
<223> OTHER INFORMATION: Synthetic Primer

<400> SEQUENCE: 39
accagcctga agagcagtgg tatcaacgca gagt                                34

<210> SEQ ID NO 40
<211> LENGTH: 34
<212> TYPE: DNA
<213> ORGANISM: Artificial Sequence
<220> FEATURE:
<223> OTHER INFORMATION: Synthetic Primer

<400> SEQUENCE: 40
accagccttg agagcagtgg tatcaacgca gagt                                34

<210> SEQ ID NO 41
<211> LENGTH: 34
<212> TYPE: DNA
<213> ORGANISM: Artificial Sequence
<220> FEATURE:
<223> OTHER INFORMATION: Synthetic Primer

<400> SEQUENCE: 41
accagcgtgc agagcagtgg tatcaacgca gagt                                34

<210> SEQ ID NO 42
<211> LENGTH: 488
<212> TYPE: DNA

```
<213> ORGANISM: Artificial Sequence
<220> FEATURE:
<223> OTHER INFORMATION: Synthetic Oligonucleotide

<400> SEQUENCE: 42
gtcctggatt cgattcccag ttcctcacat tcaggcagca ctgaacacgg acccctcacc      60
atgaacttcg ggctcagctt gattttcctt gccctcattt taaaaggtgt ccagtgtgag     120
gtgcacctgg tggagtctgg gggagactta gtgaagcctg gagggtccct gaaactctcc     180
tgtgcagcct ctggattcac tttcagtcac tatggcatgt cttgggttcg ccagactcca     240
gacaagaggc tggagtgggt cgcaaccatt ggtagtcgtg gtacttacac ccactatcca     300
gacagtgtga agggacgatt caccatctcc agagacaatg acaagaacgc cctgtacctg     360
caaatgaaca gtctgaagtc tgaagacaca gccatgtatt actgtgcaag aagaagtgaa     420
ttttattact acggtaatac ctactattac tctgctatgg actactgggg tcaaggagcc     480
tcagtcac                                                              488

<210> SEQ ID NO 43
<211> LENGTH: 402
<212> TYPE: DNA
<213> ORGANISM: Artificial Sequence
<220> FEATURE:
<223> OTHER INFORMATION: Synthetic Oligonucleotide

<400> SEQUENCE: 43
ctcagagatg gagaaagaca cactcctgct atgggtcctg cttctctggg ttccaggttc      60
cacaggtgac attgtgctga cccaatctcc agcttctttg gctgtatctc taggacagag     120
ggccaccatc tcctgcagag ccagcgaaag tgttgataat tatggcttta gttttatgaa     180
ctggttccag cagaaaccag gacagccccc caaactcctc atctatgcta tatccaaccg     240
aggatccggg gtccctgcca ggtttagtgg cagtgggtct gggacagact tcagcctcaa     300
catccatcct gtagaggagg atgatcctgc aatgtatttc tgtcagcaaa ctaaggaggt     360
tccgtggacg ttcggtggag gcaccaagct ggaaatcaaa cg                        402
```